US012758594B2

(12) United States Patent
Bakdash et al.

(10) Patent No.: US 12,758,594 B2
(45) Date of Patent: Oct. 13, 2026

(54) THERAPEUTIC BACTERIAL COMPOSITION

(71) Applicant: Microbiotica Limited, Cambridge (GB)

(72) Inventors: Ghaith Bakdash, Cambridge (GB); Simon Harris, Cambridge (GB); Dominika Klisko, Cambridge (GB); Trevor Lawley, Cambridge (GB); Seánín McCluskey, Cambridge (GB); Thomas Mitchell, Cambridge (GB); Anne Neville, Cambridge (GB); Amy Popple, Cambridge (GB); Oliver Rimington, Cambridge (GB); Matthew Robinson, Cambridge (GB); Michael Romanos, Cambridge (GB); Adam Wilkinson, Cambridge (GB)

(73) Assignee: MICROBIOTICA LIMITED, Cambridge (GB)

( * ) Notice: Subject to any disclaimer, the term of this patent is extended or adjusted under 35 U.S.C. 154(b) by 501 days.

(21) Appl. No.: 18/247,383

(22) PCT Filed: Oct. 4, 2021

(86) PCT No.: PCT/GB2021/052558
§ 371 (c)(1),
(2) Date: Mar. 30, 2023

(87) PCT Pub. No.: WO2022/069907
PCT Pub. Date: Apr. 7, 2022

(65) Prior Publication Data

US 2024/0000861 A1 Jan. 4, 2024

(30) Foreign Application Priority Data

Oct. 2, 2020 (GB) ..................................... 2015687

(51) Int. Cl.
*A61K 35/741* (2015.01)
*A61K 35/00* (2006.01)
(Continued)

(52) U.S. Cl.
CPC .......... *A61K 35/741* (2013.01); *A61K 35/742* (2013.01); *A61K 35/745* (2013.01);
(Continued)

(58) Field of Classification Search
CPC .... A61K 35/74; A61K 35/741; A61K 35/742; A61K 2300/00; A61K 2035/115;
(Continued)

(56) References Cited

U.S. PATENT DOCUMENTS

2014/0199281 A1* 7/2014 Henn ..................... A61K 38/13 424/93.46
2018/0273940 A1 9/2018 Sommer et al.
(Continued)

FOREIGN PATENT DOCUMENTS

FR 2920306 A1 3/2009
WO 2012142605 A1 10/2012
(Continued)

OTHER PUBLICATIONS

Million et al., (Scientific Reports, 6, Article No. 26051 (2016) i (Year: 2016).*
(Continued)

*Primary Examiner* — Jana A Hines
(74) *Attorney, Agent, or Firm* — Myers Bigel, P.A.

(57) ABSTRACT

The disclosure relates to therapeutic compositions comprising isolated bacteria useful in the treatment of ulcerative colitis or Crohn's disease. Related methods and uses are also disclosed.

14 Claims, 11 Drawing Sheets

Specification includes a Sequence Listing.

(51) Int. Cl.

| | |
|---|---|
| ***A61K 35/742*** | (2015.01) |
| ***A61K 35/745*** | (2015.01) |
| ***A61P 1/04*** | (2006.01) |
| ***C12Q 1/6869*** | (2018.01) |
| ***C12Q 1/689*** | (2018.01) |

(52) U.S. Cl.
CPC .............. *A61P 1/04* (2018.01); *C12Q 1/6869* (2013.01); *C12Q 1/689* (2013.01); *A61K 2035/115* (2013.01)

(58) Field of Classification Search
CPC .. A23L 33/135; A61P 1/00; A61P 1/04; A61P 29/00; C12Q 1/6869; C12Q 1/689; Y02A 50/30
See application file for complete search history.

(56) References Cited

U.S. PATENT DOCUMENTS

| | | | |
|---|---|---|---|
| 2019/0209626 | A1 | 7/2019 | Li et al. |
| 2019/0262407 | A1 | 8/2019 | Dutta |

FOREIGN PATENT DOCUMENTS

| | | | | |
|---|---|---|---|---|
| WO | 2013171515 A1 | 11/2013 | | |
| WO | 2014196913 A1 | 12/2014 | | |
| WO | 2017134240 A1 | 8/2017 | | |
| WO | 2017182796 A1 | 10/2017 | | |
| WO | WO-2019089643 A1 * | 5/2019 | ........... | A61K 35/742 |
| WO | WO-2019136269 A1 * | 7/2019 | ............... | C12N 1/20 |
| WO | 2019227414 A1 | 12/2019 | | |

OTHER PUBLICATIONS

"International Search Report and Written Opinion corresponding to International Application No. PCT/GB2021/052558 mailed Mar. 7, 2022".
Costello, Samuel P., et al., "Effect of Fecal Microbiota Transplantation on 8-Week Remission in Patients With Ulcerative Colitis : A Randomized Clinical Trial", JAMA the Journal of the American Medical Association 321(2):156 (Jan. 15, 2019).
Costello, S P, et al., "Systematic review with meta-analysis: faecal microbiota transplantation for the induction of remission for active ulcerative colitis", Alimentary Pharmacology & Therapeutics 46(3):213-224 (Aug. 1, 2017).
Kump, P , et al., "The taxonomic composition of the donor intestinal microbiota is a major factor influencing the efficacy of faecal microbiota transplantation in therapy refractory ulcerative colitis", Alimentary Pharmacology & Therapeutics 47(1):67-77 (Jan. 1, 2018).
Moayyedi, Paul , et al., "Fecal Microbiota Transplantation Induces Remission in Patients with Active Ulcerative Colitis in a Randomized Controlled Trial", Gastroenterology 149(1):102-109 (Jul. 1, 2015).
Scott, K P, et al., "Manipulating the gut microbiota to maintain health and treat disease", Microbial Ecology in Health & Disease 26:25877-1 (Feb. 2, 2015).
Abdulrazeg, Omnia , et al., "Management of ulcerative colitis: summary of updated NICE guidance", BMJ 367: 5897 doi: 10.1136/bmj.15897 (Oct. 28, 2019).
Bujko, Anna , et al., "Transcriptional and functional profiling defines human small intestinal macrophage subsets", Journal of Experimental Medicine 215(2):441-458 (2018).
Caviglia, Renato , et al., "Long-term treatment with infliximab in inflammatory bowel disease: safety and tolerability Issues", Expert Opinion on Drug Safety 7(5):617-632 (Sep. 1, 2008).
Farrell, Richard J, "Biologics beyond Anti-TNF Agents for Ulcerative Colitis—Efficacy, Safety, and Cost?", New England Journal of Medicine 381(13):1279-1281 (Sep. 26, 2019).
GBD 2017 Inflammatory Bowel Dise , et al., "The global, regional, and national burden of inflammatory bowel disease in 195 countries and territories, 1990-2017: a systematic analysis for the Global Burden of Disease Study 2017", Lancet Gastroenterol Hepatol 5:17-30 (Oct. 21, 2019).
Johnson, Andrew D, "An extended IUPAC nomenclature code for polymorphic nucleic acids", Bioinformatics 26 (10):1386-1389 (Mar. 3, 2010).
Kiesler, Patricia , et al., "Experimental Models of Inflammatory Bowel Diseases", Cell Mol Gastroenterol Hepatol 1:154-170 (2015).
Koelink, Pim J, et al., "Development of Reliable, Valid and Responsive Scoring Systems for Endoscopy and Histology in Animal Models for Inflammatory Bowel Disease", Journal of Crohn's and Colitis pp. 794-803 (Mar. 28, 2018).
Metwaly, Amira , et al., "Integrated microbiota and metabolite profiles link Crohn's disease to sulfur metabolism", Nature Communications 11:4322 (2020) 16 pages.
Neurath, Markus F, "Host-microbiota interactions in inflammatory bowel disease", Gastroenterology & Hepatology 17:76-77 (Feb. 2020).
Pandiyan, Pushpa , et al., "Microbiome Dependent Regulation of Tregs and Th17 Cells in Mucosa", Frontiers in Immunology 10:Article 426 (Mar. 8, 2019) 17 pages.
Roncarolo, Maria Grazia, et al., "Tr1 Cells and the Counter-Regulation of Immunity: Natural Mechanisms and Therapeutic Applications", Interleukin-10 in Health and Disease, Current Topics in Microbiology and Immunology 380:39-68 (2014).
Rutgeerts, Paul , et al., "Infliximab for Induction and Maintenance Therapy for Ulcerative Colitis", N Engl J Med 353:2462-2476 (Dec. 8, 2005).
Sokol, Harry , et al., "Fecal microbiota transplantation to maintain remission in Crohn's disease: a pilot randomized controlled study", Microbiome 8:12 (2020) 15 pages.
Torres, Joana , et al., "Crohn's disease", Lancet 389: 1741-1755 (Nov. 30, 2016).
Ungaro, Ryan , et al., "Ulcerative colitis", Lancet 389: 1756-1770 (Nov. 30, 2016).
Van Herk, Egbert H, et al., "Treg subsets in inflammatory bowel disease and colorectal carcinoma: Characteristics, role, and therapeutic targets", Journal of Gastroenterology and Hepatology 31:1393-1404 (2016).
Yagi, Haruhiko , et al., "Crucial role of FOXP3 in the development and function of human CD25+CD4+ regulatory T cells", International Immunology 16(11):1643-1656 (Oct. 4, 2004).
Yu, et al., "Exopolysaccharide-Producing Bifidobacterium adolescentis Strains with Similar Adhesion Property Induce Differential Regulation of Inflammatory Immune Response in Treg/Th17 Axis of DSS-Colitis Mice", Nutrients 11(4):782 (Apr. 4, 2019) 21 pages.
Sood, et al., "Fecal Microbiota Transplantation for Ulcerative Colitis: An Evolving Therapy", Crohn's & Colitis 360 2(4):otaa067 (Oct. 2020) 7 pages.

* cited by examiner

SEQUENCE LISTING

<160> NUMBER OF SEQ ID NOS: 25

<210> SEQ ID NO 1
<211> LENGTH: 1524
<212> TYPE: DNA
<213> ORGANISM: Bifidobacterium adolescentis

<400> SEQUENCE: 1
tgtggagggt tcgattctgg ctcaggatga acgctggcgg cgtgcttaac acatgcaagt 60
cgaacgggat cccaggagct tgctcctggg tgagagtggc gaacgggtga gtaatgcgtg 120
accgacctgc cccatacacc ggaatagctc ctggaaacgg gtggtaatgc cggatgctcc 180
agttgaccgc atggtcctct gggaaagctt ttgcggtatg ggatggggtc gcgtcctatc 240
agcttgatgg cggggtaacg gcccaccatg gcttcgacgg gtagccggcc tgagagggcg 300
accggccaca ttgggactga gatacggccc agactcctac gggaggcagc agtggggaat 360
attgcacaat gggcgcaagc ctgatgcagc gacgccgcgt gcgggatgac ggccttcggg 420
ttgtaaaccg cttttgactg ggagcaagcc cttcggggtg agtgtacctt tcgaataagc 480
accggctaac tacgtgccag cagccgcggt aatacgtagg gtgcaagcgt tatccggaat 540
tattgggcgt aaagggctcg taggcggttc gtcgcgtccg gtgtgaaagt ccatcgctta 600
acggtggatc cgcgccgggt acgggcgggc ttgagtgcgg taggggagac tggaattccc 660
ggtgtaacgg tggaatgtgt agatatcggg aagaacacca atggcgaagg caggtctctg 720
ggccgtcact gacgctgagg agcgaaagcg tggggagcga acaggattag ataccctggt 780
agtccacgcc gtaaacggtg gatgctggat gtggggacca ttccacggtc tccgtgtcgg 840
agccaacgcg ttaagcatcc cgcctgggga gtacggccgc aaggctaaaa ctcaaagaaa 900
ttgacggggg cccgcacaag cggcggagca tgcggattaa ttcgatgcaa cgcgaagaac 960
cttacctggg cttgacatgt tcccgacagc cccagagatg gggcctccct tcggggcggg 1020
ttcacaggtg gtgcatggtc gtcgtcagct cgtgtcgtga gatgttgggt taagtcccgc 1080
aacgagcgca accctcgccc tgtgttgcca gcacgtcgtg gtgggaactc acgggggacc 1140
gccggggtca actcggagga aggtggggat gacgtcagat catcatgccc cttacgtcca 1200
gggcttcacg catgctacaa tggccggtac aacgggatgc gacaccgcga ggtggagcgg 1260
atcccttaaa accggtctca gttcggattg gagtctgcaa cccgactcca tgaaggcgga 1320
gtcgctagta atcgcggatc agcaacgccg cggtgaatgc gttcccgggc cttgtacaca 1380
ccgcccgtca agtcatgaaa gtgggtagca cccgaagccg gtggcccaac cttttggggg 1440
gagccgtcta aggtgagact cgtgattggg actaagtcgt aacaaggtag ccgtaccgga 1500
aggtgcggct ggatcacctc cttt 1524

<210> SEQ ID NO 2
<211> LENGTH: 1517
<212> TYPE: DNA
<213> ORGANISM: Christensenellaceae R-7 Sp.

<400> SEQUENCE: 2
aagagtttga tcctggctca ggacgaacgc tggcggcgtg cctaacacat gcaagtcgag 60
cggagacagt gagtagcttg ctactgattg ttttagcggc ggacgggtga gtaacgcgtg 120
agcaaccttt cccagacagg ggaataacac accgaaaggt gtactaatac cgcataagac 180
cacgggatca catggttctg gggtaaaaga attatcggtt tggggtgggc tcgcgtccga 240
ttaggtagtt ggtgaggtaa cggcccacca agccgacgat cggtagccga cctgagaggg 300
tgatcggcca cattgggact gagacacggc ccaaactcct acgggaggca gcagtgggga 360
atattgggca atggaggaaa ctctgaccca gcaacgccgc gtggaggaag aaggttttcg 420
gatcgtaaac tcctgtcctt ggagacgagt agaagacggt atccaaggag gaagccccgg 480
ctaactacgt gccagcagcc gcggtaatac gtagggggca agcgttgtcc ggaataattg 540
ggcgtaaagg gcgcgtaggc ggctcggtaa gtctggagtg aaagtcctgc ttttaaggtg 600
ggaattgctt tggatactgt cgggcttgag tgcaggagag gttagtggaa ttcccagtgt 660
agcggtgaaa tgcgtagaga ttgggaggaa caccagtggc gaaggcgact aactggactg 720
taactgacgc tgaggcgcga aagtgtgggg agcaaacagg attagatacc ctggtagtcc 780
acactgtaaa cgatgaatgc taggtgtagg gggtatcgac cccttctgtg ccgcagtcaa 840
cacaataagc attccgcctg gggagtacgg ccgcaaggtt gaaactcaaa ggaattgacg 900
ggggcccgca caagcagcgg agcatgtggt ttaattcgac gcaacgcgaa gaaccttacc 960
aggtcttgac atccacttaa acttacagag atgtaaggtg tgcttgcaca aagtgagaca 1020
ggtggtgcat ggttgtcgtc agctcgtgtc gtgagatgtt gggttaagtc ccgcaacgag 1080
cgcaaccctt atcttcagtt actaacgcgt agaggtgagg actctgaaga gactgccggg 1140
gacaactcgg aggaaggtgg ggacgacgtc aaatcatcat gccccttatg acctgggcta 1200
cacacgtgct acaatggcca cgacagagag aagcgaaatc gtaaggtgga gcggaactca 1260
aaaaagtggt cccagttcgg attgtgggct gcaacccgcc cacatgaagt cggagttgct 1320
agtaatcgcg gatcagcatg ccgcggtgaa tacgttcccg ggccttgtac acaccgcccg 1380
tcacaccatg ggagttggga gtgcccaaag ccggtgaggc aaccgcaagg agccagccgt 1440
ctaaggcaag accaatgact ggggtgaagt cgtaacaagg tagccgtatc ggaaggtgcg 1500
gctggatcac ctcc tt t 1517

<210> SEQ ID NO 3
<211> LENGTH: 1509
<212> TYPE: DNA
<213> ORGANISM: Senegalimassilia anaerobia

<400> SEQUENCE: 3
acggagagtt tgatcctggc tcaggatgaa cgctggcggc gtgcctaaca catgcaagtc 60
gaacgatgaa accgccctcg ggcggacatg aagtggcgaa cgggtgagta acacgtgacc 120
gacctgcccc ccgcccaggg acagcccccc gaaaggggga ttaatacctg gtactccgga 180
agcggcgcat gccgcatccg ggaaagctta tcgcggcggg ggatggggtc gcggcccatc 240
aggtagacgg cggggcgacg gcccaccgtg ccgacgacgg gtagccgggt tgagagaccg 300

```
accggccaca ttgggactga gatacggccc agactcctac gggaggcagc agtggggaat    360
tttgcgcaat gggggcaacc ctgacgcagc aacgccgcgt gcgggacgaa ggcgtccgcg    420
tcgtaaaccg ctttcagcgg ggaacactta tcgagggtac ccgcagaaga agccccggct    480
aaatacgtgc cagcagccgc ggtaatacgt atggggcgag cgttatccgg attcattggg    540
cgtaaagcgc gcgtaggcgg agcgctaagc gggacctcta acccgagggc tcaacccccg    600
gccgggtccc gaactggcgc tctcgagtgc ggtaggggag agcggaattc ccggtgtagc    660
ggtggaatgc gcagatatcg ggaagaacac cgacggcgaa ggcagctctc tgggccgaaa    720
ctgacgctga ggcgcgaaag ctgggggagc gaacaggatt agataccctg gtagtcccag    780
ccgtaaacga tgggcgctag gtgtgggggg gaagaccccc cgtgccgcag ccaacgcatt    840
aagcgccccg cctggggagt acggccgcaa ggctaaaact caaaggaatt gacgggggcc    900
cgcacaagca gcggagcatg tggcttaatt cgaagcaacg cgaagaacct taccagggct    960
tgacatgcgg gtgaagcggc ggagacgccg tggccgagag gagcccgcac aggtggtgca   1020
tggctgtcgt cagctcgtgt cgtgagatgt tgggttaagt cccgcaacga gcgcaacccc   1080
tgccccgtgt tgccagcatt cagttgggga ctcgcggggg actgccggcg tcaagccgga   1140
ggaaggtggg gacgacgtca agtcatcatg ccccttatgc cctgggccgc acacgtgcta   1200
caatggccgg tacagagggt tgcgaccccg cgagggggag cggatcccgc aaagccggcc   1260
ccagttcgga tcggaggctg caacccgcct ccgtgaagcc ggagttgcta gtaatcgcgg   1320
atcagcacgc cgcggtgaat acgttcccgg gccttgtaca caccgcccgt cacaccaccc   1380
gagtcgtctg cacccgaagc cgccggccga accctttcag ggcggaggcc gtcgaaggtg   1440
tggagggtga ggggggtgaa gtcgtaacaa ggtagccgta ccggaaggtg cggctggatc   1500
acctccttt                                                           1509
```

```
<210> SEQ ID NO 4
<211> LENGTH: 1529
<212> TYPE: DNA
<213> ORGANISM: Prevotella copri

<400> SEQUENCE: 4

atggagagtt tgatcctggc tcaggatgaa cgctagctac aggcttaaca catgcaagtc     60
gaggggaaac gacatcgaaa gcttgctttt gatgggcgtc gaccggcgca cgggtgagta    120
acgcgtatcc aacctgccca ccacttgggg ataaccttgc gaaagtaaga ctaataccca    180
atgatatctc tagaagacat ctgaaagaga ttaaagattt atcggtgatg gatggggatg    240
cgtctgatta gcttgttggc ggggtaacgg cccaccaagg cgacgatcag taggggttct    300
gagaggaagg tcccccacat tggaactgag acacggtcca aactcctacg ggaggcagca    360
gtgaggaata ttggtcaatg gacgagagtc tgaaccagcc aagtagcgtg caggatgacg    420
gccctatggg ttgtaaactg cttttataag ggaataaagt gagtctcgtg agacttttttg    480
catgtacctt atgaataagg accggctaat tccgtgccag cagccgcggt aatacggaag    540
gtccgggcgt tatccggatt tattgggttt aaagggagcg taggccggag attaagcgtg    600
ttgtgaaatg tagacgctca acgtctgcac tgcagcgcga actggtttcc ttgagtacgc    660
acaaagtggg cggaattcgt ggtgtagcgg tgaaatgctt agatatcacg aagaactccg    720
attgcgaagg cagctcactg gagcgcaact gacgctgaag ctcgaaagtg cgggtatcga    780
acaggattag ataccctggt agtccgcacg gtaaacgatg gatgcccgct gttggtctga    840
```

```
ataggtcagc ggccaagcga aagcattaag catcccacct ggggagtacg ccggcaacgg    900

tgaaactcaa aggaattgac gggggcccgc acaagcggag gaacatgtgg tttaattcga    960

tgatacgcga ggaaccttac ccgggcttga attgcagagg aaggatttgg agacaatgac   1020

gcccttcggg gcctctgtga aggtgctgca tggttgtcgt cagctcgtgc cgtgaggtgt   1080

cggcttaagt gccataacga gcgcaacccc tctccttagt tgccatcagg tcacgctggg   1140

cactctgggg acactgccac cgtaaggtgt gaggaaggtg gggatgacgt caaatcagca   1200

cggcccttac gtccggggct acacacgtgt tacaatggca ggtacagaga gatggtccct   1260

tgcaaaatgg atcaaatcct taaagcctgt ctcagttcgg actggggtct gcaacccgac   1320

cccacgaagc tggattcgct agtaatcgcg catcagccat ggcgcggtga atacgttccc   1380

gggccttgta cacaccgccc gtcaagccat gaaagccggg ggcgcctaaa gtccgtgacc   1440

gtaaggagcg gcctagggcg aaactggtaa ttggggctaa gtcgtaacaa ggtagccgta   1500

ccggaaggtg cggctggaac acctccttt                                     1529
```

```
<210> SEQ ID NO 5
<211> LENGTH: 1526
<212> TYPE: DNA
<213> ORGANISM: Bifidobacterium pseudocatenulatum

<400> SEQUENCE: 5

tgtggagggt tcgattctgg ctcaggatga acgctggcgg cgtgcttaac acatgcaagt     60

cgaacgggat ccatcaggct ttgcttggtg gtgagagtgg cgaacgggtg agtaatgcgt    120

gaccgacctg ccccatacac cggaatagct cctggaaacg ggtggtaatg ccggatgctc    180

cgactcctcg catggggtgt cgggaaagat ttcatcggta tgggatgggg tcgcgtccta    240

tcaggtagtc ggcggggtaa cggcccaccg agcctacgac gggtagccgg cctgagaggg    300

cgaccggcca cattgggact gagatacggc ccagactcct acgggaggca gcagtgggga    360

atattgcaca atgggcgcaa gcctgatgca gcgacgccgc gtgcgggatg acggccttcg    420

ggttgtaaac cgcttttgat cgggagcaag ccttcgggtg agtgtacctt tcgaataagc    480

accggctaac tacgtgccag cagccgcggt aatacgtagg gtgcaagcgt tatccggaat    540

tattgggcgt aaagggctcg taggcggttc gtcgcgtccg gtgtgaaagt ccatcgctta    600

acggtggatc tgcgccgggt acgggcgggc tggagtgcgg taggggagac tggaattccc    660

ggtgtaacgg tggaatgtgt agatatcggg aagaacacca atggcgaagg caggtctctg    720

ggccgttact gacgctgagg agcgaaagcg tggggagcga acaggattag ataccctggt    780

agtccacgcc gtaaacggtg gatgctggat gtggggcccg ttccacgggt tccgtgtcgg    840

agctaacgcg ttaagcatcc cgcctgggga gtacggccgc aaggctaaaa ctcaaagaaa    900

ttgacggggg cccgcacaag cggcggagca tgcggattaa ttcgatgcaa cgcgaagaac    960

cttacctggg cttgacatgt tcccgaccgc ggcagagatg tcgtttccct tcggggcggg   1020

ttcacaggtg gtgcatggtc gtcgtcagct cgtgtcgtga gatgttgggt taagtcccgc   1080

aacgagcgca accctcgccc tgtgttgcca gcacgtcatg gtgggaactc acgggggacc   1140

gccggggtca actcggagga aggtggggat gacgtcagat catcatgccc cttacgtcca   1200

gggcttcacg catgctacaa tggccggtac aacgggatgc gacacggcga cgtggagcgg   1260

atccctgaaa accggtctca gttcggattg gagtctgcaa cccgactcca tgaaggcgga   1320

gtcgctagta atcgcggatc agcaacgccg cggtgaatgc gttcccgggc cttgtacaca   1380

ccgcccgtca agtcatgaaa gtgggtagca cccgaagccg gtggcctaac cctttgtgga   1440
```

tggagccgtc taaggtgaga ctcgtgattg ggactaagtc gtaacaaggt agccgtaccg 1500
gaaggtgcgg ctggatcacc tccttt 1526

<210> SEQ ID NO 6
<211> LENGTH: 1474
<212> TYPE: DNA
<213> ORGANISM: Eubacterium ventriosum

<400> SEQUENCE: 6
aacgagagtt tgatcctggc tcaggatgaa cgctggcggc gtgcttaata catgcaagtc 60
gaacgaagca ccttggacag aatccttcgg gaggaagacc attgtgactg agtggcggac 120
gggtgagtaa cgcgtgggta acctgccttg tacaggggga taacagttgg aaacgactgc 180
taataccgca taagcgcaca gtaccgcatg gtacggtgtg aaaaactccg gtggtacaag 240
atggacccgc gtctgattag ctagttggtg aggtaacggc ccaccaaggc gacgatcagt 300
agccgacttg agagagtgat cggccacatt gggactgaga cacggcccaa actcctacgg 360
gaggcagcag tagggaatat tgcacaatgg gggaaaccct gatgcagcga cgccgcgtga 420
aggaagaagt atttcggtat gtaaacttct atcagcaagg aagaaaatga cggtacttga 480
ctaagaagcc ccggctaaat acgtgccagc agccgcggta atacgtatgg ggcaagcgtt 540
atccggattt actgggtgta aagggagcgt aggcggcatg gcaagtcaga agtgaaagcc 600
tggggctcaa ccccggaatt gcttttgaaa ctgtcaggct agagtgtcgg aggggtaagc 660
ggaattccta gtgtagcggt gaaatgcgta gatattagga ggaacaccgg tggcgaaggc 720
ggcttactgg acgattactg acgctgaggc tcgaaagcgt ggggagcaaa caggattaga 780
taccctggta gtccacgccg taaacgatga atactaggtg tcgggggaca atagttcctc 840
ggtgccgaag caaacgcatt aagtattcca cctggggagt acgttcgcaa gaatgaaact 900
caaaggaatt gacggggacc cgcacaagcg gtggagcatg tggtttaatt cgaagcaacg 960
cgaagaacct tacctgctct tgacatccca ctgacaggtc agtaatgtga ccctttcttc 1020
ggaacagtgg agacaggtgg tgcatggttg tcgtcagctc gtgtcgtgag atgttgggtt 1080
aagtcccgca acgagcgcaa cccttgtctt tagtagccag cagtacggct gggcactcta 1140
gagagactgc cagggataac ctggaggaag gcggggatga cgtcaaatca tcatgcccct 1200
tacgagcagg gctacacacg tgctacaatg gcgtaaacaa agggaagcga ccccgtgagg 1260
gtaagcaaat ctcaaaaata acgtctcagt tcggattgta gtctgcaact cgactacatg 1320
aagctggaat cgctagtaat cgcgaatcag aatgtcgcgg tgaatacgtt cccgggtctt 1380
gtacacaccg cccgtcacac catgggagtt ggatatgccc gaagtcagtg acccaaccgt 1440
aaggagggag ctgccgaagg tggagccgat aact 1474

<210> SEQ ID NO 7
<211> LENGTH: 1528
<212> TYPE: DNA
<213> ORGANISM: Barnesiella intestinihominis

<400> SEQUENCE: 7
cgaagagttt gatcctggct caggatgaac gctagcgaca ggcctaacac atgcaagtcg 60
aggggcagcg gagaggtagc aataccttg ccggcgaccg gcgcacgggt gagtaacacg 120
tatgcaatcc acctgtaaca gggggataac ccggagaaat ccggactaat accccataat 180
atgggcgctc cgcatggaga gtccattaaa gagagcaatt ttggttacag acgagcatgc 240
gctccattag ccagttggcg gggtaacggc ccaccaaagc gacgatggat aggggttctg 300
agaggaaggt cccccacatt ggaactgaga cacggtccaa actcctacgg gaggcagcag 360
tgaggaatat tggtcaatgg tcggcagact gaaccagcca agtcgcgtga gggaagacgg 420
ccctacgggt tgtaaacctc ttttgtcgga gagtaaagta cgctacgtgt agtgtattgc 480
aagtatccga agaaaaagca tcggctaact ccgtgccagc agccgcggta atacggagga 540
tgcgagcgtt atccggattt attgggttta aagggtgcgt aggcggcacg ccaagtcagc 600
ggtgaaattt ccgggctcaa cccggactgt gccgttgaaa ctggcgagct agagtgcaca 660
agaggcaggc ggaatgcgtg gtgtagcggt gaaatgcata gatatcacgc agaaccccga 720
ttgcgaaggc agcctgctag ggtgcgacag acgctgaggc acgaaagcgt gggtatcgaa 780
caggattaga taccctggta gtccacgcag taaacgatga atactaactg tttgcgatac 840
aatgtaagcg gtacagcgaa agcgttaagt attccacctg gggagtacgc cggcaacggt 900
gaaactcaaa ggaattgacg gggcccgca caagcggagg aacatgtggt ttaattcgat 960
gatacgcgag gaaccttacc cggctcaaa cgcaggggga atgccggtga aagtcggcag 1020
ctagcaatag tcacctgcga ggtgctgcat ggttgtcgtc agctcgtgcc gtgaggtgtc 1080
ggcttaagtg ccataacgag cgcaacccct atggacagtt actaacgggt gaagccgagg 1140
actctgtcta gactgccggc gcaagccgcg aggaaggtgg ggatgacgtc aaatcagcac 1200
ggcccttacg tccggggcga cacacgtgtt acaatggcag gtacagaagg cagccagtca 1260
gcaatgacgc gcgaatcccg aaaacctgtc tcagttcgga ttggagtctg caacccgact 1320
ccatgaagct ggattcgcta gtaatcgcgc atcagccatg gcgcggtgaa tacgttcccg 1380
ggccttgtac acaccgcccg tcaagccatg gaagccggga gtacctgaag catgcaaccg 1440
caaggagcgt acgaaggtaa taccggtaac tggggctaag tcgtaacaag gtagccgtac 1500
cggaaggtgc ggctggaaca cctccttt 1528

<210> SEQ ID NO 8
<211> LENGTH: 1523
<212> TYPE: DNA
<213> ORGANISM: Bacteroides stercoris

<400> SEQUENCE: 8
atgaagagtt tgatcctggc tcaggatgaa cgctagctat aggcttaaca catgcaagtc 60
gaggggcagc atcatcaaag cttgctttga tggatggcga ccggcgcacg ggtgagtaac 120
acgtatccaa cctgccgaca actctgggat agcctttcga aagaaagatt aataccggat 180
ggcatagttt tcccgcatgg gttgactatt aaagaatttc ggttgtcgat ggggatgcgt 240
tccattaggc agttggcggg gtaacggccc accaaaccga cgatggatag ggttctgag 300 aggaaggtcc cccacattgg aactgagaca cggtccaaac tcctacggga ggcagcagtg 360
aggaatattg gtcaatggac gagagtctga accagccaag tagcgtgaag gatgactgcc 420
ctatgggttg taaacttctt ttatacggga ataaagttag ccacgtgtgg ctttttgtat 480
gtaccgtatg aataaggatc ggctaactcc gtgccagcag ccgcggtaat acggaggatc 540
cgagcgttat ccggatttat tgggtttaaa gggagcgtag gcgggttgtt aagtcagttg 600
tgaaagtttg cggctcaacc gtaaaattgc agttgatact ggcgaccttg agtgcaacag 660
aggtaggcgg aattcgtggt gtagcggtga aatgcttaga tatcacgaag aactccgatt 720
gcgaaggcag cttactggat tgtaactgac gctgatgctc gaaagtgtgg gtatcaaaca 780
ggattagata ccctggtagt ccacacagta aacgatgaat actcgctgtt ggcgatatac 840

```
tgtcagcggc caagcgaaag cattaagtat tccacctggg gagtacgccg gcaacggtga     900
aactcaaagg aattgacggg ggcccgcaca agcggaggaa catgtggttt aattcgatga     960
tacgcgagga accttacccg ggcttaaatt gcaactgacg gaatcggaaa cggttctttc    1020
ttcggacagt tgtgaaggtg ctgcatggtt gtcgtcagct cgtgccgtga ggtgtcggct    1080
taagtgccat aacgagcgca acccttatcg atagttacta gcaggtcatg ctgaggactc    1140
tatcgagact gccgtcgtaa gatgtgagga aggtggggat gacgtcaaat cagcacggcc    1200
cttacgtccg ggctacacac cgtgttacaa tgggggggtac agaaggcagc tacacggcga    1260
cgtggtgcta atcccgaaag cctctctcag ttcggattgg agtctgcaac ccgactccat    1320
gaagctggat tcgctagtaa tcgcgcatca gccacggcgc ggtgaatacg ttcccgggcc    1380
ttgtacacac cgcccgtcaa gccatgaaag ccgggggtac ctgaagtacg taaccgcgag    1440
gagcgtccta gggtaaaact ggtgattggg gctaagtcgt aacaaggtag ccgtaccgga    1500
aggtgcggct ggaacacctc ctt                                            1523
```

<210> SEQ ID NO 9
<211> LENGTH: 1530
<212> TYPE: DNA
<213> ORGANISM: Roseburia faecis

<400> SEQUENCE: 9

```
atgagagttt gatcctggct caggatgaac gctggcggcg tgcttaacac atgcaagtcg      60
aacgaagcac tctatttgat ttctttcgga aatgaagatt ttgtgactga gtggcggacg     120
ggtgagtaac gcgtgggtaa cctgcctcat acagggggat aacagttgga aacgactgct     180
aataccgcat aagcgcacag gatcgcatga tccggtgtga aaaactccgg tggtatggga     240
tggacccgcg tctgattagc cagttggcag ggtaacggcc taccaaagcg acgatcagta     300
gccgacctga gagggtgacc ggccacattg ggactgagac acggcccaaa ctcctacggg     360
aggcagcagt ggggaatatt gcacaatggg ggaaaccctg atgcagcgac gccgcgtgag     420
cgaagaagta tttcggtatg taaagctcta tcagcaggga agaagaatga cggtacctga     480
ctaagaagca ccggctaaat acgtgccagc agccgcggta atacgtatgg tgcaagcgtt     540
atccggattt actgggtgta aagggagcgc aggcggtgcg gcaagtctga tgtgaaagcc     600
cggggctcaa ccccggtact gcattggaaa ctgtcgtact agagtgtcgg aggggtaagt     660
ggaattccta gtgtagcggt gaaatgcgta gatattagga ggaacaccag tggcgaaggc     720
ggcttactgg acgataactg acgctgaggc tcgaaagcgt ggggagcaaa caggattaga     780
taccctggta gtccacgccg taaacgatga atactaggtg tcggggagca ttgctcttcg     840
gtgccgcagc aaacgcaata agtattccac ctggggagta cgttcgcaag aatgaaactc     900
aaaggaattg acggggaccc gcacaagcgg tggagcatgt ggtttaattc gaagcaacgc     960
gaagaacctt accaagtctt gacatcccga tgacaagcta tgtaatgtag cctctcttcg    1020
gagcatcggt gacaggtggt gcatggttgt cgtcagctcg tgtcgtgaga tgttgggtta    1080
agtcccgcaa cgagcgcaac ccctgttctt agtagccagc ggttcggccg ggcactctag    1140
ggagactgcc agggataacc tggaggaagg cggggatgac gtcaaatcat catgcccctt    1200
atgacttggg ctacacacgt gctacaatgg cgtaaacaaa gggaagcgga gccgtgaggc    1260
cgagcaaatc tcaaaaataa cgtctcagtt cggactgtag tctgcaaccc gactacacga    1320
agctggaatc gctagtaatc gcagatcaga atgctgcggt gaatacgttc ccgggtcttg    1380
```

```
tacacaccgc ccgtcacacc atgggagttg gaaatgcccg aagtcagtga cccaaccgca   1440

aggagggagc tgccgaaggc aggttcgata actggggtga agtcgtaaca aggtagccgt   1500

atcggaaggt gcggctggat cacctccttt                                    1530
```

<210> SEQ ID NO 10
<211> LENGTH: 1508
<212> TYPE: DNA
<213> ORGANISM: Slackia isoflavoniconvertans

<400> SEQUENCE: 10

```
cggagagttt gatcctggct caggatgaac gctggcggcg cgcctaacac atgcaagtcg     60

aacgagtaag acgccttcgg gcgtggatag agtggcgaac gggtgagtaa cacgtgacca    120

acctgccccc tcctccggga caacctcggg aaaccgaggc taataccgga tactccgggc    180

cccccgcatg gggggcccgg gaaagccctg gcgggagggg atggggtcgc ggcccatcag    240

gtagacggcg gggtaacggc ccaccgtgcc tgcaacgggt agccgggctg agaggccgat    300

cggccacatt gggactgaga cacggcccag actcctacgg gaggcagcag tggggaattt    360

tgcgcaatgg gggcaaccct gacgcagcga cgccgcgtgc gggacgaagt cattcgtgac    420

gtaaaccgct ttcagcgagg aagaaccatg acggtactcg cagaagaagc cccggctaac    480

tacgtgccag cagccgcggt aatacgtagg gggcgagcgt tatccggaat cattgggcgt    540

aaagcgcgcg caggcgggct ttcaagcggc ggcgtcgaag ccgggggctc aacccccgga    600

agcgccccga actggaagcc tcggatgcgg caggggggagg cggaattccc ggtgtagcgg   660

tgaaatgcgc agatatcggg aagaacaccg acggcgaagg cagcctcctg ggccggcatc    720

gacgctgagg cgcgaaagct gggggagcga acaggattag ataccctggt agtcccagcc    780

gtaaacgatg gacgctaggt gtgggggat aggtccctcc gtgccgaagc caacgcatta     840

agcgtcccgc ctggggagta cggccgcaag gctaaaactc aaaggaattg acgggggccc    900

gcacaagcag cggagcatgt ggcttaattc gaagcaacgc gaagaacctt accagggctt    960

gacatatcgg tgaagccgga gagatccggt ggccgagagg agccgataca ggtggtgcat   1020

ggctgtcgtc agctcgtgcc gtgaggtgtt gggttaagtc ccgcaacgag cgcaaccccc   1080

gccgcgtgtt gccagcattc agttgggcac tcacgcggga ctgccggcgt caagccggag   1140

gaaggcgggg acgacgtcaa gtcatcatgc ccctcatgcc ctgggccgca cacgtgctac   1200

aatggccggc acaacgggtt gccacccgc gagggggagc ggatccccaa agccggcccc    1260

agttcggatc gcaggctgca acccgcctgc gtgaagccgg agttgctagt aatcgcggat   1320

cagcacgccg cggtgaatac gttcccgggc cttgtacaca ccgcccgtca caccacccga   1380

gtcgtctgca cccgaagccg ccggccgaac ccctccgggg ggcggaggcg tcgaaggtgt   1440

ggagggtgag gggggtgaag tcgtaacaag gtagccgtac cggaaggtgc ggctggatca   1500

cctccttt                                                            1508
```

<210> SEQ ID NO 11
<211> LENGTH: 1525
<212> TYPE: DNA
<213> ORGANISM: Bifidobacterium adolescentis

<400> SEQUENCE: 11

```
tgtggagggt tcgattctgg ctcaggatga acgctggcgg cgtgcttaac acatgcaagt     60

cgaacgggat cccaggagct tgctcctggg tgagagtggc gaacgggtga gtaatgcgtg    120

accgacctgc cccatacacc ggaatagctc ctggaaacgg gtggtaatgc cggatgctcc    180
```

agttgaccgc atggtcctct gggaaagctt ttgcggtatg ggatggggtc gcgtcctatc 240
agcttgatgg cggggtaacg gcccaccatg gcttcgacgg gtagccggcc tgagagggcg 300
accggccaca ttgggactga gatacggccc agactcctac gggaggcagc agtggggaat 360
attgcacaat gggcgcaagc ctgatgcagc gacgccgcgt gcgggatgac ggccttcggg 420
ttgtaaaccg cttttgactg ggagcaagcc cttcggggtg agtgtacctt tcgaataagc 480
accggctaac tacgtgccag cagccgcggt aatacgtagg gtgcaagcgt tatccggaat 540
tattgggcgt aaagggctcg taggcggttc gtcgcgtccg gtgtgaaagt ccatcgctta 600
acggtggatc cgcgccgggt acgggcgggc ttgagtgcgg taggggagac tggaattccc 660
ggtgtaacgg tggaatgtgt agatatcggg aagaacacca atggcgaagg caggtctctg 720
ggccgtcact gacgctgagg agcgaaagcg tggggagcga acaggattag ataccctggt 780
agtccacgcc gtaaacggtg gatgctggat gtggggacca ttccacggtc tccgtgtcgg 840
agccaacgcg ttaagcatcc cgcctgggga gtacggccgc aaggctaaaa ctcaaagaaa 900
ttgacggggg cccgcacaag cggcggagca tgcggattaa ttcgatgcaa cgcgaagaac 960
cttacctggg cttgacatgt tcccgacagc cccagagatg gggcctccct tcggggcggg 1020
ttcacaggtg gtgcatggtc gtcgtcagct cgtgtcgtga gatgttgggt taagtcccgc 1080
aacgagcgca accctcgccc tgtgttgcca gcacgtcgtg gtgggaactc acgggggacc 1140
gccggggtca actcggagga aggtggggat gacgtcagat catcatgccc cttacgtcca 1200
gggcttcacg catgctacaa tggccggtac aacgggatgc gacaccgcga ggtggagcgg 1260
atcccttaaa accggtctca gttcggattg gagtctgcaa cccgactcca tgaaggcgga 1320
gtcgctagta atcgcggatc agcaacgccg cggtgaatgc gttcccgggc cttgtacaca 1380
ccgcccgtca agtcatgaaa gtgggtagca cccgaagccg gtggcccaac ctttttgggg 1440
ggagccgtct aaggtgagac tcgtgattgg gactaagtcg taacaaggta gccgtaccgg 1500
aaggtgcggc tggatcacct ccttt 1525

<210> SEQ ID NO 12
<211> LENGTH: 1529
<212> TYPE: DNA
<213> ORGANISM: Prevotella copri

<400> SEQUENCE: 12
atggagagtt tgatcctggc tcaggatgaa cgctagctac aggcttaaca catgcaagtc 60
gaggggaaac gatattggaa gcttgcttcc gataggcgtc gaccggcgca cgggtgagta 120
acgcgtatcc aacctgccca ccacttgggg ataaccttgc gaaagtaaga ctaataccca 180
atgacgtctc tagaagacat ctgaaagaga ttaaagattt atcggtgatg gatggggatg 240
cgtctgatta gcttgttggc ggggtaacgg cccaccaagg caacgatcag taggggttct 300
gagaggaagg tcccccacat tggaactgag acacggtcca aactcctacg ggaggcagca 360
gtgaggaata ttggtcaatg gacgagagtc tgaaccagcc aagtagcgtg caggatgacg 420
gccctatggg ttgtaaactg cttttataag ggaataaagt gagtctcgtg agactttttg 480
catgtacctt atgaataagg accggctaat tccgtgccag cagccgcggt aatacggaag 540
gtccgggcgt tatccggatt tattgggttt aaagggagcg taggccggag attaagcgtg 600
ttgtgaaatg tagacgctca acgtctgcac tgcagcgcga actggtttcc ttgagtacgc 660
acaaagtggg cggaattcgt ggtgtagcgg tgaaatgctt agatatcacg aagaactccg 720

-continued

```
attgcgaagg cagctcactg gagcgcaact gacgctgaag ctcgaaagtg cgggtatcga    780

acaggattag ataccctggt agtccgcacg gtaaacgatg gatgcccgct gttggtctga    840

ataggtcagc ggccaagcga aagcattaag catcccacct ggggagtacg ccggcaacgg    900

tgaaactcaa aggaattgac gggggcccgc acaagcggag gaacatgtgg tttaattcga    960

tgatacgcga ggaaccttac ccgggcttga attgcagagg aaggatttgg agacaatgac   1020

gcccttcggg gcctctgtga aggtgctgca tggttgtcgt cagctcgtgc cgtgaggtgt   1080

cggcttaagt gccataacga gcgcaacccc tctccttagt tgccatcagg ttaagctggg   1140

cactctgggg acactgccac cgtaaggtgt gaggaaggtg gggatgacgt caaatcagca   1200

cggcccttac gtccggggct acacacgtgt tacaatggca ggtacagaga gacggtccct   1260

tgcaaaatgg atcaaatcct taaagcctgt ctcagttcgg actggggtct gcaacccgac   1320

cccacgaagc tggattcgct agtaatcgcg catcagccat ggcgcggtga atacgttccc   1380

gggccttgta cacaccgccc gtcaagccat gaaagccggg ggcgcctaaa gtccgtgacc   1440

gtaaggagcg gcctagggcg aaactggtaa ttggggctaa gtcgtaacaa ggtagccgta   1500

ccggaaggtg cggctggaac acctcctttt                                    1529
```

<210> SEQ ID NO 13
<211> LENGTH: 1530
<212> TYPE: DNA
<213> ORGANISM: Roseburia faecis

<400> SEQUENCE: 13

```
atgagagttt gatcctggct caggatgaac gctggcggcg tgcttaacac atgcaagtcg     60

aacgaagcac tctatttgat tttcttcgga aatgaagatt ttgtgactga gtggcggacg    120

ggtgagtaac gcgtgggtaa cctgcctcat acagggggat aacagttgga aacgactgct    180

aataccgcat aagcgcacag gatcgcatga tccggtgtga aaaactccgg tggtatggga    240

tggacccgcg tctgattagc cagttggcag ggtaacggcc taccaaagcg acgatcagta    300

gccgacctga gagggtgacc ggccacattg ggactgagac acggcccaaa ctcctacggg    360

aggcagcagt ggggaatatt gcacaatggg ggaaaccctg atgcagcgac gccgcgtgag    420

cgaagaagta tttcggtatg taaagctcta tcagcaggga agaagaatga cggtacctga    480

ctaagaagca ccggctaaat acgtgccagc agccgcggta atacgtatgg tgcaagcgtt    540

atccggattt actgggtgta aagggagcgc aggcggtgcg gcaagtctga tgtgaaagcc    600

cggggctcaa ccccggtact gcattggaaa ctgtcgtact agagtgtcgg aggggtaagt    660

ggaattccta gtgtagcggt gaaatgcgta gatattagga ggaacaccag tggcgaaggc    720

ggcttactgg acgataactg acgctgaggc tcgaaagcgt ggggagcaaa caggattaga    780

taccctggta gtccacgccg taaacgatga atactaggtg tcggggagca ttgctcttcg    840

gtgccgcagc aaacgcaata agtattccac ctggggagta cgttcgcaag aatgaaactc    900

aaaggaattg acggggaccc gcacaagcgg tggagcatgt ggtttaattc gaagcaacgc    960

gaagaacctt accaagtctt gacatcccga tgacagagta tgtaatgtac tttctcttcg   1020

gagcatcggt gacaggtggt gcatggttgt cgtcagctcg tgtcgtgaga tgttgggtta   1080

agtcccgcaa cgagcgcaac ccctgttctt agtagccagc ggtccggccg ggcactctag   1140

ggagactgcc agggataacc tggaggaagg cggggatgac gtcaaatcat catgcccctt   1200

atgacttggg ctacacacgt gctacaatgg cgtaaacaaa gggaagcgga gccgtgaggc   1260

cgagcaaatc tcaaaaataa cgtctcagtt cggactgtag tctgcaaccc gactacacga   1320
```

```
agctggaatc gctagtaatc gcagatcaga atgctgcggt gaatacgttc ccgggtcttg   1380

tacacaccgc ccgtcacacc atgggagttg gaaatgcccg aagtcagtga cccaaccgca   1440

aggagggagc tgccgaaggc aggttcgata actggggtga agtcgtaaca aggtagccgt   1500

atcggaaggt gcggctggat cacctccttt                                    1530
```

```
<210> SEQ ID NO 14
<211> LENGTH: 1517
<212> TYPE: DNA
<213> ORGANISM: Christensenellaceae R-7 Sp.

<400> SEQUENCE: 14

aagagtttga tcctggctca ggacgaacgc tggcggcgtg cctaacacat gcaagtcgag     60

cggagacagt gagtagcttg ctatgagctg ttttagcggc ggacgggtga gtaacgcgtg    120

agcaaccttt cccagacagg ggaataacac accgaaaggt gtactaatac cgcataagac    180

cacgggatca catggttctg gggtaaaaga tttatcggtt tggggtgggc tcgcgtccga    240

ttaggtagtt ggtgaggtaa cggcccacca agccgacgat cggtagccga cctgagaggg    300

tgatcggcca cattgggact gagacacggc ccaaactcct acgggaggca gcagtgggga    360

atattgggca atgggggaa ccctgaccca gcaacgccgc gtggaggaag aaggttttcg    420

gatcgtaaac tcctgtcctt ggagacgagt agaagacggt atccaaggag gaagccccgg    480

ctaactacgt gccagcagcc gcggtaatac gtagggggca agcgttgtcc ggaataattg    540

ggcgtaaagg gcgcgtaggc ggctcggtaa gtctggagtg aaagtcctgc ttttaaggtg    600

ggaattgctt tggatactgt cggcttgag tgcaggagag gttagtggaa ttcccagtgt    660

agcggtgaaa tgcgtagaga ttgggaggaa caccagtggc gaaggcgact aactggactg    720

taactgacgc tgaggcgcga aagtgtgggg agcaaacagg attagatacc ctggtagtcc    780

acactgtaaa cgatgaatgc taggtgtagg gggtatcgac cccttctgtg ccgcagttaa    840

cacaataagc attccgcctg gggagtacgg ccgcaaggtt gaaactcaaa ggaattgacg    900

ggggcccgca caagcagcgg agcatgtggt ttaattcgac gcaacgcgaa gaaccttacc    960

aggtcttgac atccagtaaa acttgtagag atacaaggtg agcttgctca tactgagaca   1020

ggtggtgcat ggttgtcgtc agctcgtgtc gtgagatgtt gggttaagtc ccgcaacgag   1080

cgcaaccctt atcttcagtt actaacgcgt agaggtgagg actctgaaga gactgccggg   1140

gacaactcgg aggaaggtgg ggacgacgtc aaatcatcat gccccttatg acctgggcta   1200

cacacgtgct acaatggcca cgacagagag aagcgaaatc gcaaggtaga gcggaactca   1260

aaaaagtggt cccagttcgg attgtgggct gcaacccgcc cacatgaagt cggagttgct   1320

agtaatcgcg gatcagcatg ccgcggtgaa tacgttcccg ggccttgtac acaccgcccg   1380

tcacaccatg ggagttggga gtgcccaaag ccggtgaggc aaccgcaagg agccagccgt   1440

ctaaggcaag accaatgact ggggtgaagt cgtaacaagg tagccgtatc ggaaggtgcg   1500

gctggatcac ctccttt                                                  1517
```

```
<210> SEQ ID NO 15
<211> LENGTH: 1529
<212> TYPE: DNA
<213> ORGANISM: Prevotella copri

<400> SEQUENCE: 15

atggagagtt tgatcctggc tcaggatgaa cgctagctac aggcttaaca catgcaagtc     60
```

```
gaggggaaac gacatcgaaa gcttgctttt gatgggcgtc gaccggcgca cgggtgagta    120
acgcgtatcc aacctgcccg ccacttgggg ataaccttgc gaaagtaaga ctaataccca    180
atgatatctc tagaaggcat ctgaaagaga ttaaagattt atcggtgatg gatggggatg    240
cgtctgatta gcttgttggc ggggtaacgg cccaccaagg caacgatcag taggggttct    300
gagaggaagg tcccccacat tggaactgag acacggtcca aactcctacg ggaggcagca    360
gtgaggaata ttggtcaatg gacgagagtc tgaaccagcc aagtagcgtg caggaagacg    420
gccctatggg ttgtaaactg cttttataag ggaataaagt gagtctcgtg agactttttg    480
catgtacctt atgaataagg accggctaat tccgtgccag cagccgcggt aatacggaag    540
gtccgggcgt tatccggatt tattgggttt aaagggagcg taggccggag attaagcgtg    600
ttgtgaaatg tagatgctca acatctgaac tgcagcgcga actggtttcc ttgagtacgc    660
acaaagtggg cggaattcgt ggtgtagcgg tgaaatgctt agatatcacg aagaactccg    720
attgcgaagg cagctcactg gagcgcaact gacgctgaag ctcgaaagtg cgggtatcga    780
acaggattag ataccctggt agtccgcacg gtaaacgatg gatgcccgct gttggtctga    840
ataggtcagc ggccaagcga aagcattaag catcccacct ggggagtacg ccggcaacgg    900
tgaaactcaa aggaattgac gggggcccgc acaagcggag gaacatgtgg tttaattcga    960
tgatacgcga ggaaccttac ccgggcttga attgcagagg aaggatttgg agacaatgac   1020
gcccttcggg gcctctgtga aggtgctgca tggttgtcgt cagctcgtgc cgtgaggtgt   1080
cggcttaagt gccataacga gcgcaacccc tctccttagt tgccatcagg tgaagctggg   1140
cactctgggg acactgccac cgtaaggtgt gaggaaggtg gggatgacgt caaatcagca   1200
cggcccttac gtccggggct acacacgtgt tacaatggca ggtacagaga gacggtccct   1260
tgcaaaatgg atcaaatcct taaagcctgt ctcagttcgg actggggtct gcaacccgac   1320
cccacgaagc tggattcgct agtaatcgcg catcagccat ggcgcggtga atacgttccc   1380
gggccttgta cacaccgccc gtcaagccat gaaagccggg ggcgcctaaa gtccgtgacc   1440
gtaaggagcg gcctagggcg aaactggtaa ttggggctaa gtcgtaacaa ggtagccgta   1500
ccggaaggtg cggctggaac acctcctttt                                    1529
```

```
<210> SEQ ID NO 16
<211> LENGTH: 1526
<212> TYPE: DNA
<213> ORGANISM: Bifidobacterium adolescentis
<220> FEATURE:
<221> NAME/KEY: misc_feature
<223> OTHER INFORMATION: R= A or G, S= G or C, Y= C or T

<400> SEQUENCE: 16

tgtggagggt tcgattctgg ctcaggatga acgctggcgg cgtgcttaac acatgcaagt     60
cgaacgggat cggctggagc ttgctccggc cgtgagagtg gcgaacgggt gagtaatgcg    120
tgaccgacct gccccataca ccggaatagc tcctggaaac gggtggtaat gccggatgct    180
ccagttggat gcatgtcctt ctgggaaaga ttcatcggta tgggatgggg tcgcgtccta    240
tcagcttgat ggcggggtaa cggcccacca tggcttcgac gggtagccgg cctgagaggg    300
cgaccggcca cattgggact gagatacggc ccagactcct acgggaggca gcagtgggga    360
atattgcaca atgggcgcaa gcctgatgca gcgacgccgc gtgcgggatg acggccttcg    420
ggttgtaaac cgcttttgac tgggagcaag cccttcgggg tgagtgtacc tttcgaataa    480
gcaccggcta actacgtgcc agcagccgcg gtaatacgta gggtgcaagc gttatccgga    540
```

```
attattgggc gtaaagggct cgtaggcggt tcgtcgcgtc cggtgtgaaa gtccatcgct    600

taacggtgga tccgcgccgg gtacgggcgg gcttgagtgc ggtaggggag actggaattc    660

ccggtgtaac ggtggaatgt gtagatatcg ggaagaacac caatggcgaa ggcaggtctc    720

tgggccgtca ctgacgctga ggagcgaaag cgtggggagc gaacaggatt agataccctg    780

gtagtccacg ccgtaaacgg tggatgctgg atgtggggac cattccacgg tctccgtgtc    840

ggagccaacg cgttaagcat cccgcctggg gagtacggcc gcaaggctaa aactcaaaga    900

aattgacggg ggcccgcaca agcggcggag catgcggatt aattcgatgc aacgcgaaga    960

accttacctg ggcttgacat gttcccgaca gccsyagaga trsggyctcc cttcggggcg   1020

ggttcacagg tggtgcatgg tcgtcgtcag ctcgtgtcgt gagatgttgg gttaagtccc   1080

gcaacgagcg caaccctcgc cctgtgttgc cagcacgtcg tggtgggaac tcacggggga   1140

ccgccggggt caactcggag gaaggtgggg atgacgtcag atcatcatgc cccttacgtc   1200

cagggcttca cgcatgctac aatggccggt acaacgggat gcgacaccgc gaggtggagc   1260

ggatccctta aaaccggtct cagttcggat tggagtctgc aacccgactc catgaaggcg   1320

gagtcgctag taatcgcgga tcagcaacgc cgcggtgaat gcgttcccgg gccttgtaca   1380

caccgcccgt caagtcatga aagtgggtag cacccgaagc cggtggccca accttttggg   1440

gggagccgtc taaggtgaga ctcgtgattg ggactaagtc gtaacaaggt agccgtaccg   1500

gaaggtgcgg ctggatcacc tccttt                                        1526


<210> SEQ ID NO 17
<211> LENGTH: 1107
<212> TYPE: DNA
<213> ORGANISM: Christensenellaceae R-7 Sp.
<220> FEATURE:
<221> NAME/KEY: misc_feature
<223> OTHER INFORMATION: R= A or G, W= A or T, Y= C or T, K= G or T

<400> SEQUENCE: 17

aagagtttga tcctggctca ggacgaacgc tggcggcgtg cctaacacat gcaagtcgag     60

cggagacagt gagtagcttg ctaygagctg ttttagcggc ggacgggtga gtaacgcgtg    120

agcaaccttt cccagacagg ggaataacac accgaaaggt gtactaatac cgcataagac    180

cacggkwtca catggkwctg rggtaaaaga tttatcggtt tggggtgggc tcgcgtccga    240

ttaggtagtt ggtgaggtaa cggcccacca agccgacgat cggtagccga cctgagaggg    300

tgatcggcca cattgggact gagacacggc ccaaactcct acgggaggca gcagtgggga    360

atattgggca atggrggraa cyctgaccca gcaacgccgc gtggaggaag aaggttttcg    420

gatcgtaaac tcctgtcctt ggagacgagt agaagacggt atccaaggag gaagccccgg    480

ctaactacgt gccagcagcc gcggtaatac gtagggggca agcgttgtcc ggaataattg    540

ggcgtaaagg gcgcgtaggc ggctcggtaa gtctggagtg aaagtcctgc ttttaaggtg    600

ggaattgctt tggatactgt cgggcttgag tgcaggagag gttagtggaa ttcccagtgt    660

agcggtgaaa tgcgtagaga ttgggaggaa caccagtggc gaaggcgact aactggactg    720

taactgacgc tgaggcgcga aagtgtgggg agcaaacagg attagatacc ctggtagtcc    780

acactgtaaa cgatgaatgc taggtgtagg gggtatcgac cccttctgtg ccgcagtcaa    840

cacaataagc attccgcctg gggagtacgg ccgcaaggtt gaaactcaaa ggaattgacg    900

ggggcccgca caagcagcgg agcatgtggt ttaattcgac gcaacgcgaa gaaccttacc    960

aggtcttgac atccacttaa acttacagag atgtaaggtg tgcttgcaca aagtgagaca   1020
```

ggtggtgcat ggttgtcgtc agctcgtgtc gtgagatgtt gggttaagtc ccgcaacgag 1080
cgcaaccctt atcttcagtt actaacg 1107

<210> SEQ ID NO 18
<211> LENGTH: 1509
<212> TYPE: DNA
<213> ORGANISM: Senegalimassilia anaerobia
<220> FEATURE:
<221> NAME/KEY: misc_feature
<223> OTHER INFORMATION: R= A or G, W= A or T, Y= C or T

<400> SEQUENCE: 18
acggagagtt tgatcctggc tcaggatgaa cgctggcggc gtgcctaaca catgcaagtc 60
gaacgatgaa accgccctcg ggcggacatg aagtggcgaa cgggtgagta acacgtgacc 120
gacctgcccc ccgcccaggg acagcccccc gaaaggggga ttaatacctg gtactccgga 180
agcggcgcat gccgtctccg ggaaagctta tcgcggcggg ggatggggtc gcggcccatc 240
aggtagacgg cggggcgacg gcccaccgtg ccgacgacgg gtagccgggt tgagagaccg 300
accggccaca ttgggactga gatacggccc agactcctac gggaggcagc agtggggaat 360
tttgcgcaat gggggcaacc ctgacgcagc aacgccgcgt gcgggacgaa ggcgtccgcg 420
tcgtaaaccg ctttcagcgg ggaacacttw tcgagggtac ccgcagaaga agccccggct 480
aaatacgtgc cagcagccgc ggtaatacgt atggggcgag cgttatccgg attcattggg 540
cgtaaagcgc gcgtaggcgg agcgctaagc gggacctcta acccgagggc tcaacccccg 600
gccgggtccc gaactggcgc tctcgagtgc ggtaggggag agcggaattc ccggtgtagc 660
ggtggaatgc gcagatatcg ggaagaacac cgacggcgaa ggcagctctc tgggccgaaa 720
ctgacgctga ggcgcgaaag ctgggggagc gaacaggatt agataccctg gtagtcccag 780
ccgtaaacga tgggcgctag gtgtgggggg gaagaccccc cgtgccgcag ccaacgcatt 840
aagcgccccg cctggggagt acggccgcaa ggctaaaact caaaggaatt gacgggggcc 900
cgcacaagca gcggagcatg tggcttaatt cgaagcaacg cgaagaacct taccagggct 960
tgacatryrg gtgaagcggc ggagacgccg tggccgagag gagcccgcac aggtggtgca 1020
tggctgtcgt cagctcgtgt cgtgagatgt tgggttaagt cccgcaacga gcgcaacccc 1080
tgccccgtgt tgccagcatt cagttgggga ctcgcggggg actgccggcg tcaagccgga 1140
ggaaggtggg gacgacgtca agtcatcatg ccccttatgc cctgggccgc acacgtgcta 1200
caatggccgg tacagagggt tgcgaccccg cgagggggag cggatcccgc aaagccggcc 1260
ccagttcgga tcggaggctg caacccgcct ccgtgaagcc ggagttgcta gtaatcgcgg 1320
atcagcacgc cgcggtgaat acgttcccgg gccttgtaca caccgcccgt cacaccaccc 1380
gagtcgtctg cacccgaagc cgccggccga accctttcag ggcggaggc gtcgaaggtg 1440 tggagggtga ggggggtgaa gtcgtaacaa ggtagccgta ccggaaggtg cggctggatc 1500
acctccttt 1509

<210> SEQ ID NO 19
<211> LENGTH: 1529
<212> TYPE: DNA
<213> ORGANISM: Prevotella copri
<220> FEATURE:
<221> NAME/KEY: misc_feature
<223> OTHER INFORMATION: R= A or G, S=G or C, W= A or T, Y= C or T, M= A
or C

<400> SEQUENCE: 19

```
atggagagtt tgatcctggc tcaggatgaa cgctagctac aggcttaaca catgcaagtc     60

gaggggaaac gayatygraa gcttgcttyy gatrggcgtc gaccggcgca cgggtgagta    120

acgcgtatcc aacctgccca ycacttgggg ataaccttgc gaaagtaaga ctaataccca    180

atgayrtctc tagaagacat ctgaaagaga ttaaagatty atcggtgatg gatggggatg    240

cgtctgatta gcttgttggc ggggtaacgg cccaccaagg cracgatcag taggggttct    300

gagaggaagg tcccccacat tggaactgag acacggtcca aactcctacg ggaggcagca    360

gtgaggaata ttggtcaatg gacgagagtc tgaaccagcc aagtagcgtg caggawgacg    420

gccctatggg ttgtaaactg cttttataag ggaataaagt gagwstcgtg aswctttttg    480

catgtacctt atgaataagg accggctaat tccgtgccag cagccgcggt aatacggaag    540

gtccgggcgt tatccggatt tattgggttt aaagggagcg taggccggag attaagcgtg    600

ttgtgaaatg tagaygctca acrtctgmac tgcagcgcga actggtttcc ttgagtacgc    660

acaaagtggg cggaattcgt ggtgtagcgg tgaaatgctt agatatcacg aagaactccg    720

attgcgaagg cagctcactg gagcgcaact gacgctgaag ctcgaaagtg cgggtatcga    780

acaggattag ataccctggt agtccgcacg gtaaacgatg gatgcccgct gttggtctga    840

ataggtcagc ggccaagcga aagcattaag catcccacct ggggagtacg ccggcaacgg    900

tgaaactcaa aggaattgac gggggcccgc acaagcggag gaacatgtgg tttaattcga    960

tgatacgcga ggaaccttac ccgggcttga attgcagagg aaggatttgg agacaatgac   1020

gcccttcggg gcctctgtga aggtgctgca tggttgtcgt cagctcgtgc cgtgaggtgt   1080

cggcttaagt gccataacga gcgcaacccc tctccttagt tgccatcagg tyawgctggg   1140

cactctgggg acactgccac cgtaaggtgt gaggaaggtg gggatgacgt caaatcagca   1200

cggcccttac gtccggggct acacacgtgt tacaatggca ggtacagaga gacggtccct   1260

tgcaaaatgg atcaaatcct taaagcctgt ctcagttcgg actggggtct gcaacccgac   1320

cccacgaagc tggattcgct agtaatcgcg catcagccat ggcgcggtga atacgttccc   1380

gggccttgta cacaccgccc gtcaagccat gaaagccggg ggcgcctaaa gtccgtgacc   1440

gtaaggagcg gcctagggcg aaactggtaa ttggggctaa gtcgtaacaa ggtagccgta   1500

ccggaaggtg cggctggaac acctcctttt                                    1529
```

<210> SEQ ID NO 20
<211> LENGTH: 1526
<212> TYPE: DNA
<213> ORGANISM: Bifidobacterium pseudocatenulatum

<400> SEQUENCE: 20

```
tgtggagggt tcgattctgg ctcaggatga acgctggcgg cgtgcttaac acatgcaagt     60

cgaacgggat ccatcaggct ttgcttggtg gtgagagtgg cgaacgggtg agtaatgcgt    120

gaccgacctg ccccatacac cggaatagct cctggaaacg ggtggtaatg ccggatgctc    180

cgactcctcg catggggtgt cgggaaagat ttcatcggta tgggatgggg tcgcgtccta    240

tcaggtagtc ggcggggtaa cggcccaccg agcctacgac gggtagccgg cctgagaggg    300

cgaccggcca cattgggact gagatacggc ccagactcct acgggaggca gcagtgggga    360

atattgcaca atgggcgcaa gcctgatgca gcgacgccgc gtgcgggatg acggccttcg    420

ggttgtaaac cgcttttgat cgggagcaag ccttcgggtg agtgtacctt tcgaataagc    480

accggctaac tacgtgccag cagccgcggt aatacgtagg gtgcaagcgt tatccggaat    540

tattgggcgt aaagggctcg taggcggttc gtcgcgtccg gtgtgaaagt ccatcgctta    600
```

```
acggtggatc tgcgccgggt acgggcgggc tggagtgcgg taggggagac tggaattccc    660
ggtgtaacgg tggaatgtgt agatatcggg aagaacacca atggcgaagg caggtctctg    720
ggccgttact gacgctgagg agcgaaagcg tggggagcga acaggattag ataccctggt    780
agtccacgcc gtaaacggtg gatgctggat gtggggcccg ttccacgggt tccgtgtcgg    840
agctaacgcg ttaagcatcc cgcctgggga gtacggccgc aaggctaaaa ctcaaagaaa    900
ttgacggggg cccgcacaag cggcggagca tgcggattaa ttcgatgcaa cgcgaagaac    960
cttacctggg cttgacatgt tcccgacagc cgtagagata tggcctccct tcggggcggg   1020
ttcacaggtg gtgcatggtc gtcgtcagct cgtgtcgtga gatgttgggt taagtcccgc   1080
aacgagcgca accctcgccc tgtgttgcca gcacgtcatg gtgggaactc acgggggacc   1140
gccggggtca actcggagga aggtggggat gacgtcagat catcatgccc cttacgtcca   1200
gggcttcacg catgctacaa tggccggtac aacgggatgc gacacggcga cgtggagcgg   1260
atccctgaaa accggtctca gttcggattg gagtctgcaa cccgactcca tgaaggcgga   1320
gtcgctagta atcgcggatc agcaacgccg cggtgaatgc gttcccgggc cttgtacaca   1380
ccgcccgtca agtcatgaaa gtgggtagca cccgaagccg gtggcctaac cctttgtgga   1440
tggagccgtc taaggtgaga ctcgtgattg ggactaagtc gtaacaaggt agccgtaccg   1500
gaaggtgcgg ctggatcacc tccttt                                        1526
```

<210> SEQ ID NO 21
<211> LENGTH: 1531
<212> TYPE: DNA
<213> ORGANISM: Eubacterium ventriosum

<400> SEQUENCE: 21

```
aacgagagtt tgatcctggc tcaggatgaa cgctggcggc gtgcttaata catgcaagtc     60
gaacgaagca ccttggacag aatccttcgg gaggaagacc attgtgactg agtggcggac    120
gggtgagtaa cgcgtgggta acctgccttg tacaggggga taacagttgg aaacgactgc    180
taataccgca taagcgcaca gtaccgcatg gtacggtgtg aaaaactccg gtggtacaag    240
atggacccgc gtctgattag ctggttggtg aggtaacggc ccaccaaggc gacgatcagt    300
agccgacttg agagagtgat cggccacatt gggactgaga cacggcccaa actcctacgg    360
gaggcagcag tagggaatat tgcacaatgg gggaaaccct gatgcagcga cgccgcgtga    420
aggaagaagt atttcggtat gtaaacttct atcagcaagg aagaaaatga cggtacttga    480
ctaagaagcc ccggctaaat acgtgccagc agccgcggta atacgtatgg ggcaagcgtt    540
atccggattt actgggtgta aagggagcgt aggcggcatg gcaagtcaga agtgaaagcc    600
tggggctcaa ccccggaatt gcttttgaaa ctgtcaggct agagtgtcgg aggggtaagc    660
ggaattccta gtgtagcggt gaaatgcgta gatattagga ggaacaccgg tggcgaaggc    720
ggcttactgg acgattactg acgctgaggc tcgaaagcgt ggggagcaaa caggattaga    780
taccctggta gtccacgccg taaacgatga atactaggtg tcgggggaca atagttcctc    840
ggtgccgaag caaacgcatt aagtattcca cctggggagt acgttcgcaa gaatgaaact    900
caaaggaatt gacggggacc cgcacaagcg gtggagcatg tggtttaatt cgaagcaacg    960
cgaagaacct tacctgctct tgacatccca ctgacaggtc agtaatgtga ccctttcttc   1020
ggaacagtgg agacaggtgg tgcatggttg tcgtcagctc gtgtcgtgag atgttgggtt   1080
aagtcccgca acgagcgcaa cccttgtctt tagtagccag cagtacggct gggcactcta   1140
```

```
gagagactgc cagggataac ctggaggaag gcggggatga cgtcaaatca tcatgcccct   1200

tacgagcagg gctacacacg tgctacaatg gcgtaaacaa agggaagcga ccccgtgagg   1260

gcaagcaaat ctcaaaaata acgtctcagt tcggattgta gtctgcaact cgactacatg   1320

aagctggaat cgctagtaat cgcgaatcag aatgtcgcgg tgaatacgtt cccgggtctt   1380

gtacacaccg cccgtcacac catgggagtt ggatatgccc gaagtcagtg acccaaccgt   1440

aaggagggag ctgccgaagg tggagccgat aactggggtg aagtcgtaac aaggtagccg   1500

tatcggaagg tgcggctgga tcacctcctt t                                 1531
```

<210> SEQ ID NO 22
<211> LENGTH: 1528
<212> TYPE: DNA
<213> ORGANISM: Barnesiella intestinihominis

<400> SEQUENCE: 22

```
cgaagagttt gatcctggct caggatgaac gctagcgaca ggcctaacac atgcaagtcg     60

aggggcagcg gggaggtagc aatacctttg ccggcgaccg gcgcacgggt gagtaacacg    120

tatgcaatcc acctgtaaca gggggataac ccggagaaat ccggactaat accccataat    180

atgggctctc cgcatggagg gttcattaaa gagagcaatt ttggttacag acgagcatgc    240

gctccattag ccagttggcg ggtaacggc ccaccaaagc gacgatggat aggggttctg    300

agaggaaggt cccccacatt ggaactgaga cacggtccaa actcctacgg gaggcagcag    360

tgaggaatat tggtcaatgg tcggcagact gaaccagcca agtcgcgtga gggaagacgg    420

ccctacgggt tgtaaacctc ttttgtcgga gagtaaagta cgctacgtgt agtgtattgc    480

aagtatccga agaaaaagca tcggctaact ccgtgccagc agccgcggta atacggagga    540

tgcgagcgtt atccggattt attgggttta aagggtgcgt aggcggcacg ccaagtcagc    600

ggtgaaattt tcgggctcaa cccggactgt gccgttgaaa ctggcgagct agagtgcaca    660

agaggcaggc ggaatgcgtg gtgtagcggt gaaatgcata gatatcacgc agaaccccga    720

ttgcgaaggc agcctgctag ggtgcgacag acgctgaggc acgaaagcgt gggtatcgaa    780

caggattaga taccctggta gtccacgcag taaacgatga atactaactg tttgcgatac    840

aatgtaagcg gtacagcgaa agcgttaagt attccacctg gggagtacgc cggcaacggt    900

gaaactcaaa ggaattgacg gggcccgca caagcggagg aacatgtggt ttaattcgat    960

gatacgcgag gaaccttacc cgggctcaaa cgcaggggga atatatatga aagtatatag   1020

ctagcaatag tcacctgcga ggtgctgcat ggttgtcgtc agctcgtgcc gtgaggtgtc   1080

ggcttaagtg ccataacgag cgcaacccct atcgacagtt actaacgggt caagccgagg   1140

actctgtcga gactgccggc gcaagccgcg aggaaggtgg ggatgacgtc aaatcagcac   1200

ggcccttacg tccggggcga cacacgtgtt acaatggcag gtacagaagg cagccagtca   1260

gcaatgacgc gcgaatcccg aaaacctgtc tcagttcgga ttggagtctg caacccgact   1320

ccatgaagct ggattcgcta gtaatcgcgc atcagccatg gcgcggtgaa tacgttcccg   1380

ggccttgtac acaccgcccg tcaagccatg gaagccggga gtacctgaag catgcaaccg   1440

caaggagcgt acgaaggtaa taccggtaac tggggctaag tcgtaacaag gtagccgtac   1500

cggaaggtgc ggctggaaca cctccttt                                      1528
```

<210> SEQ ID NO 23
<211> LENGTH: 1523
<212> TYPE: DNA
<213> ORGANISM: Bacteroides stercoris
<220> FEATURE:
<221> NAME/KEY: misc_feature
<223> OTHER INFORMATION: R= A or G, W= A or T, Y= C or T

<400> SEQUENCE: 23

```
atgaagagtt tgatcctggc tcaggatgaa cgctagctac aggcttaaca catgcaagtc     60

gaggggcagc atcatcaaag cttgctttga tggatggcga ccggcgcacg ggtgagtaac    120

acgtatccaa cctgccgaca acactgggat agcctttcga aagaaagatt aatacyggat    180

ggcatagttt tcccgcatgg gataattatt aaagaatttc ggttgtcgat ggggatgcgt    240

tccattaggc agttggcggg gtaacggccc accaaaccwa cgatggatag gggttctgag    300

aggaaggtcc cccacattgg aactgagaca cggtccaaac tcctacggga ggcagcagtg    360

aggaatattg gtcaatggac gagagtctga accagccaag tagcgtgaag gatgactgcc    420

ctatgggttg taaacttctt ttatacggga ataaagttag ccacgtgtgg ytttttgtat    480

gtaccgtatg aataaggatc ggctaactcc gtgccagcag ccgcggtaat acggaggatc    540

cgagcgttat ccggatttat tgggtttaaa gggagcgtag gcgggttgtt aagtcagttg    600

tgaaagtttg cggctcaacc gtaaaattgc agttgatact ggcgaccttg agtgcaacag    660

aggtaggcgg aattcgtggt gtagcggtga aatgcttaga tatcacgaag aactccgatt    720

gcgaaggcag cttactggat tgtaactgac gctgatgctc gaaagtgtgg gtatcaaaca    780

ggattagata ccctggtagt ccacacagta aacgatgaat actcgctgtt ggcgatatac    840

rgtcagcggc caagcgaaag cattaagtat tccacctggg gagtacgccg gcaacggtga    900

aactcaaagg aattgacggg ggcccgcaca agcggaggaa catgtggttt aattcgatga    960

tacgcgagga accttacccg ggcttaaatt gcaactgact gaaccggaaa cggttctttc   1020

ttcggacagt tgtgaaggtg ctgcatggtt gtcgtcagct cgtgccgtga ggtgtcggct   1080

taagtgccat aacgagcgca acccttatcg atagttacta gcaggtcatg ctgaggactc   1140

tattgagact gccgtcgtaa gatgtgagga aggtggggat gacgtcaaat cagcacggcc   1200

cttacgtccg gggctacaca cgtgttacaa tgggggggtac agaaggcagc tacacggcga   1260

cgtggtgcta atccctaaag cctctctcag ttcggattgg agtctgcaac ccgactccat   1320

gaagctggat tcgctagtaa tcgcgcatca gccacggcgc ggtgaatacg ttcccgggcc   1380

ttgtacacac cgcccgtcaa gccatgaaag ccgggggtac ctgaagtacg taaccgcgag   1440

gagcgtccta gggtaaaact ggtgattggg gctaagtcgt aacaaggtag ccgtaccgga   1500

aggtgcggct ggaacacctc ctt                                           1523
```

<210> SEQ ID NO 24
<211> LENGTH: 1530
<212> TYPE: DNA
<213> ORGANISM: Roseburia faecis
<220> FEATURE:
<221> NAME/KEY: misc_feature
<223> OTHER INFORMATION: R= A or G, S= G or C, Y= C or T

<400> SEQUENCE: 24

```
atgagagttt gatcctggct caggatgaac gctggcggcg tgcttaacac atgcaagtcg     60

aacgaagcac tctatttgat ttccttcggg attgaagatt ttgtgactga gtggcggacg    120

ggtgagtaac gcgtgggtaa cctgcctcat acagggggat aacagttgga aacgactgct    180

aataccgcat aagcgcacrg gatygcatga tycggtgyga aaaactccgg tggtaygrga    240

tggacccgcg tctgattagc cagttggcag ggtaacggcc taccaaagcg acgatcagta    300
```

```
gccgacctga gagggtgacc ggccacattg ggactgagac acggcccaaa ctcctacggg    360
aggcagcagt ggggaatatt gcacaatggg ggaaaccctg atgcagcgac gccgcgtgag    420
cgaagaagta tttcggtatg taaagctcta tcagcaggga agaagaatga cggtacctga    480
ctaagaagca ccggctaaat acgtgccagc agccgcggta atacgtatgg tgcaagcgtt    540
atccggattt actgggtgta aagggagcgc aggcggtgcg gcaagtctga tgtgaaagcc    600
cggggctcaa ccccggtact gcattggaaa ctgtcgtact agagtgtcgg aggggtaagt    660
ggaattccta gtgtagcggt gaaatgcgta gatattagga ggaacaccag tggcgaaggc    720
ggcttactgg acgataactg acgctgaggc tcgaaagcgt ggggagcaaa caggattaga    780
taccctggta gtccacgccg taaacgatga atactaggtg tcggggagca ttgctcttcg    840
gtgccgcagc aaacgcarta agtattccac ctggggagta cgttcgcaag aatgaaactc    900
aaaggaattg acggggaccc gcacaagcgg tggagcatgt ggtttaattc gaagcaacgc    960
gaagaacctt accaagtctt gacatcccga tgrcagagta tgtaatgtas yytctcytcg   1020
gagcatcggt gacaggtggt gcatggttgt cgtcagctcg tgtcgtgaga tgttgggtta   1080
agtcccgcaa cgagcgcaac ccctgttctt agtagccagc ggtycggccg ggcactctag   1140
ggagactgcc agggataacc tggaggaagg cggggatgac gtcaaatcat catgcccctt   1200
atgacttggg ctacacacgt gctacaatgg cgtaaacaaa gggaagcgga gccgtgaggc   1260
cgagcaaatc tcaaaaataa cgtctcagtt cggactgtag tctgcaaccc gactacacga   1320
agctggaatc gctagtaatc gcagatcaga atgctgcggt gaatacgttc ccgggtcttg   1380
tacacaccgc ccgtcacacc atgggagttg gaaatgcccg aagtcagtga cccaaccgca   1440
aggagggagc tgccgaaggc aggttcgata actggggtga agtcgtaaca aggtagccgt   1500
atcggaaggt gcggctggat cacctccttt                                    1530
```

```
<210> SEQ ID NO 25
<211> LENGTH: 1508
<212> TYPE: DNA
<213> ORGANISM: Slackia isoflavoniconvertans
<220> FEATURE:
<221> NAME/KEY: misc_feature
<223> OTHER INFORMATION: R= A or G, W= A or T, Y= C or T, K= G or T, M=
      A or C

<400> SEQUENCE: 25

cggagagttt gatcctggct caggatgaac gctggcggcg cgcctaacac atgcaagtcg     60
aacgagtaag acgccttcgg gcgtggatag agtggcgaac gggtgagtaa cacgtgacca    120
acctgccccc tcctccggga caacctcggg aaaccgaggc taataccgga tactccgggc    180
cccccgcatg ggrkgcccgg gaaagccctg rcgggagggg atggggtcgc ggcccatcag    240
gtagacggcg gggtaacggc ccaccgtgcc yrcwacgggt agccgggctg agaggccgat    300
cggccacatt gggactgaga cacggcccag actcctacgg gaggcagcag tggggaattt    360
tgcgcaatgg gggcaaccct gacgcagcga cgccgcgtgc gggacgaagt cattcgtgac    420
gtaaaccgct ttcagcgagg aagaaccatg acggtactcg cagaagaagc cccggctaac    480
tacgtgccag cagccgcggt aatacgtagg gggcgagcgt tatccggaat cattgggcgt    540
aaagcgcgcg caggcgggct ttcaagcggc ggcgtcgaag ccgggggctc aaccccccgga    600
agcgccccga actggaagcc tcggatgcgg cagggggagg cggaattccc ggtgtagcgg    660
tgaaatgcgc agatatcggg aagaacaccg acggcgaagg cagcctcctg ggccggcatc    720
gacgctgagg cgcgaaagct gggggagcga acaggattag ataccctggt agtcccagcc    780
```

-continued

```
gtaaacgatg gacgctaggt gtggggggaw mgrtccctcc gtgccgaagc caacgcatta    840
agcgtcccgc ctggggagta cggccgcaag gctaaaactc aaaggaattg acgggggccc    900
gcacaagcag cggagcatgt ggcttaattc gaagcaacgc gaagaacctt accagggctt    960
gacatatcgg tgaagccgga gagatccggt ggccgagagg agccgataca ggtggtgcat   1020
ggctgtcgtc agctcgtgcc gtgaggtgtt gggttaagtc ccgcaacgag cgcaaccccc   1080
gccgcgtgtt gccagcattc agttgggcac tcacgcggga ctgccggcgt caagccggag   1140
gaaggcgggg acgacgtcaa gtcatcatgc ccctcatgcc ctgggccgca cacgtgctac   1200
aatggccggc acaacgggtt gccaccccgc gagggggagc ggatccccyaa agccggcccc  1260
agttcggatc gcaggctgca acccgcctgc gtgaagccgg agttgctagt aatcgcggat   1320
cagcacgccg cggtgaatac gttcccgggc cttgtacaca ccgcccgtca caccacccga   1380
gtcgtctgca cccgaagccg ccggccgaac ccctccgggg ggcggaggcg tcgaaggtgt   1440
ggagggtgag gggggtgaag tcgtaacaag gtagccgtac cggaaggtgc ggctggatca   1500
cctccttt                                                             1508
```

THERAPEUTIC BACTERIAL COMPOSITION

Ulcerative Colitis (UC) is a chronic inflammatory bowel disease characterised by immune-mediated inflammation at the mucosal lining of the colon. This chronic inflammation occurs between the proximal colon and rectum, characterised by ulceration of the colonic epithelial barrier leading to abdominal pain, rectal bleeding, and frequent/bloody diarrhoea (Ungaro et al., 2017). The incidence and prevalence of this disease continues to increase, with 10-15% of patients with disease progression requiring colectomy (Ungaro et al., 2017; Farrell, 2019).

Similar to UC, Crohn's Disease (CD) is a chronic inflammatory bowel disease characterised by immune-mediated inflammation, however, it can occur throughout the entire gastro-intestinal tract, Over the course of the disease patients present with complications requiring surgery e.g. strictures, and fistulas (Torres et al., 2017; GBD 2017 Inflammatory Bowel Disease Collaborators, 2020).

Existing standard of care treatments aim to induce and maintain mucosal healing via immune modulation. As of 2020, the NICE recommended first-line therapy for mild to moderate Ulcerative Colitis is topical 5-ASA (Abdulrazeg et al., 2019). When patients fail to respond to first-line therapy or present with more severe disease, they are escalated through a series of treatment options—corticosteroids, immune-modulators, anti-TNF, and antibody therapy (Ungaro et al., 2017). All existing treatment options target mechanisms to modulate the immune system, which can have severe side-effects (Caviglia, Boskoski and Cicala, 2008). However, recent evidence has shown that the microbiome may play a role in the disease aetiology (Neurath, 2020). This may account for the variable response seen in trials evaluating existing therapies which do not account for the microbiome e.g. anti-TNF (Rutgeerts et al., 2005).

Moayyedi et al. first demonstrated that faecal microbiota transplants (FMT) could be used to treat patients with Ulcerative Colitis (Moayyedi et al., 2015). Additional studies have continued to demonstrate this effect (Costello et al., 2017). In 2019, Costello et al. published a paper in JAMA which demonstrated that FMT can induce and maintain steroid-free remission in 32% of patients with mild to moderate Ulcerative Colitis (Costello et al., 2019). Additionally, Kump et al. showed that antibiotics had minimal effect on UC patient's disease activity without the use of FMT, suggesting the addition of bacterial strains is needed for clinical remission (Kump et al., 2018). This suggests the transfer of microbiota from a healthy donor is capable of inducing clinical remission in UC patients.

FMT has also been shown to play a role in CD, with Sokol et al. showing engraftment of microbiota associated with maintenance of remission (Sokol et al., 2020). Metwaly et al. further explored the role of the microbiome by exploring the multi-omic profiles CD patients treated with haematopoietic stem cell therapy (HSCT). In the study, microbiome mechanism were identified which may play a role in the disease (Metwaly et al., 2020).

In view of the limited treatment options currently available, improved methods of treating colitis are needed. The present invention is aimed at addressing this need.

SUMMARY OF THE INVENTION

The invention is based on the finding that changes in specific bacteria in the UC patient's microbiome following FMT correlate with clinical remission.

Thus, the inventors have found that engraftment of bacterial strains from donor stool into the patients and associated abundance changes of bacteria in the microbiome correlates with treatment response. Thus, bacteria that are useful in the treatment of UC, originating in the donors, have been identified in the patients with disease severity reduction.

The bacteria identified and described herein may be employed individually or in combination to provide treatment of UC or CD.

The identified bacteria are derived by patient-first discovery, and they correlate with patient response.

Thus, in a first aspect, the invention relates to a composition comprising a bacterium selected from one or more bacterial species as shown in Table 1, for example comprising 1, 2, 3, 4, 5, 6, 7, 8, 9 or 10 isolated bacteria selected from one or more bacteria as shown in Table 1. In some embodiments, the composition comprises multiple bacterial species ("a consortium of bacteria") i.e. 2 to 10 bacterial species as shown herein.

In another aspect, the invention relates to a composition comprising isolated bacteria selected from at least four species wherein the bacteria from the first species comprise a 16S rDNA sequence having at least 98.7% sequence identity with a nucleic acid sequence according to SEQ ID NO: 1 or 11, the bacteria from the second species comprise a 16S rDNA sequence having at least 98.7% sequence identity with a nucleic acid sequence according to SEQ ID NO: 2, 14 or 17, the bacteria from the third species comprise a 16S rDNA sequence having at least 98.7% sequence identity with a nucleic acid sequence according to SEQ ID NO:3 or 18 and the bacteria from the fourth species comprise a 16S rDNA sequence having at least 98.7% sequence identity with a nucleic acid sequence according to SEQ ID NO: 4, 12, 15 or 18. For example, the composition may comprise SEQ ID NO: 1, 2, 3, 4, 11, 14 or 17, 18, 12, 15 and/or 19.

The composition may further comprise one or more further bacteria selected from bacteria comprising a 16S rDNA sequence having at least 98.7% sequence identity with a nucleic acid sequence according to SEQ ID NO: 5, 20, 6, 21, 7, 22, 8, 23, 9, 13, 24, 10 and/or 25.

In another aspect, the invention relates to a pharmaceutical composition comprising a bacterium selected from one or more bacteria as shown in Table 1, for example comprising 1, 2, 3, 4, 5, 6, 7, 8, 9 or 10 isolated bacteria selected from one or more bacteria as shown in Table 1 and a pharmaceutical carrier. For example, the pharmaceutical composition may comprise isolated bacteria selected from at least four species wherein the bacteria from the first species comprise a 16S rDNA sequence having at least 98.7% sequence identity with a nucleic acid sequence according to SEQ ID NO: 1, 11 or 16, the bacteria from the second species comprise a 16S rDNA sequence having at least 98.7% sequence identity with a nucleic acid sequence according to SEQ ID NO: 2, 14 or 17, the bacteria from the third species comprise a 16S rDNA sequence having at least 98.7% sequence identity with a nucleic acid sequence according to SEQ ID NO:3 or 18 and the bacteria from the fourth species comprise a 16S rDNA sequence having at least 98.7% sequence identity with a nucleic acid sequence according to SEQ ID NO: 4, 12, 15 or 19. For example, the pharmaceutical composition may comprise SEQ ID NO: 1, 2, 3, 4, 11, 14 or 17, 18, 12, 15 and/or 19.

The pharmaceutical composition may further comprise one or more further bacteria selected from bacteria comprising a 16S rDNA sequence having at least 98.7% sequence identity with a nucleic acid sequence according to SEQ ID NO: 5, 20, 6, 21, 7, 22, 8, 23, 9, 13, 24, 10 and/or 25.

In another aspect, the invention relates to a composition or a pharmaceutical composition as described above for use in the treatment of disease.

In another aspect, the invention relates to a composition or a pharmaceutical composition as described above for use in the treatment of UC or CD.

In another aspect, the invention relates to a method for treating UC or CD comprising administering composition or a pharmaceutical composition as described above to a subject. In another aspect, the invention relates to the use of a composition or a pharmaceutical composition as described in the manufacture of a medicament for the treatment of UC or CD.

In another aspect, the invention relates to a kit comprising a composition as described above.

In another aspect, the invention relates to a kit comprising a sealable container configured to receive a biological sample and means to detect a bacterial isolate identified herein. For example, the kit may comprise polynucleotide primers for amplifying one or more 16S rDNA polynucleotide sequence from at least one gut associated bacterium to form an amplified 16S rDNA polynucleotide sequence, wherein the amplified 16S rDNA sequence has at least 97% identity to a polynucleotide sequence selected from SEQ ID NOs 1 to SEQ ID NO 25; a detecting reagent to detect the amplified 16S rDNA sequence; and instructions for use. Alternatively, other genomic sequences may be amplified.

In another aspect, the invention relates to a food product or a vaccine comprising the composition as described above.

In another aspect, the invention relates to a method for identifying a faecal donor comprising the assessment of a faecal sample of a subject for the presence of one or more bacteria selected from Table 1; identifying the faecal donor based on the presence and/or abundance of one or more bacteria selected from Table 1.

In another aspect, the invention relates to the use of one or more bacteria selected from Table 1 in a method for identifying a donor for FMT therapy.

In another aspect, the invention relates to a method for treating faecal transplant prior to administration to a subject comprising supplementing the faecal transplant with one or more bacteria selected from Table 1.

In another aspect, the invention relates to a Christensenellaceae R-7 group sp. *Bacterium* or a composition comprising a Christensenellaceae R-7 group sp. *Bacterium*, for use in the prevention and/or treatment of a disease, for example UC or CD.

In another aspect, the invention relates to a composition comprising a Christensenellaceae R-7 group sp. *bacterium* according to SEQ ID No. 2, 14 or 17.

DETAILED DESCRIPTION

Figure 1:
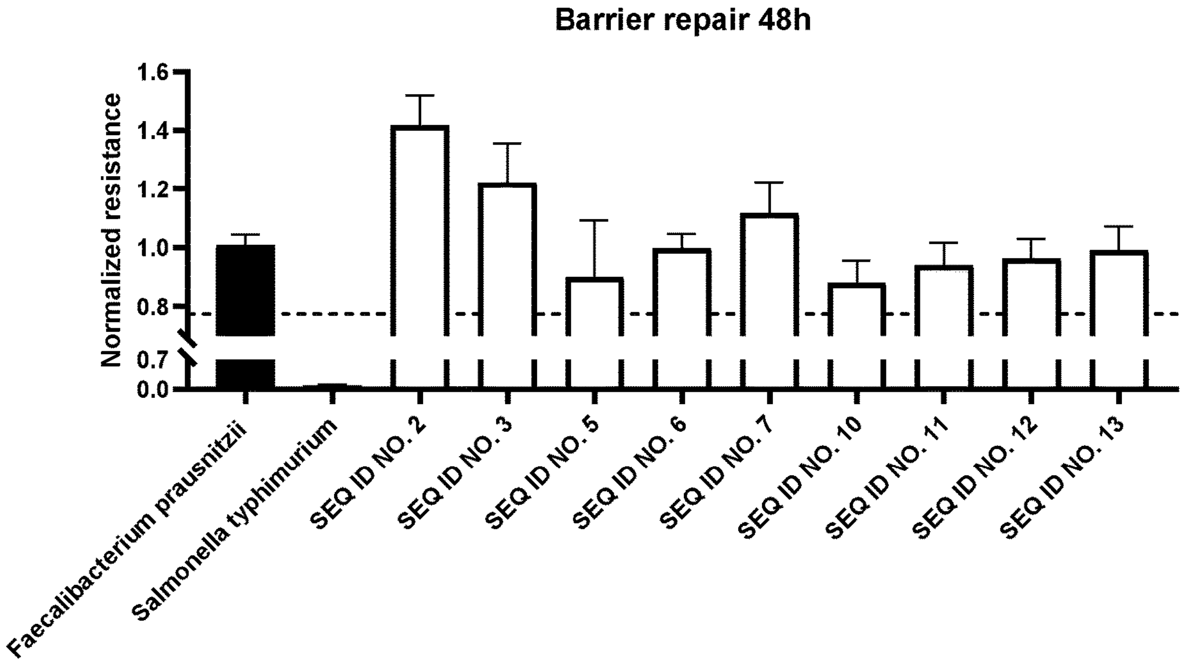
FIG. 1. Caco-2 barrier repair assay. The results of this assay show that the isolated bacteria can repair the epithelial layer after it has been damaged. This is a key mechanism in treating UC alongside immune modulation and decolonisation of species which break the barrier.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of microbiology, cell and tissue culture, pathology, molecular biology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012).

The nomenclatures used in connection with, and the laboratory procedures and techniques of analytical chemistry, microbiology, bioinformatics and medicinal and pharmaceutical chemistry described herein are those well-known and commonly used in the art.

The invention relates to therapeutic bacterial compositions each comprising one or more, e.g. a consortium of defined bacterial isolates. The compositions are useful in the treatment of disease, in particular UC and CD.

The bacterial compositions of the invention include isolated bacteria and are not therefore faecal microbiota transplants (FMT). They do not contain faecal material, but contain defined mixtures of bacterial isolates free of faecal material. Preparations that contain a defined bacterial mixture are generally accepted to be a safer treatment than FMT. An advantage of the present composition is that it comprises only fully defined and characterised bacteria and no undefined or unwanted components, which may be present in donor stools, thereby allowing the therapeutic composition to be standardised and increasing safety of the composition. Thus, in aspects relating to bacterial compositions, the invention excludes administration of faecal transplants.

FMTs relies on a stool sample from a healthy human donor which is administered directly to the recipient, e.g. via colonoscopy, without bacteria present in the stool sample being isolated prior to the administration of the FMT to the recipient. While FMT is widely used, there are some disadvantages associated with FMT. The composition of the FMT material is very donor dependant and therefore is inconsistent. Despite screening of donors, it is difficult to determine the bacterial load of the samples. Donors also have to be screened for pathogens and to assess the risk of colonization with drug-resistant bacteria. Additionally, the manufacture and supply of FMT presents logistic challenges and is not readily scalable as a pharmaceutical product. In certain aspects described below, the invention also relates to augmenting FMT therapy with one or more bacterial isolate from one or more species as disclosed herein and methods for screening/identifying a faecal donor.

The compositions in this invention include isolated bacteria. The term "isolated" refers to bacteria that are isolated from the natural environment or samples. The isolated bacteria, e.g. isolated bacterial strains, are substantially free of other cellular material, chemicals and/or faecal material. Thus, as used herein, the term "isolated" bacteria refers to bacteria that have been separated from one or more undesired component, such as another bacterium or bacterial strain, one or more component of a growth medium, and/or one or more component of a sample, such as a faecal sample. In some embodiments, the bacteria are substantially isolated from a source such that other components of the source are not detected.

As used herein, the term "species" refers to a taxonomic entity as conventionally defined by genomic sequence and phenotypic characteristics. A "strain" is a particular instance of a species that has been isolated and purified according to conventional microbiological techniques. It will be understood that the terms bacteria and bacterial isolates as used herein refer to a plurality of bacteria, that is a bacterial population.

In one embodiment, the bacteria of the composition are metabolically inactive prior to administration. For example, the bacteria are lyophilised. In one embodiment, the composition includes vegetative bacterial cells and does not include bacterial spores. In one embodiment, the composition includes vegetative bacterial cells and/or bacterial spores. In one embodiment, the composition includes vegetative bacterial cells and does not include bacterial spores or is substantially devoid of spores. In one embodiment, the composition includes fewer than about 0.1%, 0.5%, 1%, 2%, 3%, 4% or 5% spores.

In one embodiment, the isolated bacteria, e.g. isolated bacterial strains, from the species listed herein, can be viable bacteria that are capable of colonising the gastrointestinal gut of a subject when administered to said subject.

The composition is preferably a live bacterial product or a live biotherapeutic product. As described herein, a live bacterial product (also referred to as a bacterial composition, a live bacterial consortium, or bacterial consortium) comprises one or more isolated live bacteria; e.g. bacterial strains from one or more bacterial species as described herein. The term live bacterial therapy is interchangeably used with bacteriotherapy herein and defines a therapy using live bacteria to restore health or alleviate disease/disease symptoms or increase response to a therapy.

The bacterial composition is selected based on the ability of the live bacterial product to induce or stimulate a desired response when administered to a subject (e.g., a UC or CD patient).

The bacterial composition provides an immunosuppressive effect and other effects/mechanisms relevant to therapy.

The composition comprises one or more bacterial species selected from those listed in Table 1. The ability of the specific bacteria or the combination of bacterial species of the live bacterial product to induce a beneficial effect, i.e. an immunosuppressive effect, can be assessed using any of method known in the art, e.g., in vitro assays for example using cell culture, or in vivo studies. Exemplary assays are described in the examples.

In one embodiment, the isolated bacteria, e.g. isolated bacterial strains, can be viable bacteria that are capable of colonising and/or engraftment of the gastrointestinal gut of a subject when administered to said subject.

The inventors have shown that by using certain bacteria, e.g. by combining bacteria from different species, a therapeutic composition can be provided which finds use as a treatment for UC or CD. Thus, in a first aspect, the invention relates to a composition comprising one, two or more isolated bacteria, e.g. a bacterial strain, selected from one or more of the bacterial species B1, B2, B3, B4, B5, B6, B7, B8, B9 and/or B10 as listed in table 1 or subsets thereof. The invention thus relates to a composition comprising one or more bacterial isolate, e.g. bacterial population, having a 16SrDNA selected from SEQ ID. Nos 1 to 25. The invention thus relates to a composition comprising or consisting of bacterial isolates of one or more of the species as shown in table 1.

Table 1 below lists the 10 bacterial species from which the isolated bacteria present in the composition are selected. Reference to exemplary 16S rDNA sequence characterising each species is also provided. The terms 16S rDNA sequence or 16S rDNA as used herein refer to DNA nucleic acid sequences, i.e. a nucleic acid molecule, which encodes 16S rRNA nucleic acid sequence i.e. a nucleic acid molecule. Nucleic acid sequences are listed in table 11. Also, as explained further below, the bacteria of the composition may have a 16S rDNA sequence with certain sequence identity to the SEQ ID listed below. Thus, in one embodiment, the composition comprises or consists of a population of 1, 2, 3, 4, 5, 6, 7, 8, 9 or 10 bacteria defined by the species name. Additionally or alternatively, the bacteria can be defined by reference to the SEQ ID No. as in table 1 and 11 and as explained further herein. Also, as explained further below, the bacteria of the composition and of other aspects as described herein may have a 16S rDNA sequence with certain sequence identity to the SEQ ID Nos. as listed below.

TABLE 1

Bacteria in Composition A.

| No | Taxonomy | 16s rDNA sequence-sequence identifier | Possible alternative taxonomy: name and/or closely related species based on closely related bacteria identified from public databases, or given name |
|---|---|---|---|
| B1 | *Bifidobacterium adolescentis* | SEQ ID NO. 1<br>SEQ ID NO. 11<br>SEQ ID NO. 16 | na |
| B2 | *Christensenellaceae* R-7 group sp. | SEQ ID NO. 2<br>SEQ ID NO. 14<br>SEQ ID NO. 17 | *Powria foxae*, *Clostridiales bacterium* P40, UBA11524 sp000437595 |
| B3 | *Senegalimassilia anaerobia* | SEQ ID NO. 3<br>SEQ ID NO. 18 | na |
| B4 | *Provetella copri* | SEQ ID NO. 4<br>SEQ ID NO. 12<br>SEQ ID NO. 15<br>SEQ ID NO. 19 | na |
| B5 | *Bifidobacterium pseudocatenulatum* | SEQ ID NO. 5<br>SEQ ID NO. 20 | na |
| B6 | *Eubacterium ventriosum* | SEQ ID NO. 6<br>SEQ ID NO. 21 | na |
| B7 | *Barnesiella intestinihominis* | SEQ ID NO. 7<br>SEQ ID NO. 22 | na |
| B8 | *Bacteroides stercoris* | SEQ ID NO. 8<br>SEQ ID NO. 23 | na |
| B9 | *Roseburia faecis* | SEQ ID NO. 9<br>SEQ ID NO. 13<br>SEQ ID NO. 24 | *Agathobacter faecis*, *Roseburia hominis* |
| B10 | *Slackia isoflavoniconvertens* | SEQ ID NO. 10<br>SEQ ID NO. 25 | na |

na = not available

Table 1 provides reference to exemplary strains for the bacterial species provided by reference to 16S rDNA. The aspects and embodiments of the invention described herein are defined by reference to the species name and/or SEQ ID NO. as shown in Tables 1 and 11. In some cases, different exemplary sequences are provided in Table 1 for the same species, e.g. corresponding to different exemplary strains which belong to the same species. Where multiple sequences are provided for a species, these sequences share a high sequence identity, e.g. the different strains have at least 98.7% sequence identity.

In the aspects and embodiments described herein, for each of B1 to B10, any of the sequences defined above (SEQ ID. Nos 1 to 25) can be used. Thus, where multiple sequences are provided for a single species, any of these sequences can be used.

In some embodiments, the live bacterial product comprises one or more bacterial strains of each of the 10 recited species above. It should be appreciated that the strains provided are exemplary strains and that closely related bacterial strains of the same species (e.g., as defined by 16S rDNA sequences and certain sequence percentage identity, e.g. 98.7%) have highly similar or the same biological properties. It would therefore be apparent to the skilled person that bacterial strains listed above can be replaced with bacterial strains of the same species. The invention is not limited to the exemplary strains.

In one embodiment, the composition comprises or consists of 10 different isolated bacteria, i.e. bacteria from each of the 10 bacterial species and or sequences references listed in table 1, for example with reference to the sequences as shown in the table or a sequence with identity thereto as explained below. In one embodiment, the composition comprises subsets/combinations of bacterial species listed in table 1. It is envisaged that any subsets/combinations of isolates from different bacterial species are provided. In one embodiment, the composition comprises or consists of 9 isolated bacteria, e.g. bacteria B1 and B3-B10 as listed in table 1.

In one embodiment, the composition does not comprise bacteria of any other species, i.e. a species not listed in Table 1 or the composition comprises only de minimis or biologically irrelevant amounts of bacteria from another species not listed in Table 1. By biologically irrelevant is meant bacteria that do not have an effect on the treatment of UC or CD. However, the composition may comprise further components that are not bacteria, e.g. pharmaceutical carriers and the like.

In one embodiment, the composition does not comprise other bacterial species that fall within a genus listed in Table 1. However, the composition may comprise further components that are not bacteria, e.g. pharmaceutical carriers and the like.

In another embodiment, the composition may comprise other bacterial species that fall within a genus listed in Table 1, but does not comprise bacterial species of a genus not listed in Table 1. However, the composition may comprise further components that are not bacteria, e.g. pharmaceutical carriers and the like.

In another embodiment, the composition may comprise other bacterial species, i.e. bacterial species not listed in table 1.

As will be apparent to a skilled person, one or a number of bacterial species selected from those listed in table 1 can be combined in a single composition. For example, the composition comprises or consists of at least 1 or 2, e.g. up to 3, up to 4, up to 5, up to 6, up to 7, up to 8, up to 9 or up to 10 isolated bacterial species selected from those shown in table 1, for example with reference to the sequences as shown in the table. Examples of combinations of bacterial species are set out below. One or more strain can be used for each species.

In one embodiment, the composition comprises at least 1, at least 2, at least 3, at least 4, at least 5, at least 6, at least 7, at least 8, at least 9 or at least 10 isolated bacterial species selected from those listed in table 1, for example with reference to the sequences as shown in table 11.

In one embodiment, the composition comprises or consists of no more than 2, no more than 3, no more than 4, no more than 5, no more than 6, no more than 7, no more than 8, no more than 9 or no more than 10 isolated bacterial species selected from those listed in table 1, for example with reference to the sequences as shown in table 11.

In one embodiment, the composition comprises or consists of 2 to 4, 2 to 5, 2 to 6, 2 to 7, 2 to 8, 2 to 9 or 2 to 10 isolated bacterial species selected from those shown in table 1, for example with reference to the sequences as shown in table 11.

In one embodiment, the composition comprises or consists of 1 to 3, 1 to 4, 1 to 5, 1 to 6, 1 to 7, 1 to 8, 1 to 9 or 1 to 10 isolated bacterial species selected from those shown in table 1, for example with reference to the sequences as shown in table 11.

In one embodiment, the composition comprises or consists of 1, 2, 3, 4, 5, 6, 7, 8, 9 or 10 isolated bacterial species selected from those listed in table 1, for example with reference to the sequence IDs as shown in table 1 and 11.

In one embodiment, the composition comprises or consists of isolated bacteria as shown in composition A in table 2. This table shows bacteria from 10 different species (B1-B10). Thus, in one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24 and bacteria comprising a 16S rDNA sequence having at least 98.7% sequence identity with a nucleic acid sequence according to SEQ ID NO: 10 or 25.

In one embodiment, the composition comprises or consists of isolated bacteria as shown in composition B in table 3. This table shows bacteria from 9 different species (B1, B2-B10). Thus, in one embodiment, the composition comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23 a 16S rDNA sequence having at least 98.7% sequence identity with a nucleic acid sequence according to SEQ ID NO: 9, 13 or 24 and bacteria comprising a 16S rDNA sequence having at least 98.7% sequence identity with a nucleic acid sequence according to SEQ ID NO: 10 or 25.

In one embodiment, the composition comprises or consists of isolated bacteria as shown in composition C in table 4. This table shows bacteria from 8 different species (B1-B5, B7, B8, B10). Thus, in one embodiment, the composition comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23 and bacteria comprising a 16S rDNA sequence having at least 98.7% sequence identity with a nucleic acid sequence according to SEQ ID NO: 10 or 25.

In one embodiment, the composition comprises or consists of isolated bacteria as shown in composition D in table 5. This table shows bacteria from 8 different species (B1-B8). Thus, in one embodiment, the composition comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23 and bacteria comprising a 16S rDNA sequence having at least 98.7% sequence identity with a nucleic acid sequence according to SEQ ID NO: 10 or 25.

In one embodiment, the composition comprises or consists of isolated bacteria as shown in composition E in table 6. This table shows bacteria from 9 different species (B1-B5, B7, B8, B9, B10). Thus, in one embodiment, the composition comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24 and bacteria comprising a 16S rDNA sequence having at least 98.7% sequence identity with a nucleic acid sequence according to SEQ ID NO: 10 or 25.

In one embodiment, the composition comprises or consists of isolated bacteria as shown in composition F in table 7. This table shows bacteria from 6 different species (B1-B4, B7, B10). Thus, in one embodiment, the composition comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 7 or 22 and bacteria comprising a 16S rDNA sequence having at least 98.7% sequence identity with a nucleic acid sequence according to SEQ ID NO: 10 or 25.

In one embodiment, the composition comprises or consists of isolated bacteria as shown in composition G in table 8. This table shows bacteria from 4 different species (B2, B3, B4, B7). Thus, in one embodiment, the composition comprises or consists of isolated bacteria selected from bacteria comprising a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19 and bacteria comprising a 16S rDNA sequence having at least 98.7% sequence identity with a nucleic acid sequence according to SEQ ID NO: 7 or 22.

In one embodiment, the composition comprises or consists of isolated bacteria as shown in composition H in table 9. This table shows bacteria from 3 different species (B3, B4, B7). Thus, in one embodiment, the composition comprises or consists of isolated bacteria selected from bacteria comprising a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19 and bacteria comprising a 16S rDNA sequence having at least 98.7% sequence identity with a nucleic acid sequence according to SEQ ID NO: 7 or 22.

In one embodiment, the composition comprises or consists of isolated bacteria from 4 species selected from those listed in table 1, for example *B. adoloscentis, Bifidobacterium pseudocatenulatum, Senegalimassilia anaerobia* and Christensenellaceae R-7 group sp, for example with reference to the sequence IDs as shown in table 1 and 11. Thus, the composition may comprise or consist of bacteria from a first species comprising a 16S rDNA sequence having at least 98.7% sequence identity with a nucleic acid sequence according to SEQ ID NO: 1, 11 or 16, bacteria from a second species comprising a 16S rDNA sequence having at least 98.7% sequence identity with a nucleic acid sequence according to SEQ ID NO: 5 or 20, bacteria from a third species comprising a 16S rDNA sequence having at least 98.7% sequence identity with a nucleic acid sequence according to SEQ ID NO: 3 or 18 and bacteria from a fourth species comprising a 16S rDNA sequence having at least 98.7% sequence identity with a nucleic acid sequence according to SEQ ID NO: 2, 14 or 17. In another embodiment, the composition comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, and bacteria comprising a 16S rDNA sequence having at least 98.7% sequence identity with a nucleic acid sequence according to SEQ ID NO: 4, 12, 15 or 19.

In one embodiment, the composition comprises or consists of isolated bacteria from 4 species selected from those listed in table 1, for example *B. adoloscentis, Eubacterium ventriosum*, Christensenellaceae R-7 group sp., *Provetella copri, Bacteroides stercoris* and *Barnesiella intestinihominis*, for example with reference to the sequence IDs as shown in table 1 and 11. Thus, the composition may comprise or consist of bacteria from a species comprising a 16S rDNA sequence having at least 98.7% sequence identity with a nucleic acid sequence according to SEQ ID NO: 1, 11 or 16, bacteria from a species comprising a 16S rDNA sequence having at least 98.7% sequence identity with a nucleic acid sequence according to SEQ ID NO: 6 or 21, bacteria from a species comprising a 16S rDNA sequence having at least 98.7% sequence identity with a nucleic acid sequence according to SEQ ID NO: 2, 14 or 17, bacteria from a species comprising a 16S rDNA sequence having at least 98.7% sequence identity with a nucleic acid sequence according to SEQ ID NO: 4, 12, 15 or 19, bacteria from a species comprising a 16S rDNA sequence having at least 98.7% sequence identity with a nucleic acid sequence according to SEQ ID NO: 8 or 23 and/or bacteria from a species comprising a 16S rDNA sequence having at least 98.7% sequence identity with a nucleic acid sequence according to SEQ ID NO: 7 or 22.

In one embodiment, the composition comprises or consists of isolated bacteria from 4 species selected from those listed in table 1, for example *B. adoloscentis, Provetella copri, Bacteroides stercoris* and *Roseburia faecis*, for example with reference to the sequence IDs as shown in table 1 and 3. Thus, the composition may comprise or consist of bacteria from a first species comprising a 16S rDNA sequence having at least 98.7% sequence identity with a nucleic acid sequence according to SEQ ID NO: 1, 11 or 16, bacteria from a second species comprising a 16S rDNA sequence having at least 98.7% sequence identity with a nucleic acid sequence according to SEQ ID NO: 4, 12, 15 or 19, bacteria from a third species comprising a 16S rDNA sequence having at least 98.7% sequence identity with a nucleic acid sequence according to SEQ ID NO: 8 or 23 and bacteria from a fourth species comprising a 16S rDNA sequence having at least 98.7% sequence identity with a nucleic acid sequence according to SEQ ID NO: 29, 13 or 24.

In one embodiment, the composition comprises or consists of isolated bacteria from 4 species selected from those listed in table 1, for example *B. adoloscentis, Bifidobacterium pseudocatenulatum, Bacteroides stercoris* and *Eubacterium ventriosum*, for example with reference to the sequence IDs as shown in table 1 and 3. Thus, the composition may comprise or consist of bacteria from a first species comprising a 16S rDNA sequence having at least 98.7% sequence identity with a nucleic acid sequence according to SEQ ID NO: 1, 11 or 16, bacteria from a second species comprising a 16S rDNA sequence having at least 98.7% sequence identity with a nucleic acid sequence according to SEQ ID NO: 5 or 20, bacteria from a third species comprising a 16S rDNA sequence having at least 98.7% sequence identity with a nucleic acid sequence according to SEQ ID NO: 8 or 23 and bacteria from a fourth species comprising a 16S rDNA sequence having at least 98.7% sequence identity with a nucleic acid sequence according to SEQ ID NO: 6 or 21.

In one embodiment, the composition comprises or consists of isolated bacteria from 6 species selected from those listed in table 1, for example *B. adoloscentis, Provetella copri, Senegalimassilia anaerobia, Barnesiella intestinihominis, Eubacterium ventriosum* and Christensenellaceae R-7 group sp, for example with reference to the sequence IDs as shown in table 1 and 11. Thus, the composition may comprise or consist of bacteria from a species comprising a 16S rDNA sequence having at least 98.7% sequence identity with a nucleic acid sequence according to SEQ ID NO: 1, 11 or 16, bacteria from a species comprising a 16S rDNA sequence having at least 98.7% sequence identity with a nucleic acid sequence according to SEQ ID NO: 4, 12, 15 or 19, bacteria from a species comprising a 16S rDNA sequence having at least 98.7% sequence identity with a nucleic acid sequence according to SEQ ID NO: 3 or 18, bacteria from a species comprising a 16S rDNA sequence having at least 98.7% sequence identity with a nucleic acid sequence according to SEQ ID NO: 7 or 22, bacteria from a species comprising a 16S rDNA sequence having at least 98.7% sequence identity with a nucleic acid sequence according to SEQ ID NO: 6 or 21 and bacteria from a species comprising a 16S rDNA sequence having at least 98.7% sequence identity with a nucleic acid sequence according to SEQ ID NO: 2, 14 or 17.

In one embodiment, the composition comprises or consists of isolated bacteria from 5 species selected from those listed in table 1, for example *Bifidobacterium adoloscentis, Barnesiella intestinihominis, Senegalimassilia anaerobia*, Christensenellaceae R-7 group sp, and *Provetella Copri*, for example with reference to the sequence IDs as shown in table 1 and 3. Thus, the composition may comprise or consist of bacteria from a species comprising a 16S rDNA sequence having at least 98.7% sequence identity with a nucleic acid sequence according to SEQ ID NO: 1, 11 or 16, bacteria from a species comprising a 16S rDNA sequence having at least 98.7% sequence identity with a nucleic acid sequence according to SEQ ID NO: 7 or 22, bacteria from a species comprising a 16S rDNA sequence having at least 98.7% sequence identity with a nucleic acid sequence according to SEQ ID NO: 3 or 18, bacteria from a species comprising a 16S rDNA sequence having at least 98.7% sequence identity with a nucleic acid sequence according to SEQ ID NO: 2, 14 or 17 and bacteria from a species comprising a 16S rDNA sequence having at least 98.7% sequence identity with a nucleic acid sequence according to SEQ ID NO: 4, 12, 15 or 19.

In one embodiment, the composition comprises or consists of *B. adolescentis*, Christensenellaceae R-7 group sp., *Senegalimassilia anaerobia* and *Provetella copri*, for example with reference to the sequence IDs as shown in table 1 and 11. Thus, the composition may comprise or consist of bacteria from a species comprising a 16S rDNA sequence having at least 98.7% sequence identity with a nucleic acid sequence according to SEQ ID NO: 1, 11 or 16, bacteria from a species comprising a 16S rDNA sequence having at least 98.7% sequence identity with a nucleic acid sequence according to SEQ ID NO: 2, 14 or 17, bacteria from a species comprising a 16S rDNA sequence having at least 98.7% sequence identity with a nucleic acid sequence according to SEQ ID NO: 3 or 18, and bacteria from a species comprising a 16S rDNA sequence having at least 98.7% sequence identity with a nucleic acid sequence according to SEQ ID NO: 4, 12, 15 or 19.

In one embodiment, the composition comprises or consists of *Senegalimassilia anaerobia, Provetella copri, Barnesiella intestinihominis, Bacteroides stercoris*, and *Roseburia faecis*, for example with reference to the sequence IDs as shown in table 1 and 11. Thus, the composition may comprise or consist of bacteria from a species comprising a 16S rDNA sequence having at least 98.7% sequence identity with a nucleic acid sequence according to SEQ ID NO: 3 or 18, bacteria from a species comprising a 16S rDNA sequence having at least 98.7% sequence identity with a nucleic acid sequence according to SEQ ID NO: 4, 12, 15 or 19, bacteria from a species comprising a 16S rDNA sequence having at least 98.7% sequence identity with a nucleic acid sequence according to SEQ ID NO: 7 or 22, bacteria from a species comprising a 16S rDNA sequence having at least 98.7% sequence identity with a nucleic acid sequence according to SEQ ID NO: 8 or 23 and bacteria from a species comprising a 16S rDNA sequence having at least 98.7% sequence identity with a nucleic acid sequence according to SEQ ID NO: 9, 13 or 24.

In one embodiment, the composition comprises or consists of bacteria selected from Table 1, but does not comprise *Provetella copri, Eubacterium ventriosum*, Christensenellaceae R-7 and/or *Roseburia faecis*, for example with reference to the sequence IDs as shown in table 1 and 11. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Eubacterium ventriosum* and *Roseburia faecis*, for example with reference to the sequence IDs as shown in table 1 and 11. Thus, the composition may comprise or consist of bacteria from a species comprising a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Eubacterium ventriosum, Roseburia faecis*, and Christensenellaceae R-7 sp. for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Roseburia faecis*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 165 rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Eubacterium ventriosum*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 3 or 18, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24 and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Senigalimassilia anaerobia, Eubacterium ventriosum, Roseburia faecis*, and Christensenellaceae R-7 sp., for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 165 rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Senigalimassilia anaerobia, Eubacterium ventriosum* and *Roseburia faecis*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Senigalimassilia anaerobia* and *Eubacterium ventriosum*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24 and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Senigalimassilia anaerobia* and *Roseburia faecis*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and bacteria comprising a 16S rDNA sequence having at least 98.7% sequence identity with a nucleic acid sequence according to SEQ ID NO: 10 or 25.

In one embodiment, the composition comprises or consists of bacteria selected from Table 1, but does not comprise *Senigalimassilia anaerobia, Slackia isoflavoniconvertans*, and Christensenellaceae R-7 sp. for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, and a 16S rDNA sequence having at least 98.7% sequence identity with a nucleic acid sequence according to SEQ ID NO: 8 or 23.

In one embodiment, the composition comprises or consists of bacteria selected from Table 1, but does not comprise *Senigalimassilia anaerobia, Slackia isoflavoniconvertans*, and Christensenellaceae R-7, *Eubacterium ventriosum* and *Roseburia faecis*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, and a 16S rDNA sequence having at least 98.7% sequence identity with a nucleic acid sequence according to SEQ ID NO: 8 or 23.

In one embodiment, the composition comprises or consists of bacteria selected from Table 1, but does not comprise *Senigalimassilia anaerobia, Slackia isoflavoniconvertans*, and Christensenellaceae R-7, and *Eubacterium ventriosum*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 165 rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, and a 16S rDNA sequence having at least 98.7% sequence identity with a nucleic acid sequence according to SEQ ID NO: 9, 13 or 24.

In one embodiment, the composition comprises or consists of bacteria selected from Table 1, but does not comprise *Senigalimassilia anaerobia, Slackia isoflavoniconvertans*, and Christensenellaceae R-7, and *Roseburia faecis*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24.

In one embodiment, the composition comprises or consists of bacteria selected from Table 1, but does not comprise *Senigalimassilia anaerobia* and *Slackia isoflavoniconvertans*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24.

In one embodiment, the composition comprises or consists of bacteria selected from Table 1, but does not comprise *Senigalimassilia anaerobia* and *Slackia isoflavoniconvertans* and *Roseburia faecis*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO:6 or 21, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23.

In one embodiment, the composition comprises or consists of bacteria selected from Table 1, but does not comprise *Senigalimassilia anaerobia* and *Slackia isoflavoniconvertans* and *Eubacterium ventriosum*, for example with reference to the sequence IDs as shown in table 1 and 3. In one embodiment, the composition thus comprises or consists of isolated bacteria selected from bacteria comprising a 16S rDNA sequence having at least 98.7% sequence identity with a nucleic acid sequence according to SEQ ID NO: 1, 11 or 16, a 16S rDNA sequence having at least 98.7% sequence identity with a nucleic acid sequence according to SEQ ID NO: 2, 14 or 17, a 16S rDNA sequence having at least 98.7% sequence identity with a nucleic acid sequence according to SEQ ID NO: 4, 12, 15 or 19, a 16S rDNA sequence having at least 98.7% sequence identity with a nucleic acid sequence according to SEQ ID NO: 5 or 20, a 16S rDNA sequence having at least 98.7% sequence identity with a nucleic acid sequence according to SEQ ID NO: 7 or 22, a 16S rDNA sequence having at least 98.7% sequence identity with a nucleic acid sequence according to SEQ ID NO: 8 or 23, a 16S rDNA sequence having at least 98.7% sequence identity with a nucleic acid sequence according to SEQ ID NO: 9, 13 or 24 and bacteria comprising a 16S rDNA sequence having at least 98.7% sequence identity with a nucleic acid sequence according to SEQ ID NO: 10 or 25.

In one embodiment, the composition does not comprise *Provetella copri*, a *Bifodobacterium* and/or *Bacteroides stercoris*.

In one embodiment, the composition comprises an isolated bacterial mixture (consortium) comprising or consisting of 1 to 10 e.g. 2, 3, 4, 5, 6, 7, 8, 9 or 10 bacterial species, e.g. bacterial strains, having a 16S rDNA sequence with at least 97%, e.g. 98.7%, sequence identity or sequence identity to 16S rDNA sequences selected from the bacterial species represented as SEQ ID Nos 1 to 25. Exemplary compositions are set out above.

A skilled person would appreciate that that bacterial species selected from Table 1 and for use in the composition and methods of the invention can have the sequence shown in Table 11 or a sequence that has certain percentage identity thereto and retains biological activity; i.e. activity against UC or CD, e.g. reduction of symptoms of UC or CD.

Methods of determining sequence identity are known in the art. It is known that clades, operational taxonomic units (OTUs), species, and strains are, in some embodiments, identified by their 16S rDNA sequence. The relatedness can be determined by the percent identity and this can be determined using methods known in the art.

Bacterial species and strains used in a composition as described herein can be identified based on the 16S nucleic acid sequence (full length or part thereof, such as V regions). The 16S ribosomal DNA gene codes for the DNA component of the 30S subunit of the bacterial ribosome. It is widely present in all bacterial species. Different bacterial species have one to multiple copies of the 16S rDNA gene, and copies of the 16S rDNA gene may differ in sequence within the same bacterium. Bacteria usually carry multiple copies of a 16S rDNA gene. 16S rDNA gene sequencing is by far one of the most common methods targeting housekeeping genes to study bacterial phylogeny and genus/species classification. Thus, bacteria can be taxonomically classified based on the sequence of the gene encoding the 16S nucleic acid sequence, e.g. ribosomal DNA (rDNA) in the bacterium. This gene sequence is also referred to as the ribosomal DNA sequence (rDNA). The bacterial 16S rDNA is approximately 1500 nucleotides in length and is used in reconstructing the evolutionary relationships and sequence similarity of one bacterial isolate to another using phylogenetic approaches. 16S rDNA sequences are used for phylogenetic reconstruction as they are in general highly conserved, but contain specific hypervariable regions that harbour sufficient nucleotide diversity to differentiate genera and species of most microbes.

Using well known techniques to determine a full 16S rDNA sequence or the sequence of any hypervariable region of the 16S rDNA sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S rDNA gene or subdomain of the gene. If full 16S rDNA sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions. Next generation whole genome sequencing can be used to obtain the sequence of each 16S rDNA gene within a bacterial genome, when multiple copies of the gene are present. The V1-V9 regions of the 16S refer to the first nine hypervariable regions of the 16S rDNA gene that are often used for genetic typing of bacterial samples. Gene sequences are presented herein using letter representation to specific nucleotides, i.e. A, T, G, C. Polymorphisms in 16S rDNA gene sequence copies within a bacterium can be represented using IUPAC codes (Johnson, 2010). IUPAC codes are used in the consensus sequences shown herein.

In some embodiments, bacterial species identified as described herein are identified by sequence identity to 16S rDNA sequences as known in the art and described herein. In some embodiments, the selected species are identified by sequence identity to full length 16S rDNA sequences as shown in Table 11. In some embodiments, the selected species are identified by sequence identity to a part of the full length 16S rDNA sequences as shown in Table 11. For example, at least one of V1 to V9, such as V3-V4 or V3 or V4, of the full length 16S rDNA is used to characterise the bacterial isolate.

As used herein, the terms "homology" or "identity" generally refer to the percentage of nucleic acid residues in a sequence that are identical with the residues of the reference sequence with which it is compared, after aligning the sequences and in some embodiments after introducing gaps, if necessary, to achieve the maximum percentage homology, and not considering any conservative substitutions as part of the sequence identity. Thus, the percentage homology between two nucleic acid sequences is equivalent to the percentage identity between the two sequences. Methods and computer programs for the alignment are well known. The percentage identity between two sequences can be determined using well known mathematical algorithms.

In one embodiment, the degree of sequence identity between a query sequence and a reference sequence can be determined with the aid of a commercially available sequence comparison program. This typically involves aligning the two sequences using the default scoring matrix and default gap penalty, identifying the number of exact matches, and dividing the number of exact matches with the length of the reference sequence. Suitable computer programs useful for determining identity include, for example, BLAST (blast.ncbi.nlm.nih.gov).

In the various embodiments as set out herein when reference is made to a SEQ ID NO., sequences that have certain percentage sequence identity to the full-length sequence are also within the scope of the invention.

The full length or partial 16S rDNA of the bacterial species listed in table 11 with reference to the sequence identifier in table 1 and which is used in the compositions and methods of the invention has at least 90% e.g. at least 91%, 92%, 93%, 94%, 95%, 96%, 97%, 98%, 99% or 100%, sequence identity to the corresponding reference 16S rDNA (i.e. SEQ IDs 1 to 10). In some embodiments, the threshold sequence identity is at least 94.5%. In one embodiment, said sequence identity is at least 95%. In one embodiment, said sequence identity is at least 97%. In one embodiment, said sequence identity is at least 98.7%.

In one aspect, the composition therefore comprises one, two or more bacterial species comprising a 16S rDNA sequence selected from SEQ ID. NO. 1 to 10 or comprising a 16S rDNA sequence having at least 90% e.g. at least 91%, 92%, 93%, 94%, 95%, 96%, 97%, 98%, 99%; e.g. 97% or 98.7% identity to a nucleic acid sequence selected from SEQ ID NOs. 1 to 25.

In some embodiments, the threshold sequence identity is 94.5%, 94.6%, 94.7%, 94.8%, 94.9%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9% 99.0%, 99.1%, 99.2%, 99.3%, 99.4%, 99.5%, 99.6%, 99.7%, 99.8%, 99.9% or 100%. In one embodiment, a bacterium present in the composition belongs to the same species as a bacterium disclosed herein, has at least 90% e.g. at least 91%, 92%, 93%, 94%, 95%, 96%, 97%, 98%, 99%; e.g. 97% or 98.7% identity to a nucleic acid sequence selected from SEQ ID NOs. 1 to 25 and retains activity against UC or CD.

In one embodiment, the composition comprises or consists of one or more of the following 10 different bacterial species having a 16sDNA of the following SEQ ID Nos.: Species B1: SEQ ID No. 1, 11 or 16 or a 16S rDNA sequence having at least 90% e.g. at least 91%, 92%, 93%, 94%, 95%, 96%, 97%, 98%, 99%; e.g. 97% or 98.7% identity thereto, Species B2: SEQ ID No. 2, 14 or 17 or a 16S rDNA sequence having at least 90% e.g. at least 91%, 92%, 93%, 94%, 95%, 96%, 97%, 98%, 99%; e.g. 97% or 98.7% identity thereto, Species B3: SEQ ID No. 3 or 18 or a 16S rDNA sequence having at least 90% e.g. at least 91%, 92%, 93%, 94%, 95%, 96%, 97%, 98%, 99%; e.g. 97% or 98.7% identity thereto, Species 41: SEQ ID No. 4, 12, 15 or 19 or a 16S rDNA sequence having at least 90% e.g. at least 91%, 92%, 93%, 94%, 95%, 96%, 97%, 98%, 99%; e.g. 97% or 98.7% identity thereto, Species B5: SEQ ID No. 5 or20 or a 16S rDNA sequence having at least 90% e.g. at least 91%, 92%, 93%, 94%, 95%, 96%, 97%, 98%, 99%; e.g. 97% or 98.7% identity thereto, Species B6: SEQ ID No. 6 or 21 or a 16S rDNA sequence having at least 90% e.g. at least 91%, 92%, 93%, 94%, 95%, 96%, 97%, 98%, 99%; e.g. 97% or 98.7% identity thereto, Species B7: SEQ ID No. 7 or 22 or a 16S rDNA sequence having at least 90% e.g. at least 91%, 92%, 93%, 94%, 95%, 96%, 97%, 98%, 99%; e.g. 97% or 98.7% identity thereto, Species B8: SEQ ID No. 8 or 23 or a 16S rDNA sequence having at least 90% e.g. at least 91%, 92%, 93%, 94%, 95%, 96%, 97%, 98%, 99%; e.g. 97% or 98.7% identity thereto, Species B9: SEQ ID No. 9 or 13 or a 16S rDNA sequence having at least 90% e.g. at least 91%, 92%, 93%, 94%, 95%, 96%, 97%, 98%, 99%; e.g. 97% or 98.7% identity thereto, Species B10: SEQ ID No. 10 or 25 or a 16S rDNA sequence having at least 90% e.g. at least 91%, 92%, 93%, 94%, 95%, 96%, 97%, 98%, 99%; e.g. 97% or 98.7% identity thereto.

In one example, species used in the composition are identified based on their 16S rDNA sequence (e.g., full-length sequence, or partial sequence). In some cases, strains of bacterial species useful in an invention, e.g., strains of the species disclosed herein, can be obtained from a public biological resource center such as the ATCC (atcc.org), the DSMZ (dsmz.de), or the Riken BioResource Center (en.brc.riken.jp). 16s rDNA sequences useful for identifying species or other aspects of the invention can be obtained from public databases, e.g., the Human Microbiome Project (HMP) web site or GenBank.

A skilled person would appreciate that the compositions may include one or more than one strain of a particular bacterial species as listed in table 1. For example, the composition of the invention comprises more than one bacterial strain for species. For example, in some embodiments, the composition of the invention comprises more than one strain from within the same species listed in table 1 (e.g. more than 1, 2, 3, 4, 5, 6, 7, 8, 9, 10, 15, 20, 25, 30, 35, 40 or 45 strains). In another embodiment, the composition of the invention comprises one bacterial strain for each species.

In one embodiment, the bacteria of the composition are capable of colonising the gastrointestinal tract of a subject. In one embodiment, the bacteria of the composition are capable of sustained engraftment in the gastrointestinal tract of a subject.

In one embodiment, the composition has one or more of the following characteristics which include biological and clinical characteristics:

- The composition is effective in treating and/or preventing UC in a subject. Treatment of UC reduces one or more symptoms of UC;
- The composition is effective in treating and/or preventing UC in an in vitro or in vivo model for UC. For example, the model may be a DSS-induced (dextran sodium sulphate) colitis model and weight loss and/or colon length may be measured;
- The composition is effective in treating and/or preventing CD in a subject. Treatment of CD reduces one or more symptoms of CD;
- The composition is effective in treating and/or preventing CD in an in vitro or in vivo model for CD. For example, the model may be a DSS-induced colitis model and weight loss may be measured;
- Administering the composition to a cell, tissue or subject modulates one or more biomarkers selected from C-reactive protein, fecal lactoferrin and fecal calprotectin;
- Administering the composition to a cell, tissue or subject increases the abundance of bacteria in the subject which creates an environment or microenvironment (e.g., metabolome) that is conducive to the treatment of UC and/or CD;
- Administering the composition to a cell, tissue or subject increases suppressive Foxp3+ or IL-10+ regulatory T cell abundance;
- Administering the composition to a cell, tissue or subject increases the production of anti-inflammatory cytokines such as IL-10 or TGF-β by Dendritic Cells and Macrophages;
- Administering the composition to a cell, tissue or subject reduces or attenuates production of at least one pro-inflammatory gene product, e.g. IL-6, IL-12, IL-17 and/or TNF-a in a human cell;
- Administering the composition to a cell, tissue or subject; e.g. in an in vitro or in vivo model, reduces or preventing disruption of, or increasing, barrier integrity of a human cell line (e.g. an epithelial cell) monolayer, e.g. a Caco2 cell monolayer treated with the consortium where the barrier function is measured by electrical impedance. This can be measured as shown in the examples.
- The composition has an immunosuppressive effect on the immune system of a subject, for example as demonstrated in an in vitro or in vivo model, for example as measured in a dendritic cell activation assay, M1 macrophage assay and CD4+ T cell polarisation assay.

Suitable assays are shown in the examples.

Thus, the composition includes at least one bacterial strain which shows one or more of the features set out above.

The ability of the specific bacteria or the combination of bacterial species to induce an anti-inflammatory effect e.g. as defined above can be assessed using any of method known in the art, e.g., in vitro assays for example using cell culture, or in vivo studies.

The subject may be a human or animal model, such a rodent, e.g. mouse model. A therapeutic composition and/or method is tested by administering the composition to the animal model either prior to induction of disease signs or symptoms, during induction, or after manifestation of at least one sign or symptom in the animal. In vitro or ex vivo models can also be used for testing efficacy, e.g. tissue or cell-based models.

The composition elicits an immune response, that is it has an immunosuppressive effect. As used herein, an "immune response" refers to the action of a cell of the immune system (e.g., T lymphocytes, B lymphocytes, natural killer (NK) cells, macrophages, eosinophils, mast cells, dendritic cells, neutrophils, etc.) and soluble macromolecules produced by any of these cells or the liver (including Abs, cytokines, and complement) that results in selective targeting, binding to, damage to, destruction of, and/or elimination from a subject of invading pathogens, cells or tissues infected with pathogens, or cancerous or other abnormal cells.

The bacterial isolates can be isolated as described in WO2013/171515 or WO2017/182796, both incorporated by reference. In one embodiment, bacterial strains are cultured and grown individually and then combined in the composition.

A bacterial isolate used in the composition is preferably a non-pathogenic strain. In other words, the bacterium preferably does not cause a disease in a healthy human individual when administered to said individual.

In one embodiment, each bacterium present in the composition is susceptible to treatment with one or more antibiotics. In other words, the bacterium is not resistant to treatment with at least one antibiotic. This allows antibiotic treatment of an individual in the event that one or more of the bacteria included in a therapeutic composition administered to the individual cause disease in the individual, contrary to expectations. Thus, in one embodiment, the bacterium is susceptible to treatment with one or more antibiotics selected from the group consisting of: a beta-lactam, fusidic acid, elfamycin, aminoglycoside, fosfomycin, tunicamycin metronidazole and/or vancomycin. In vitro and in silico methods for screening bacteria for antibiotic resistance are known in the art.

In one embodiment, the isolated bacterium included in the compositions may not comprise one or more genes encoding one or more virulence factors and/or preferably does not produce one or more virulence factors. Virulence factors in this context are properties which enhance the potential of a bacterium to cause disease in an individual. Virulence factors include the production of bacterial toxins, such as endotoxins and exotoxins by a bacterium, as well as the production of hydrolytic enzymes that may contribute to the pathogenicity of the bacterium. Methods for screening bacteria for genes encoding virulence factors are known in the art.

In some embodiments, one or more of the bacterial strains are human-derived bacteria, meaning the one or more bacterial strains were obtained from or identified from a human or a sample therefrom (e.g., a human donor). In some embodiments of the compositions provided herein, all of the bacterial strains are human-derived bacteria. In some embodiments of the compositions provided herein, the bacterial strains are derived from more than one human donor.

Isolation and characterisation can be achieved using standard methods in the art. For example, the V4-V5 region of the 16S rRNA encoding gene can be amplified and sequenced. Sequences can then be aligned and compared to the 16S sequences provided herein for the bacterial isolates. Sequence protocols and alignment software are well known in the art.

In some cases, strains of bacterial species useful in an invention, e.g., strains of the species disclosed herein, can be obtained from a public biological resource centre as described above.

The bacterial strains used in the live bacterial products provided herein generally are isolated from the microbiome of healthy individuals. In some embodiments, the live bacterial products include strains originating from a single individual. In some embodiments, the live bacterial products include strains originating from multiple individuals. In some embodiments, the bacterial strains are obtained from multiple individuals, isolated and grown up individually. The bacterial compositions that are grown up individually may subsequently be combined to provide the compositions of the disclosure. It should be appreciated that the origin of the bacterial strains of the live bacterial products provided herein is not limited to the human microbiome from a healthy individual.

In some embodiments in which the composition of the invention comprises more than one bacterial strain, species or genera, the individual bacterial strains, species or genera may be for separate, simultaneous or sequential administration. In some embodiments, the more than one bacterial strain, species or genera are stored separately but are mixed together prior to use.

As explained herein, the bacterial compositions of the invention have a therapeutic effect when administered to a subject and can be used in the treatment or prevention of UC or CD. Thus, the compositions as described here are therapeutic compositions. Thus, the invention also extends to pharmaceutical compositions comprising a composition of bacteria as described herein and methods of use.

In one embodiment, the composition may comprise a pharmaceutically acceptable excipient, carrier, buffer, stabilizer or other materials well known to those skilled in the art. Such materials should be non-toxic and should not interfere with the efficacy of the isolated bacteria present in the therapeutic composition. The precise nature of the pharmaceutically acceptable excipient or other material will depend on the route of administration, which may be oral or rectal. Many methods for the preparation of therapeutic compositions are known to those skilled in the art.

The bacterial compositions of the invention may comprise a prebiotic, a pharmaceutically acceptable carrier, insoluble fibre, a buffer, an osmotic agent, an anti-foaming agent and/or a preservative. Particular examples of excipients included in the composition are disclosed below.

Prebiotics may provide nutrients for the isolated bacteria present in the bacterial composition to assist their early growth and colonisation after administration to the individual. Any prebiotic known in the art may be used. Non-limiting examples of prebiotics include oligosaccharides, e.g., fructooligosaccharides such as oligofructose and inulin, mannan oligosaccharides and galactooligosaccharides, soluble, oligofructose-enriched inulin and soluble fibre. Insoluble fibre may be included in the therapeutic composition as a carrier, e.g., to provide protection during transit or storage. A buffer may be included in the bacterial composition to promote the viability of the isolated bacteria present. An anti-fungal agent may be included in the bacterial composition as a preservative.

In one embodiment, the therapeutic bacterial compositions may comprise no other active ingredient other than the bacterial isolates as described herein, including no other isolated bacterium, and optionally a prebiotic. Thus, the active ingredient of the therapeutic composition may consist of the group of bacterial isolates as described herein, and optionally a prebiotic.

The bacterial compositions of the invention can be administered to a subject in a variety of ways as described in more detail elsewhere herein, including in the form of a capsule, tablet, gel or liquid.

The bacterial compositions of the invention may be for oral or rectal administration to the subject. Where the composition is for oral administration, the composition may be in the form of a capsule, or a tablet. Where the therapeutic composition is for rectal administration, the therapeutic composition may be in the form of an enema. The preparation of suitable capsules, tablets and enema is well-known in the art. The capsule or tablet may comprise an enteric coating to protect the capsule or tablet from stomach acid. For example, the capsule or tablet may be enteric-coated, pH dependant, slow-release, and/or gastro-resistant. Such capsules and tablets are used, for example, to minimize dissolution of the capsule or tablet in the stomach but allow dissolution in the small intestine. When intended for oral administration, the composition can be in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like. Such a solid composition typically contains one or more inert diluents. In addition, one or more of the following can be present: binders such as carboxymethylcellulose, ethyl cellulose, microcrystalline cellulose, or gelatin, excipients such as starch, lactose or dextrins, disintegrating agents such as alginic acid, sodium alginate, corn starch and the like; lubricants such as magnesium stearate, glidants such as colloidal silicon dioxide, sweetening agents such as sucrose or saccharin, a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The bacterial composition may include a pharmaceutically acceptable carrier or vehicle can be particulate, so that the compositions are, for example, in tablet or powder form. The term "carrier" refers to a diluent, adjuvant or excipient, with which the composition is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, the composition and pharmaceutically acceptable carriers are sterile. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions can take the form of one or more dosage units. In an embodiment, the dose unit comprises at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$ or greater than $1\times10^{11}$ colony forming units (cfu) of vegetative bacterial cells. In an embodiment, the dose unit comprises a pharmaceutically acceptable excipient, an enteric coating or a combination thereof. The bacterial isolates or composition may be provided at a dose of 0.1-100 g/day, such as 0.1, 0.5, 1, 10, 15, 20, 30, 40, 50, 60, 70, 80 or 90 g/day.

The isolated bacterium or isolated bacteria present in a therapeutic composition may make up at least 1%, 5%, 10%, 15%, 20%, 25%, 30%, 35%, 40%, 45%, 50%, 55%, 60%, 65%, 7%, 75%, 80%, 85%, or 90% of the therapeutic composition by volume or weight.

Treatments or specific processes can be applied to improve the stability or viability of the bacterial isolates in the composition. The bacterial composition can be applied in a dry form or in a wet from. The bacterial composition may be lyophilized. The lyophilized therapeutic composition may comprise one or more stabilisers and/or cryoprotectants. The lyophilized bacterial composition may be reconstituted using a suitable diluent prior to administration to the individual.

Then invention also relates to a pharmaceutical composition comprising one or more bacteria of selected from the bacteria of Table 1 and a carrier.

In another aspect, there is provided a bacterial composition described herein for use in the treatment of disease. In another aspect, there is provided the use of a bacterial composition described herein in the manufacture of a medicament for the treatment or prevention of a disease. In another aspect, there is provided a bacterium as defined in table 1, for example by taxonomy or by reference to the SEQ ID No., for use in the treatment of disease.

In another aspect, there is provided a method for treating or preventing a disease in a subject comprising modulating the level of, e.g. increasing the level/relative abundance of one or more bacterium selected from B1, B2, B3, B4, B5, B6, B7, B8, B9 and/or B10 as shown in Table 1 or a subset thereof in a subject. In one embodiment, the subset comprises or consists of 1, 2, 3, 4, 5, 6, 7, 8, 9, 10 bacteria selected from Table 1. Modulating the level of one or more bacterium in the subject treats UC. In one embodiment, the method comprises administering a composition as described herein.

As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal which is the object of treatment, observation, or diagnosis. By way of example only, a subject includes, but is not limited to, a mammal, including, but not limited to, a human or a non-human mammal, such as a non-human primate, murine, bovine, equine, canine, ovine, or feline. In one embodiment, the subject is a UC or CD patient that has received prior UC treatment or is receiving treatment. In one embodiment, the subject is a UC or CD patient who has had an inadequate response to or are intolerant of a conventional or existing therapy.

In one embodiment, the disease is UC and the composition provides a UC therapy. The term "UC therapy" refers to any therapeutic regimen that aims to reduce or eliminate UC/symptoms of UC or slow the progression of UC. The anti UC therapies described herein involve the administering anti UC therapies to a subject, e.g., a subject having UC or at risk of having UC.

In one embodiment, the disease is UC and the composition provides a CD therapy. The term "CD therapy" refers to any therapeutic regimen that aims to reduce or eliminate CD/symptoms of CD or slow the progression of CD. The anti-CD therapies described herein involve the administering anti CD therapies to a subject, e.g., a subject having CD or at risk of having CD.

Administration according to the method and uses above includes oral administration or rectal administration.

The amount of the composition that is effective/active in the treatment of UC or CD will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

In some embodiments, a composition of the invention may be administered with two or more (e.g., 2, 3, 4, 5, or more) therapeutic agents, e.g. agents useful in the treatment of UC or CD.

Administration may be in a "therapeutically effective amount", this being sufficient to show benefit to the individual. Such benefit may be at least amelioration of at least one symptom. Thus "treatment" of a specified disease refers to amelioration of at least one symptom. The actual amount administered, and rate and time-course of administration, will depend on the nature and severity of what is being treated, the particular patient being treated, the clinical condition of the individual patient, the site of delivery of the composition, the type of therapeutic composition, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. A therapeutically effective amount or suitable dose of a therapeutic composition of the invention can be determined by comparing its in vitro activity and in vivo activity in an animal model. Methods for extrapolation of effective dosages in mice and other test animals to humans are known. The precise dose will depend upon a number of factors, including whether the therapeutic composition is for prevention or for treatment.

In one embodiment of the methods which require administration of the composition, the method includes the further step of detecting the presence one or more of the bacterial strain that has been administered in the subject subsequent to administration. Methods for detection include for example detecting a 16S nucleic acid sequence as defined herein of at least one administered bacterial isolate in said subject.

Efficacy of a treatment can be determined by evaluating signs and or symptoms and according to whether induction of improvement and/or maintenance of a remission or improved condition is achieved, e.g., for at least 1 week, at least two weeks, at least three weeks, at least four weeks, at least 8 weeks, or at least 12 weeks. For example, mucosal healing as judged endoscopically, histologically or via imaging techniques can be used for such evaluations, particularly for predicting long term clinical outcome in subject's diagnosed with ulcerative colitis or CD.

For UC, indications of therapeutic efficacy include, for example, normalization of stool frequency, lack of urgency, mucosal appearance at endoscopy, and absence of blood in stools. Remission is considered achieved if at least one sign or symptom is reduced for at least four weeks after completion of the treatment. Mucosal healing is one example of a measure of clinical remission. Other signs/symptoms can include normalization of C-reactive protein and/or other acute phase indicators, and subjective indicia such as those related to quality of life. Other examples of indicia can include improvement from moderate to mild using the Montreal Classification, the Mayo Score (with or without endoscopy subscore), or the Pediatric Ulcerative Colitis Index. In general, methods and compositions described herein are useful for treating a subject diagnosed with a colitis.

Improvement can be indicated by an improvement in an index of disease activity, by amelioration of clinical symptoms or by any other measure of disease activity. Once such index of disease is the ulcerative colitis Mayo score. The Mayo score is an established, validated disease activity index for mild, moderate, and severe ulcerative colitis that is calculated as the sum of the 4 subscores of stool frequency, rectal bleeding, findings of endoscopy, and physician's global assessment (PGA), and ranges from 0-12. A score of 3 to 5 points indicates mildly active disease, a score of 6 to 10 points indicates moderately active disease, and a score of 11 to 12 points indicates severe disease. The partial Mayo score, which is the Mayo score without the endoscopy subscore, is calculated as the sum of stool frequency, rectal bleeding, and physician's global assessment subscores, and ranges from 0 to 9. The modified Mayo score, which is the Mayo score without the PGA subscore, is calculated as the sum of the stool frequency, rectal bleeding, and endoscopy subscores, and ranges from 0 to 9. Other disease activity indexes for UC include for example, Ulcerative Colitis Endoscopic Index of Severity (UCEIS) score and the Bristol Stool Form Scale (BSFS) score. The UCEIS score provides an overall assessment of endoscopic severity of UC, based on mucosal vascular pattern, bleeding, and ulceration (Travis et al., Gut. 61:535-542 (2012)). The score ranges from 3 to 11 with a higher score indicating more severe disease by endoscopy. The BSFS score is used to classify the form (or consistency) of human feces into 7 categories (Fewis and Heaton, Scand J Gastroenterol. 32(9):920-924 (1997)).

Other indicators of efficacy of a therapeutic composition and/or method for treating UC or CD include engraftment of at least one bacterial species identified in table 1, at 7 days, 2 weeks, 3 weeks, 4 weeks, 5 weeks, 6 weeks, 7 weeks, 8 weeks, 9 weeks, 10 weeks, 11 weeks, or 12 weeks; clinical remission at 4 weeks, 5 weeks, 6 weeks, 7 weeks, 8 weeks, 9 weeks, 10 weeks, 11 weeks, or 12 weeks (e.g., a Mayo score<=2 with no subscore>1); or endoscopic remission at 4 weeks (Mayo endoscopy score of 0).

In one embodiment, the term "clinical response" as used herein as it relates to a subject's response to drug administration, refers to a decrease from induction baseline in the Mayo score by >30% and >3 points, with either a decrease from baseline in the rectal bleeding subscore >1 or a rectal bleeding subscore of 0 or 1.

In certain embodiments, the subject is a responder to a treatment of a method according to an embodiment of the application and is identified as having at least one of: (1) a clinical remission based on at least one of the global submissions and the US submissions; (2) an endoscopic healing; (3) a clinical response; (4) a change from baseline in Inflammatory Bowel Disease Questionnaire (IBDQ) score; (5) a mucosal healing; (6) a decrease from baseline in Mayo score; and (7) a normalization of one or more biomarkers selected from the group consisting of C-reactive protein, fecal lactoferrin and fecal calprotectin. Preferably, at least one of (1) to (7) above is identified from the subject by week 16, more preferably by week 8 or week 4, and most preferably by week 2 of the treatment.

Remission or signs or symptoms can be determined using clinical indices such as, for Crohn's disease, the Crohn's Disease Activity Index (CDAI), the PCDAI, or the amelioration or one or more elements of the PCDAI or CDAI, e.g., number of liquid or soft stools, abdominal pain, general well-being, presence of complications (such as arthralgia or arthritis, uveitis; inflammation of the iris; presence of erythema nodosum, pyoderma gangrenosum, or aphthous ulcers; anal fissures, fistulae, or abscesses; other fistulae, or fever), taking opiates or diphenoxylate/atropine for diarrhea, presence of an abdominal mass, or percentage deviation from standard weight. In some embodiments a subject treated according to a method described herein attains and/or remains at a CDAI below 150. In some embodiments, a positive response to a method is a reduction of a subjects CDAI by at least 70 points.

Compositions according to the invention may be administered together with another therapy, i.e. an anti-UC or CD therapy. The composition may be administered separately (i.e. prior or after) or together with the anti-UC or CD therapy. Anti-UC or CD therapy may include, but are not limited to an antibody therapy or corticosteroids. They can also be used as adjuvants in treatments for UC or CD. Thus, the invention also relates to a combination therapy comprising a composition of the invention and another therapy where the other therapy is an anti-UC or CD therapy.

In one embodiment of the methods which require administration of the composition, the method includes the further step of detecting the presence of one or more bacterial strain that has been administered in the subject subsequent to administration. Methods for detection include for example detecting a 16S nucleic acid sequence as defined herein of at least one administered bacterial isolate in said subject.

The composition of the present invention may be prepared by a method comprising culturing the one, two or more isolated bacteria present in the composition in a suitable medium or media. Media and conditions suitable for culturing the bacteria to be included in the therapeutic composition of the present invention are described in detail elsewhere herein. For example, a method of preparing a therapeutic composition according to the present invention may comprise the steps of:

(i) culturing a first isolated bacterium;

(ii) culturing a second and optionally a further isolated bacterium; and (iii) mixing the bacteria obtained in (i) and (ii) to prepare the therapeutic composition.

The isolated bacteria to be included in the composition may be cultured in separate steps. In other words, a separate culture of each bacterium to be included in the therapeutic composition is preferably prepared. This allows the growth of each bacterium to be evaluated and the amount of each bacterium to be included in the pharmaceutical composition to be controlled as desired. The bacteria cultured in steps (i) and (ii) preferably have distinct 16S nucleic acid sequences, that is 16S nucleic acid sequences that share less than 99%, 98.7%, 98%, 97%, 96% or 95% sequence identity.

The above method may include steps of culturing each isolated bacterium which is to be included in the composition.

The method may optionally comprise one or more further steps in which the bacteria are mixed with one or more additional ingredients, such as a pharmaceutically acceptable excipient, prebiotic, carrier, insoluble fibre, buffer, osmotic agent, antifoaming agent, and/or preservative. In addition, or alternatively, the method may comprise suspending the bacteria obtained in (i) and optionally (ii) in a chemostat medium, or saline, e.g. 0.9% saline. The bacteria obtained in (i) and optionally (ii) may be provided under a reduced atmosphere, such as N2, CO2, H2, or a mixture thereof, e.g. N2:CO2:H2. The gases may be present in appropriate ratios for the preservation of the bacteria present in the therapeutic composition. For example, the reduced atmosphere may comprise 80% N2, 10% CO2 and 10% H2. In addition, or alternatively, the method may comprise a step of lyophilising the bacteria obtained in (i) and optionally (ii), optionally in the presence of a stabiliser and/or cryprotectant. The method may also comprise a step of preparing a capsule, tablet, or enema comprising the bacteria obtained in (i) and optionally (ii). The capsule or tablet may be enteric-coated, pH dependant, slow-release, and/or gastro-resistant.

The composition of the invention may also be provided in the form of a food supplement, beverage or other food stuff. The invention thus also relates to a food product or a vaccine comprising the composition of the invention.

Identification of a Donor for FMT

Therapy by implantation or administration of human colonic microbiota into the bowel of a patient is called Faecal Microbiota Transplantation (FMT), also commonly known as faecal bacteriotherapy. However, FMT does not have a 100% efficacy rate and this is believed to be due in part to variation in donor microbiota. Moayyeddi et al. (2015) reported greater remission rate in ulcerative colitis from one donor. Identification of therapeutic components in total stool microbiota allows the identification of donors and stool samples with increased therapeutic efficacy.

In another aspect, the invention relates to a method for identifying a faecal donor comprising assessing a faecal sample of a subject for the presence, absence or abundance of one or more bacteria selected from Table 1; identifying the faecal donor based on the presence and/or abundance of one or more bacteria selected from Table 1. The sample from a donor identified can be useful in treatment of UC or CD. Therefore, the method may comprise the additional step of administering the sample to a UC or CD patient.

The invention relates to a use of one or more bacteria selected from Table 1 in a method for identifying a donor for FMT therapy.

The invention relates to a method for treating a faecal transplant prior to administration to a subject comprising supplementing the faecal transplant with one or more bacteria selected from Table 1. Methods for treating a subject with a faecal transplant thus supplemented are also envisaged.

Kits

In a further aspect, the invention relates to a kit. The kit may include components that can be used in the treatment of UC or CD as described herein or components to assess the presence, absence or abundance of one or more bacteria as listed in table 1 in a sample.

In one embodiment, the kit includes a pharmaceutical composition described herein and optionally other components. In an example, the kit can include materials to ship the collected material without harming the samples (e.g., packaged in lyophilized form, or packaged in an aqueous medium etc.). The kit may include the processed material or treatment in a sterile container, such as a nasogastric (NG) tube, a vial (e.g., for use with a retention enema), a gastro-resistant capsule (e.g., acid-bio resistant to reach the intestinal tract, having a sterile outside), etc. The kit may also comprise instructions for use.

In an alternative aspect, the kit comprises reagents to detect the bacteria described herein. For example, the kit may comprise sequencing reagents. For example, the kit may comprise:

- a sealable container configured to receive a biological sample, such as a faecal sample;
- means for detecting one or more bacteria listed in table 1, e.g. polynucleotide primers for amplifying a nucleotide sequence, e.g. a 16S rDNA polynucleotide sequence from at least one gut associated bacterium to form an amplified 16S rDNA polynucleotide sequence, wherein the amplified 16S rDNA sequence has at least 97% sequence identity to a polynucleotide sequence selected from SEQ ID NOs 1 to SEQ ID NO 25;
- a detecting reagent to detect the amplified 16S rDNA sequence; and
- instructions for use.

Further aspects and embodiments of the invention will be apparent to those skilled in the art given the present disclosure including the following experimental exemplification.

The inventors have also shown that a Christensenellaceae R-7 group sp. *bacterium* comprising a 16S rDNA according to SEQ ID No. 2, 14 or 17 shows particular efficacy in a CD4+ T Cell Polarisation Assay. The data shows that Christensenellaceae R-7 group sp. has an immunosuppressive effect in the presence of LPS (inflammatory state) by increasing immune-modulatory T cells populations.

Due to this immunosuppressive effect, a Christensenellaceae bacterium, e.g. a Christensenellaceae R-7 group sp. comprising a 16S rDNA according to SEQ ID No. 2 or a sequence with at least 90% e.g. at least 91%, 92%, 93%, 94%, 95%, 96%, 97%, 98%, 99%; e.g. 97% or 98.7% sequence identity can be used in the treatment of disease.

Thus, in another aspect, the invention relates to an isolated Christensenellaceae bacterium, e.g. a Christensenellaceae R-7 group sp. or a composition comprising a Christensenellaceae bacterium, e.g. Christensenellaceae R-7 group sp., for use in the prevention and/or treatment of a disease, for example UC or CD. For example, the Christensenellaceae R-7 group sp. comprises a 16S rDNA according to SEQ ID No. 2 or a sequence with at least 90% e.g. at least 91%, 92%, 93%, 94%, 95%, 96%, 97%, 98%, 99%; e.g. 97% or 98.7% sequence identity.

In another aspect, the invention relates to a composition, e.g. a pharmaceutical composition, comprising an isolated Christensenellaceae bacterium, e.g. a Christensenellaceae R-7 group sp. For example, the Christensenellaceae R-7 group sp. comprises a 16S rDNA according to SEQ ID No. 2 or a sequence with at least 90% e.g. at least 91%, 92%, 93%, 94%, 95%, 96%, 97%, 98%, 99%; e.g. 97% or 98.7%.

The composition may comprise further bacteria, e.g. bacteria with a therapeutic effect. In one embodiment, the composition does not comprise further bacteria, e.g. therapeutic bacteria. Thus, the composition may consist of Christensenellaceae R-7 group sp. For example, the Christensenellaceae R-7 group sp. comprises a 16S rDNA according to SEQ ID No. 2 or a sequence with at least 90% e.g. at least 91%, 92%, 93%, 94%, 95%, 96%, 97%, 98%, 99%; e.g. 97% or 98.7% sequence identity.

In some embodiments of the aspects above, the sequence identity is 94.5%, 94.6%, 94.7%, 94.8%, 94.9%, 95.0%, 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9% 99.0%, 99.1%, 99.2%, 99.3%, 99.4%, 99.5%, 99.6%, 99.7%, 99.8%, 99.9% or 100%.

In one embodiment, Christensenellaceae R-7 group sp. is capable of increasing the frequency of CD25hi Foxp3+ regulatory T cells, for example as shown in example 2.

In one embodiment, the bacteria can be viable bacteria that are capable of colonising and/or engraftment of the gastrointestinal gut of a subject when administered to said subject.

Excipients in the composition, dosage forms of the composition and administration routes may be selected from those explained above.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including any references to gene accession numbers and references to patent publications.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is described in the following embodiments:

1. A composition comprising a bacterium selected from one or more bacteria as shown in Table 1.
2. The composition according to embodiment 1 comprising 1, 2, 3, 4, 5, 6, 7, 8, 9 or 10 isolated bacteria selected from one or more bacteria as shown in Table 1.
3. The composition according to embodiment 1 or 2 wherein the one or more isolated bacteria comprise 16S rDNA sequences having at least 95%, for example 97%, 98%, 98.7% or 99% sequence identity with a nucleic acid sequence selected from SEQ ID NOs: 1 to 25.
4. The composition according to any preceding embodiment wherein said composition is formulated for oral or rectal administration.
5. The composition according to embodiment 4 wherein said composition is in the form of a capsule, tablet, gel or liquid.
6. The composition according embodiment 5 wherein said composition is encapsulated in an enteric coating.
7. The composition according to any preceding embodiment, wherein the composition comprises live, attenuated or killed bacteria.
8. The composition according to any preceding embodiment, wherein the composition comprises bacterial spores.
9. The composition according to any of embodiments 1 to 7, wherein the composition is substantially free of bacterial spores.
10. The composition according to any preceding embodiment, wherein the composition comprises bacterial strains that originate from one or more human donor.
11. The composition according to any preceding embodiment, wherein the bacteria are lyophilized.
12. The composition according to any preceding embodiment, wherein the composition comprises at least about 1×103 to 1×1011 CFU of bacteria.
13. A pharmaceutical composition comprising a composition of any of embodiments 1 to 12 and a pharmaceutical carrier.
14. A composition according to any of embodiments 1 to 12 or a pharmaceutical composition of embodiments 14 for use in the treatment of disease.
15. A composition according to any of embodiments 1 to 12 or a pharmaceutical composition of embodiment 14 for use in the treatment of UC or CD.
16. A method for treating UC or CD comprising administering composition according to any of embodiments 1 to 12 or a pharmaceutical composition of embodiment 14 to a subject.
17. The method according to embodiment 16, wherein the composition or pharmaceutical composition is administered by oral administration or rectal administration.
18. A kit comprising a composition according to any of embodiments 1 to 13.
19. A kit comprising:

a sealable container configured to receive a biological sample;

polynucleotide primers for amplifying a 16S rDNA polynucleotide sequence from at least one gut associated bacterium to form an amplified 16S rDNA polynucleotide sequence, wherein the amplified 16S rDNA sequence has at least 97% homology to a polynucleotide sequence selected from SEQ ID NOs 1 to SEQ ID NO 25;

a detecting reagent to detect the amplified 16S rDNA sequence; and instructions for use.

20. A food product or a vaccine comprising the composition of any of embodiments 1 to 12.
21. A method for identifying a faecal donor comprising assessing a faecal sample of a subject for the presence of one or more bacteria selected from Table 1; identifying the faecal donor based on the presence and/or abundance of one or more bacteria selected from Table 1.

22. The use of one or more bacteria selected from Table 1 in a method for identifying a donor for FMT therapy.

23. A method for treating a faecal transplant prior to administration to a subject comprising supplementing the faecal transplant with one or more bacteria selected from Table 1.

The invention is further described in the non-limiting examples.

EXAMPLES

Example 1 Identification and Isolation of Bacterial Isolates

Metagenomic sequencing and bioinformatic analysis was performed on patient and donor samples, across multiple timepoints, from a study which used faecal microbiota transplantation (FMT) to induce and maintain remission in patients with mild to moderate Ulcerative Colitis (Costello et al., 2019). The study demonstrated a 32% clinical remission rate using healthy donor FMT, and a 9% placebo rate using autologous FMT. An accurate microbiome profile was generated for each sample within the study i.e. the relative abundance of each bacterial species in a sample. This accurate profile was generated using Microbiotica's Discovery Platform, notably a proprietary reference genome database.

Using the microbiome profile of both FMT donor material and patient samples, machine learning was used to determine which bacterial species from the donor material engrafted in the recipient and are associated with clinical remission. The selected species were subsequently permuted into different consortia and tested for association with clinical response. The consortium of species which maximised this effect was selected. This therapeutic consortium consists of 10 bacteria ("consortium or composition A").

TABLE 2

Bacteria in Composition A.

| No | Taxonomy | 16s rDNA sequence-sequence identifier | Possible alternative taxonomy: name and/or closely related species based on closely related bacteria identified from public databases, or given name |
|---|---|---|---|
| B1 | *Bifidobacterium adolescentis* | SEQ ID NO. 1<br>SEQ ID NO. 11<br>SEQ ID NO. 16 | na |
| B2 | *Christensenellaceae* R-7 group sp. | SEQ ID NO. 2<br>SEQ ID NO. 14<br>SEQ ID NO. 17 | *Powria foxae*, *Clostridiales bacterium* P40, UBA11524 sp000437595 |
| B3 | *Senegalimassilia anaerobia* | SEQ ID NO. 3<br>SEQ ID NO. 18 | na |
| B4 | *Provetella copri* | SEQ ID NO. 4<br>SEQ ID NO. 12<br>SEQ ID NO. 15<br>SEQ ID NO. 19 | na |
| B5 | *Bifidobacterium pseudocatenulatum* | SEQ ID NO. 5<br>SEQ ID NO. 20 | na |
| B6 | *Eubacterium ventriosum* | SEQ ID NO. 6<br>SEQ ID NO. 21 | na |
| B7 | *Barnesiella intestinihominis* | SEQ ID NO. 7<br>SEQ ID NO. 22 | na |
| B8 | *Bacteroides stercoris* | SEQ ID NO. 8<br>SEQ ID NO. 23 | na |
| B9 | *Roseburia faecis* | SEQ ID NO. 9<br>SEQ ID NO. 13<br>SEQ ID NO. 24 | *Agathobacter faecis*, *Roseburia hominis* |
| B10 | *Slackia isoflavoniconvertens* | SEQ ID NO. 10<br>SEQ ID NO. 25 | na |

na = not available

Bacterial species are listed above in order of statistical significance.

Example 2 Testing of Consortium A Bacteria in Caco-2 Barrier Assays, Dendritic Cell Activation, and CD4+ T Cell Polarisation Assay Caco-2 Barrier Assays Caco-2 barrier function assays were used to determine the ability of the bacteria to repair the epithelial layer after it has been damaged. In UC, the epithelial barrier of the colon is damaged introducing a positive feedback pro-inflammatory state. This is a key mechanism in treating UC alongside immune modulation and decolonisation of pathogenic species. The bacteria in Composition A (table 1), with the exception of *Bacteroides stercoris* (SEQ ID NO. 8), were evaluated for their capacity to restore epithelial integrity, following disruption caused by incubation with lipopolysaccharides (LPS). Epithelial barrier integrity was assessed by measuring the electrical resistance of the Caco2 cells monolayer, in the presence or absence of the bacteria. Declining electric resistance implies disruptions in the monolayer and compromised barrier function, as observed with LPS. Interestingly, most of the bacteria reversed the LPS-induced damage and restored epithelial integrity. *Faecalibacterium prausnitzii* was used as a positive control, known to protect epithelial integrity, whereas *Salmonella typhimurium* was used as a negative control, known to compromise epithelial integrity. All data were normalized to the time when bacteria was added and depicted as mean±SEM (3 independent experiments for every bacterium). As shown in FIG. 1, *Bifidobacterium adolescentis*, Christensenellaceae R-7 group sp., *Senegalimassilia anaerobia, Provetella copri, Barnesiella intestinihominis, Eubacterium ventriosum*, and *Roseburia faecis*, increased electrical resistance compared to the LPS-alone treated cells, indicating restoration of barrier integrity. For species *Bifidobacterium adolescentis, Provetella copri*, and *Roseburia faecis* SEQ IDs 11, 12 and 13 respectively were used.

Barrier repair experiments were also performed with several Compositions, where the bacteria in the Composition were mixed together prior to exposure to a Caco2 monolayer conditioned with LPS. Compositions A, B, G and H were tested (Tables 2, 3, 7 and 8). In compositions A and B, for species *Bifidobacterium adolescentis, Provetella copri*, and *Roseburia faecis* SEQ IDs 11, 12 and 13 respectively were used. Compositions A, B, G and H all increased electrical resistance, compared to the LPS-alone treated cells, indicating restoration of barrier integrity (data not shown).

Figure 2:
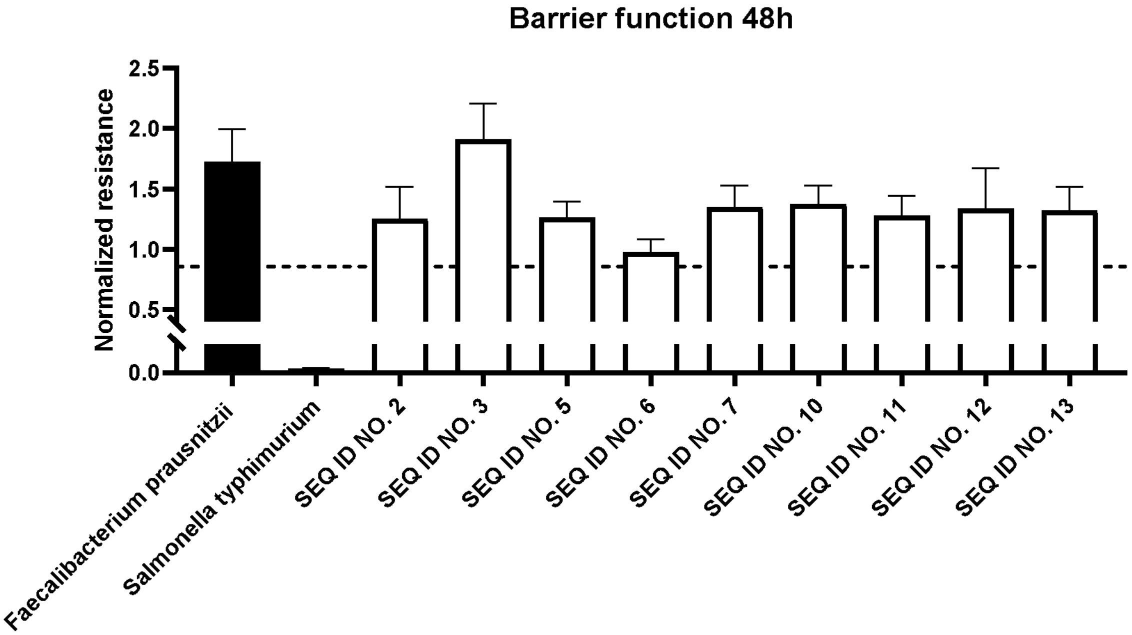
FIG. 2. Caco-2 barrier integrity assay. The results of this assay show that the isolated bacteria maintain epithelial barrier integrity under steady state conditions.

The ability of the bacteria to affect barrier integrity was also assessed. In this case, the Caco-2 monolayers were not exposed to LPS to cause damage. Caco-2 monolayers were established prior to exposure to the bacteria in Composition A, with the exception of *Bacteroides stercoris*. For species *Bifidobacterium adolescentis, Provetella copri*, and *Roseburia faecis* SEQ IDs 11, 12 and 13 respectively were used. *F. prausnitzii* and *S. typhimurium* were used as positive and negative controls, respectively. All data were normalized against the values for un-treated cells, prior to bacterial exposure, and depicted as mean±SEM (3 independent experiments for each bacterium) (FIG. 2). Improvements in barrier function, as seen by increased electrical resistance, were seen for Christensenellaceae R-7 group sp., *Senegalimassilia anaerobia, Bifidobacterium pseudocatenulatum, Barnesiella intestinihominis, Slackia isoflavoniconvertans, Bifidobacterium adolescentis, Prevotella copri* and *Roseburia faecis*. Barrier function experiments were also performed with several Compositions, where the bacteria in the Compositions were mixed together prior to exposure to a Caco2 monolayer. Compositions A, B and C (Table 2, 3, and 4) all caused an improvement in barrier function, as seen by increased electrical resistance. In composition A, for species *Bifidobacterium adolescentis, Provetella copri*, and *Roseburia faecis* SEQ IDs 11, 12 and 13 respectively were used.

Dendritic Cell Activation Assay

Figure 3:
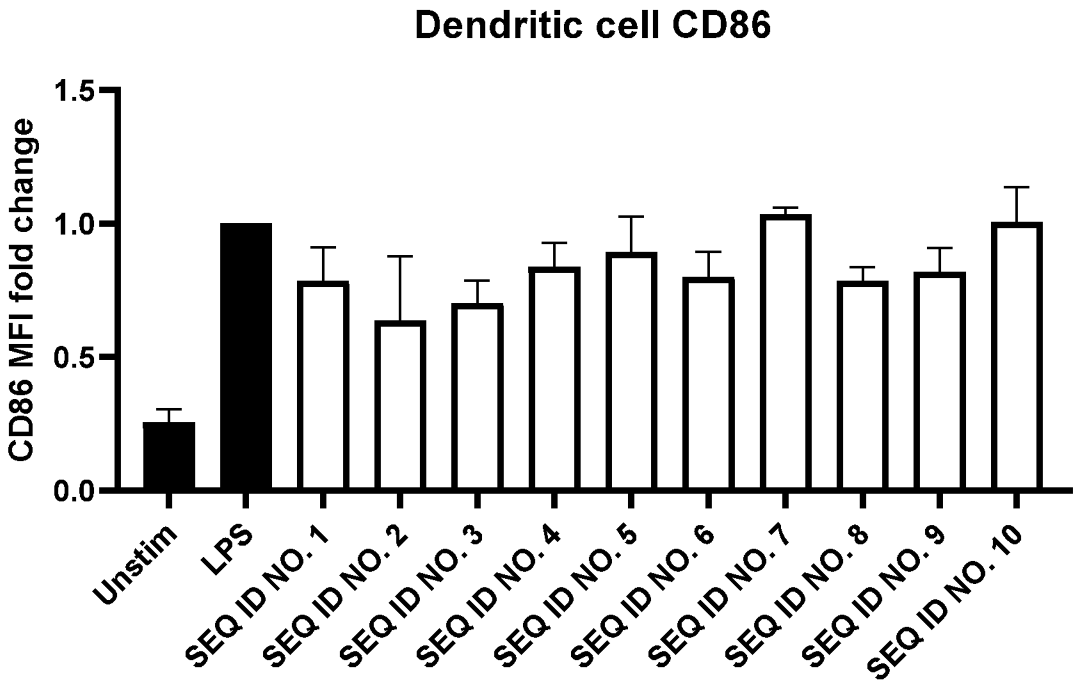
FIG. 3. Dendritic cell activation assay. The results of this assay show that certain bacteria can inhibit LPS-induced dendritic cell maturation, as reflected by lower expression levels of the co-stimulatory molecule CD86.

Dendritic cells (DCs) are key innate antigen presenting cells that play an important role in orchestrating T cell responses. Therefore, the effect of each of the 10 bacteria in Composition A on the maturation of DCs was assessed. For species *Bifidobacterium adolescentis, Provetella copri*, and *Roseburia faecis* SEQ IDs 1, 4 and 9 respectively were used. The capacity of the bacteria to inhibit lipopolysaccharides (LPS)-induced expression of the DC maturation marker CD86, a pro-inflammatory state, was determined. Reduction in the marker CD86 when compared with LPS stimulation alone is indicative of immunosuppression. Expression was determined by flow cytometry. Unstimulated (Unstim) DCs were used as a negative control. All data were normalized against the LPS condition and depicted as mean±SEM (cells were derived from 4 different donors for every bacterium). As seen in FIG. 3, *Bifidobacterium adolescentis*, Christensenellaceae R-7 group sp., *Senegalimassilia anaerobia, Provetella copri, Eubacterium ventriosum, Bacteroides stercoris*, and *Roseburia faecis*, decrease CD86 levels, a dendritic cell maturation marker, below what is observed when exposed to LPS alone. These reductions in CD86 levels are indicative of these bacterial species having an immunosuppressive effect in the presence of LPS (inflammatory state).

Macrophage Assay

Figure 4:
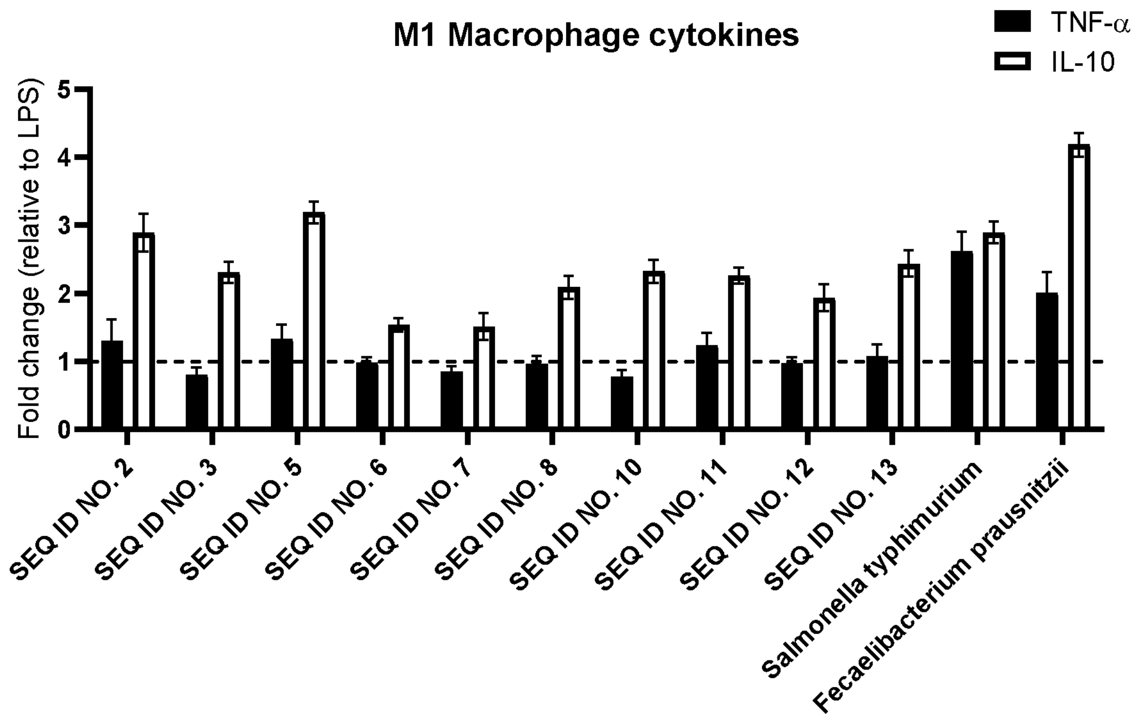
FIG. 4. M1 macrophage cytokine production assay. The results of this assay show that the isolated bacteria modify the cytokine production profile by enhancing the production of the tolerogenic cytokine IL-10, while keeping TNF-α levels similar to the LPS control.

Macrophages in the lamina propria, below the gut epithelial barrier, can be a major source of the pro-inflammatory cytokine TNF-α in the innate immune response (Bujko et al, 2018). Skewing cytokine production of these inflammatory M1 macrophages away from TNF-α production towards elevated production of the immune tolerogenic IL-10 would be a key objective of any new therapeutic. The ability of the bacterial strains in Composition A to stimulate cytokine production in macrophages was assessed. For species *Bifidobacterium adolescentis, Provetella copri*, and *Roseburia faecis* SEQ IDs 11, 12 and 13 respectively were used. Briefly, human monocytes were differentiated into macrophages using macrophage colony stimulating factor (MCSF), and then exposed to bacteria. Further differentiation into pro-inflammatory M1 macrophages was stimulated by the addition of LPS and IFN-γ. The production of TNF-α and the immune-modulatory cytokine IL-10 was assessed by ELISA, and expressed as a fold change relative to the levels induced by LPS. The data are shown in FIG. 4. The inflammatory control strain, *S. typhimurium*, stimulated the M1 macrophages to produce similarly increased levels of both TNF-α and IL-10 as compared to LPS. In contrast the immunomodulatory control strain, *F. prausnitzii*, stimulated the production of a higher fold increase in IL-10 than TNF-α relative to LPS. None of the bacterial strains in Composition A stimulated production of significantly more TNF-α than LPS, whilst they all stimulated 1.5-3-fold more IL-10 (FIG. 4). This shows that these strains skew the cytokine balance from human macrophages towards IL-10, and therefore more immunomodulatory.

Figure 5:
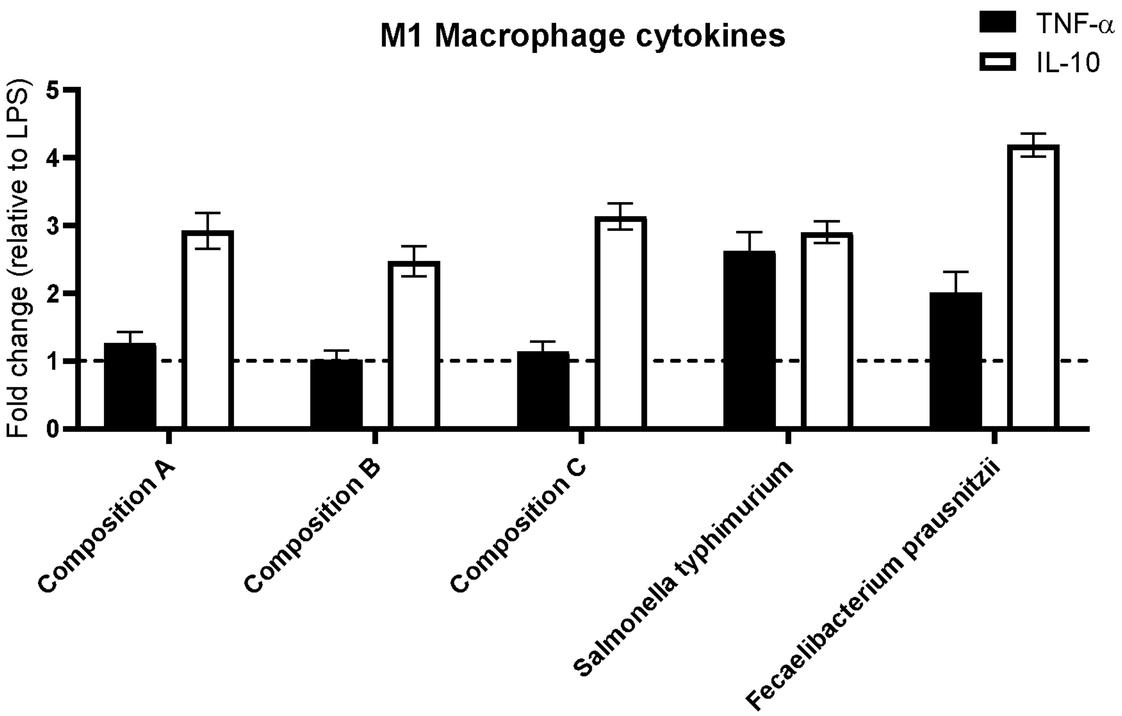
FIG. 5. M1 macrophage cytokine production assay. The results of this assay show that certain compositions of the isolated bacteria modify the cytokine production profile by enhancing the production of the tolerogenic cytokine IL-10, while keeping TNF-α levels similar to the LPS control.

Further macrophage assays were performed as described above, except that bacteria where incubated with macrophage cells as consortia, i.e. all the bacteria where mixed together and then mixed with the macrophages. This was performed for Compositions A, B and C (Tables 2, 3 and 4). In compositions A and B, for species *Bifidobacterium adolescentis, Provetella copri*, and *Roseburia faecis* SEQ IDs 11, 12 and 13 respectively were used. Separately, the control strains *F. prausnitzii* and *S. typhimurium* were assessed. A similar trend was seen as that observed for the individual strains, as the consortia stimulated more IL-10 production but similar levels of TNF-α as compared to LPS. Again, the inflammatory control strain *S. typhimurium* stimulated the production of more of both the cytokines from the M1 macrophages (FIG. 5). This shows that Compositions A, B and C skew the cytokine balance from human macrophages towards IL-10, and therefore more immunomodulatory.

CD4+ T Cell Polarisation Assay

Figure 6:
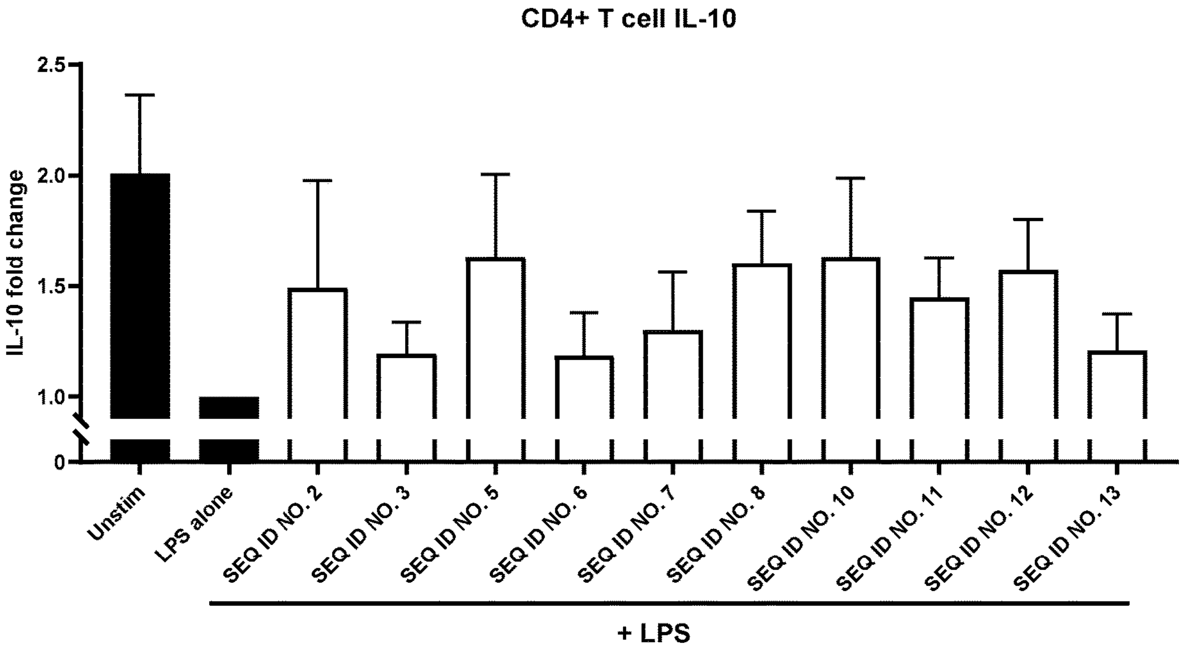
FIG. 6. CD4+ T cell polarisation assay. The results of this assay show that dendritic cells treated with the isolated bacteria in addition to LPS can polarize CD4+ T cells into IL-10 producing effector cells.

Certain T cell populations are important for immunosuppression. Regulatory T cells (Treg) are a key repressive part of the adaptive immune system and have an important role in maintaining immune homeostasis with the microbial communities of the gut (Pandiyan et al, 2019). Increasing the Treg population or enhancing its functionality could re-establish immune balance in IBD patients. Activation of memory T cells using DCs exposed to LPS with or without the bacteria in Composition A was assessed. Briefly, DCs were exposed to LPS and the bacteria in Composition A, the bacteria and LPS then removed and the primed DCs incubated with memory CD4+ T cells, with cytokine production assessed after 11 days of co-incubation. For species *Bifidobacterium adolescentis, Provetella copri*, and *Roseburia faecis* SEQ IDs 11, 12 and 13 respectively were used. FIG. 6 shows the fold-change in IL10 production in CD4+ T cells which have been polarized by LPS-activated DCs, where the DCs have also been exposed to the bacteria in Composition A; fold change is measured relative to the same T cells incubated with LPS-exposed DCs. LPS treatment of DCs inhibited their capacity to prime IL-10-producing CD4+ T cells, as compared to unstimulated DCs. However, exposing LPS-treated DCs to the isolated bacteria increased IL-10 levels, suggesting all species in Composition A reversed the LPS-inhibition of IL-10 production by CD4+ T cells. Such increases in IL-10 production are indicative of expansion of immunomodulatory Tr1 type of Tregs or differentiation of CD4+ T cells into Tr1 cells (Roncarolo et al, 2014).

Figure 7:
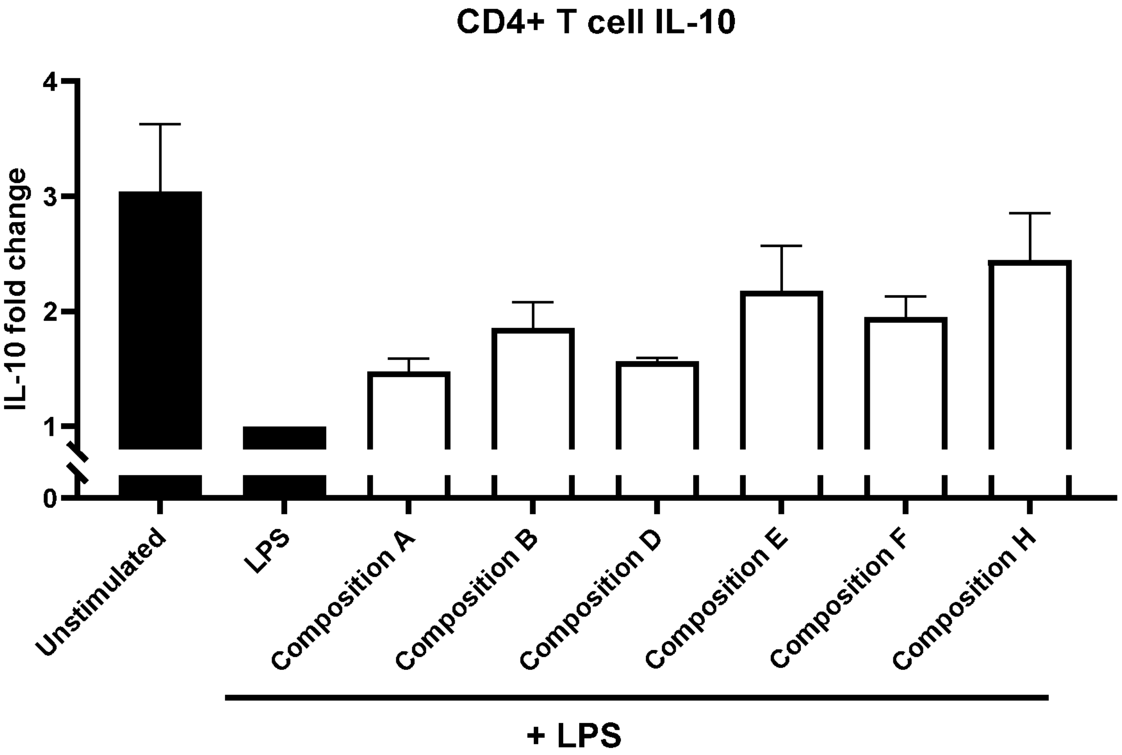
FIG. 7. CD4+ T cell polarisation assay. The results of this assay show that dendritic cells treated with certain compositions of the isolated bacteria can in addition to LPS polarize CD4+ T cells into IL-10 producing effector cells.

Several compositions were assessed where the DCs were exposed to all the bacteria from the composition simultaneously. Composition A, B, D, E, F and H (Tables 2, 3, 5, 6, 7 and 9) were tested. For Composition A and B, for species *Bifidobacterium adolescentis, Provetella copri*, and *Roseburia faecis* SEQ IDs 11, 12 and 13 respectively were used. When the consortium and LPS-exposed DCs were incubated with memory T cells, a significant increase in IL10 production was seen for each consortium relative to T cells co-cultured with DCs exposed to LPS only. This indicates that each consortium was able to induce expansion of or differentiation into immunomodulatory Tr1 type of Tregs (FIG. 7).

Figure 8:
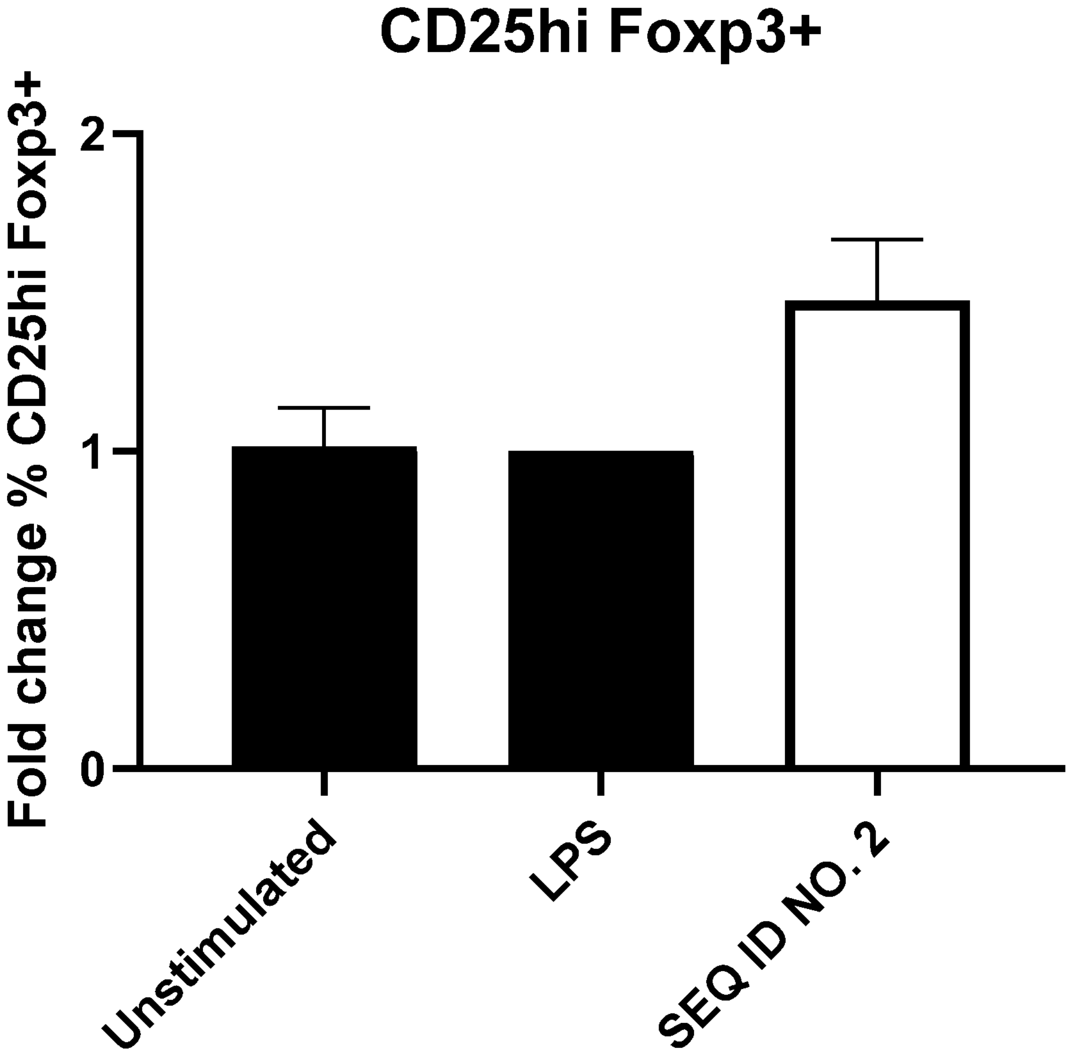
FIG. 8. CD4+ T cell polarisation assay. The results of this assay show that dendritic cells treated with SEQ ID NO. 2 in addition to LPS can polarize CD4+ T cells into Foxp3-expressing effector cells.

The transcription factor Foxp3 is a key marker of classical Tregs (Yagi et al., 2004). DCs were exposed to Christensenellaceae R-7 group sp. with LPS as described above and following co-incubation with CD4+ T cells, the fold change in the expression of FoxP3 was measured (FIG. 8). Data depicted as mean±SEM of 8 independent experiments. Christensenellaceae R-7 group sp. increased the frequency of CD25hi Foxp3+ regulatory T cells.

Overall, these data imply that the isolated bacteria expand or give rise to two types of regulatory T cells: Foxp3+ Tregs, as well as Tr1 type of Tregs, which exert immune suppression in the context of ulcerative colitis through different mechanisms (van Herk et al, 2016).

A summary of the activities attributed to the bacterial species in Table 2 in mammalian cell assays is given in Table 10.

TABLE 3

Bacteria in Composition B.

| No | Taxonomy | 16s rDNA sequence-sequence identifier |
|---|---|---|
| B1 | *Bifidobacterium adolescentis* | SEQ ID NO. 1, SEQ ID NO. 11 |
| B3 | *Senegalimassilia anaerobia* | SEQ ID NO. 3 |
| B4 | *Provetella copri* | SEQ ID NO. 4, SEQ ID NO. 12 |
| B5 | *Bifidobacterium pseudocatenulatum* | SEQ ID NO. 5 |
| B6 | *Eubacterium ventriosum* | SEQ ID NO. 6 |
| B7 | *Barnesiella intestinihominis* | SEQ ID NO. 7 |
| B8 | *Bacteroides stercoris* | SEQ ID NO. 8 |
| B9 | *Roseburia faecis* | SEQ ID NO. 9, SEQ ID NO. 13 |
| B10 | *Slackia isoflavoniconvertens* | SEQ ID NO. 10 |

TABLE 4

Bacteria in Composition C.

| No | Taxonomy | 16s rDNA sequence-sequence identifier |
|---|---|---|
| B1 | *Bifidobacterium adolescentis* | SEQ ID NO. 11 |
| B2 | *Christensenellaceae* R-7 group sp. | SEQ ID NO. 2 |
| B3 | *Senegalimassilia anaerobia* | SEQ ID NO. 3 |
| B4 | *Provetella copri* | SEQ ID NO. 12 |
| B5 | *Bifidobacterium pseudocatenulatum* | SEQ ID NO. 5 |
| B7 | *Barnesiella intestinihominis* | SEQ ID NO. 7 |
| B8 | *Bacteroides stercoris* | SEQ ID NO. 8 |
| B10 | *Slackia isoflavoniconvertens* | SEQ ID NO. 10 |

TABLE 5

Bacteria in Composition D.

| No | Taxonomy | 16s rDNA sequence-sequence identifier |
|---|---|---|
| B1 | *Bifidobacterium adolescentis* | SEQ ID NO. 11 |
| B2 | *Christensenellaceae* R-7 group sp. | SEQ ID NO. 2 |
| B3 | *Senegalimassilia anaerobia* | SEQ ID NO. 3 |
| B4 | *Provetella copri* | SEQ ID NO. 12 |
| B5 | *Bifidobacterium pseudocatenulatum* | SEQ ID NO. 5 |
| B6 | *Eubacterium ventriosum* | SEQ ID NO. 6 |
| B7 | *Barnesiella intestinihominis* | SEQ ID NO. 7 |
| B8 | *Bacteroides stercoris* | SEQ ID NO. 8 |
| B10 | *Slackia isoflavoniconvertens* | SEQ ID NO. 10 |

TABLE 6

Bacteria in Composition E.

| No | Taxonomy | 16s rDNA sequence-sequence identifier |
|---|---|---|
| B1 | *Bifidobacterium adolescentis* | SEQ ID NO. 11 |
| B2 | *Christensenellaceae* R-7 group sp. | SEQ ID NO. 2 |
| B3 | *Senegalimassilia anaerobia* | SEQ ID NO. 3 |
| B4 | *Provetella copri* | SEQ ID NO. 12 |
| B5 | *Bifidobacterium pseudocatenulatum* | SEQ ID NO. 5 |
| B7 | *Barnesiella intestinihominis* | SEQ ID NO. 7 |
| B8 | *Bacteroides stercoris* | SEQ ID NO. 8 |
| B9 | *Roseburia faecis* | SEQ ID NO.13 |
| B10 | *Slackia isoflavoniconvertens* | SEQ ID NO. 10 |

TABLE 7

Bacteria in Composition F.

| No | Taxonomy | 16s rDNA sequence-sequence identifier |
|---|---|---|
| B1 | *Bifidobacterium adolescentis* | SEQ ID NO. 11 |
| B2 | *Christensenellaceae* R-7 group sp. | SEQ ID NO. 2 |
| B3 | *Senegalimassilia anaerobia* | SEQ ID NO. 3 |
| B4 | *Provetella copri* | SEQ ID NO. 12 |
| B7 | *Barnesiella intestinihominis* | SEQ ID NO. 7 |
| B10 | *Slackia isoflavoniconvertens* | SEQ ID NO. 10 |

TABLE 8

Bacteria in Composition G.

| No | Taxonomy | 16s rDNA sequence-sequence identifier |
|---|---|---|
| B2 | *Christensenellaceae* R-7 group sp. | SEQ ID NO. 2 |
| B3 | *Senegalimassilia anaerobia* | SEQ ID NO. 3 |
| B4 | *Provetella copri* | SEQ ID NO. 12 |
| B7 | *Barnesiella intestinihominis* | SEQ ID NO. 7 |

TABLE 9

Bacteria in Composition H.

| No | Taxonomy | 16s rDNA sequence-sequence identifier |
|---|---|---|
| B3 | *Senegalimassilia anaerobia* | SEQ ID NO. 3 |
| B4 | *Provetella copri* | SEQ ID NO. 12 |
| B7 | *Barnesiella intestinihominis* | SEQ ID NO. 7 |

TABLE 10

Summary of species activity in cell assays.

| No | Patent Taxonomy | SEQ ID NO | Repair epithelial barrier (Caco2) | Improves Barrier Function (Caco2) | Decrease DC Maturation | M1 Macrophage (increased IL10:TNFα) | Induce Tr1 Regulatory T cells | Induce Foxp3+ Regulatory T cells |
|---|---|---|---|---|---|---|---|---|
| B1 | *Bifidobacterium adolescentis* | 11, 1 (DC only) | Yes | Yes | Yes | Yes | Yes | |
| B2 | *Christensenellaceae* R-7 group sp. | 2 | Yes | Yes | Yes | Yes | Yes | Yes |
| B3 | *Senegalimassilia anaerobia* | 3 | Yes | Yes | Yes | Yes | Yes | |
| B4 | *Provetella copri* | 12, 4 (DC only) | Yes | Yes | Yes | Yes | Yes | |
| B5 | *Bifidobacterium pseudocatenulatum* | 5 | | Yes | | Yes | Yes | |
| B6 | *Eubacterium ventriosum* | 6 | Yes | | Yes | Yes | Yes | |
| B7 | *Barnesiella intestinihominis* | 7 | Yes | Yes | | Yes | Yes | |
| B8 | *Bacteroides stercoris* | 8 | | | Yes | Yes | Yes | |
| B9 | *Roseburia faecis* | 13, 9 (DC only) | Yes | Yes | Yes | Yes | Yes | |
| B10 | *Slackia isoflavoniconvertens* | 10 | | Yes | | Yes | Yes | |

Example 3 Testing of Composition B in the DSS-Induced Colitis Model

An effective, and widely used, murine model in IBD research is the DSS-induced (dextran sodium sulphate) colitis model due to its rapidity, simplicity, and controllability (Kiesler, Fuss and Strober, 2015). In this disease model, mice are exposed to DSS in their drinking water which induces epithelial cell damage resulting in localised inflammation and development of a colitis phenotype. The DSS model has many features that are characteristic of UC (rectum to colon location, extensive epithelial damage and superficial inflammation). Moreover, this model also has some features of Crohn's disease, including weight loss.

Male specific pathogen free (SPF) C57/BL6N mice, approximately 6 weeks old, were used throughout. The mice were pre-conditioned to remove the commensal microbiome for 4 days with an antibiotic cocktail of kanamycin (0.4 mg/ml), colistin sulphate (850 U/ml), gentamicin sulphate (0.035 mg/ml), metronidazole (0.215 mg/ml), vancomycin (0.045 mg/ml), ciprofloxacin (0.156 mg/ml), and ampicillin (0.1 mg/ml) prepared in sterile drinking water until the day before bacterial therapy (LBT). Mice were able to drink the antibiotic containing water ad libitum. Mice were returned to drinking water free of antibiotics for 4-6 days (depending on treatment group) prior to addition of DSS. DSS was administered at 2% within sterile drinking water for 7 days and replaced with sterile water only for the remaining duration of the study.

Mice were treated with two dosing schedules of Composition B, dosing schedule 1 starting on day −5 (D-5) with 5 daily doses until D-1 and a final dose on D2. The start of DSS treatment was Day 0. Dosing schedule 2 included 7 daily doses of Composition B from D-3 to D3. Each daily dose of Composition B was administered by oral gavage in vehicle buffer at 1-2×$10^7$ cfu. For species *Bifidobacterium adolescentis, Provetella copri*, and *Roseburia faecis* in Composition B, SEQ IDs 1, 4 and 9 respectively were used.

Following DSS administration, mice were monitored for daily weight loss from D7 to D10 as a primary parameter of colitis phenotype. Mice found with weight loss greater than 20%, severe wet tail, diarrhoea, hypothermia, lying prone or unresponsive were euthanised and the time of death together with clinical condition recorded. The study endpoint was 10 days following administration of DSS where final mouse weight, colon length, and tissue samples were taken and recorded.

Figure 9:
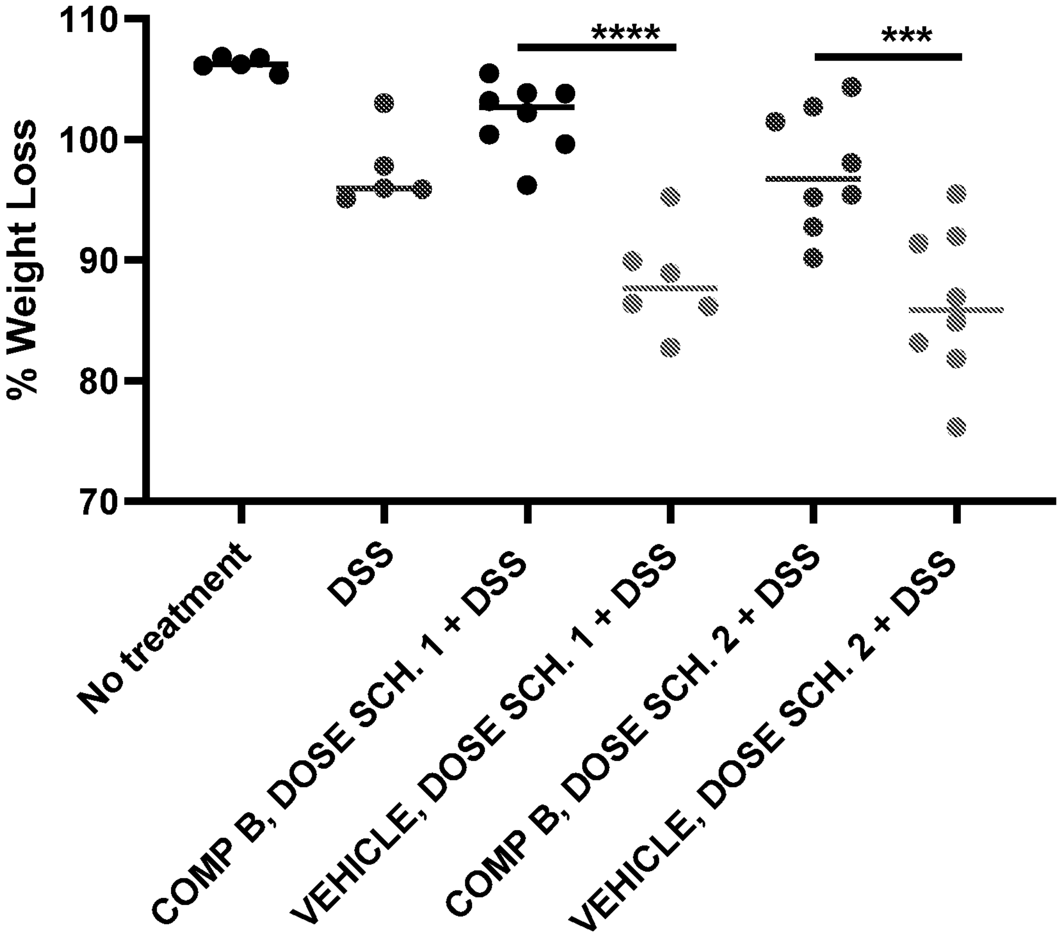
FIG. 9. Composition B reduced disease-induced weight-loss in SPF DSS-induced Colitis Disease Model. Mice were treated with DSS alone or in combination with either vehicle control or Composition B at two dosing schedules. Data depicted as mean percentage weight-loss of individual mice±SEM at D8. Both treatment groups showed superior efficacy compared to vehicle treated mice as weight loss was prevented (One-way ANOVA $p<0.002$).
Figure 10:
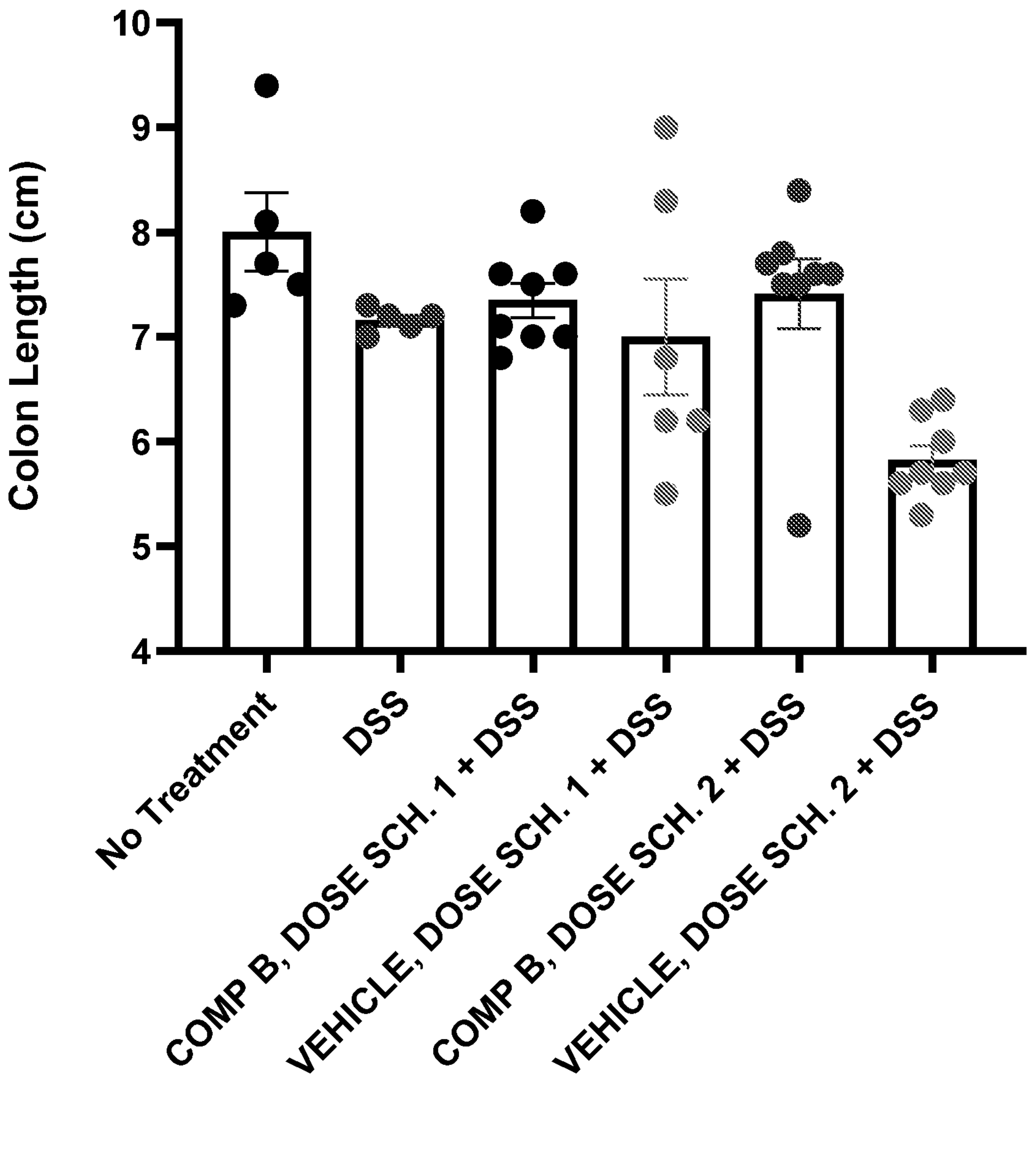
FIG. 10. Composition B treatment reduces disease-induced colon shortening in SPF-induced Colitis Disease Model. Colon length was measured in cm at D10 in SPF DSS-induced Colitis Disease Model Treated with Composition B. Mice were treated with DSS alone or in combination with either vehicle control or Composition B at two dosing schedules. Data depicted as mean length in cm±SEM of individual mice.

Weight loss results are shown in FIG. 9, for Day 8 post DSS treatment. The efficacy of the two Composition B dosing schedules was tested in comparison to their relevant vehicle control, and in comparison to each other. Both treatment groups showed superior efficacy compared to vehicle treated mice as weight loss was prevented (One-way ANOVA $p<0.002$). No significant difference was found between the two doing schedules. This demonstrates both treatment schedules were efficacious, and Composition B prevented weight loss resulting from DSS-induced murine colitis. This shows that Composition B reduces disease severity in a DSS-induced colitis disease model.

Figure 11:
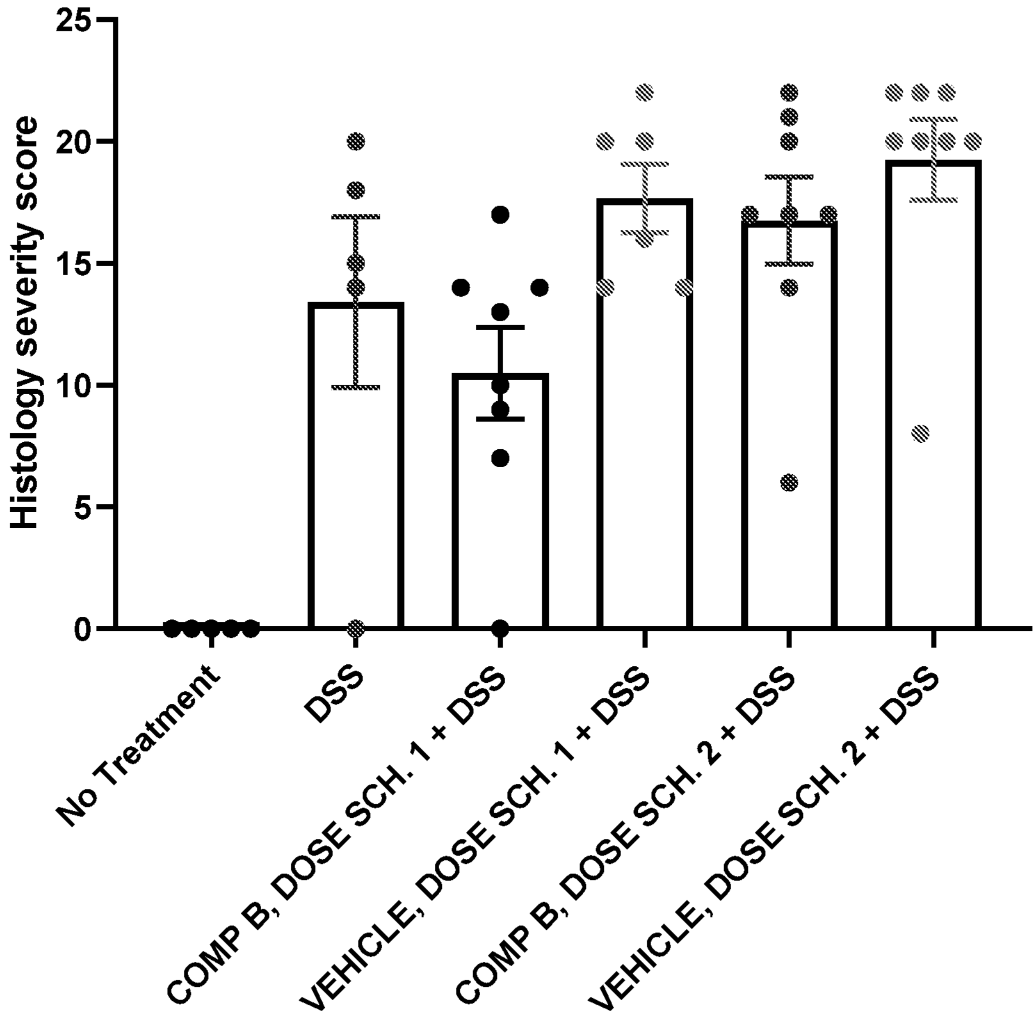
FIG. 11. Composition B treatment reduces colonic inflammation in SPF-induced Colitis Disease Model. Colonic inflammation was assessed by histological analysis. Mice were treated with DSS alone or in combination with either vehicle control or Composition B at two dosing schedules. Colon specimens were excised on D10 and scored using Mouse Colitis Histology Index (Koelnik et al 2018). Data depicted as histology severity score±SEM of individual mice.

Colon length, together with colonic inflammation determined by histological analysis, was assessed on ex vivo colons recovered by dissection on day 10 of the study. Colon specimens were fixed with formalin and sections (4 μm) were stained with haematoxylin/eosin. Pathology was scored using Mouse Colitis Histology Index (Koelnik et al 2018). Inflammation in the colon leads to the reduction of colon length. In mice treated with both Composition B dosing schedules, colon length was longer than in the mice treated with vehicle, indicating that Composition B treatment reduced colonic inflammation (Figure Histology severity scoring of colon sections from mice treated with Composition B bacteria (both dosing schedules) was lower than that observed for the respective vehicle treated groups, again indicating that Composition B treatment reduced inflammation in the colon (FIG. 11). The effect on colon length and histology score caused by Composition B dosing shows that Composition B reduces disease severity in a DSS-induced colitis disease model.

TABLE 11

| Sequences |
| --- |
| SEQ ID NO 11 *Bifidobacterium adolescentis*<br>TGTGGAGGGTTCGATTCTGGCTCAGGATGAACGCTGGCGGCGTGCTTAACACATGCAAGT<br>CGAACGGGATCCCAGGAGCTTGCTCCTGGGTGAGAGTGGCGAACGGGTGAGTAATGCGTG<br>ACCGACCTGCCCCATACACCGGAATAGCTCCTGGAAACGGGTGGTAATGCCGGATGCTCC<br>AGTTGACCGCATGGTCCTCTGGGAAAGCTTTTGCGGTATGGGATGGGGTCGCGTCCTATC<br>AGCTTGATGGCGGGGTAACGGCCCACCATGGCTTCGACGGGTAGCCGGCCTGAGAGGGCG<br>ACCGGCCACATTGGGACTGAGATACGGCCCAGACTCCTACGGGAGGCAGCAGTGGGGAAT<br>ATTGCACAATGGGCGCAAGCCTGATGCAGCGACGCCGCGTGCGGGATGACGGCCTTCGGG<br>TTGTAAACCGCTTTTGACTGGGAGCAAGCCCTTCGGGGTGAGTGTACCTTTCGAATAAGC<br>ACCGGCTAACTACGTGCCAGCAGCCGCGGTAATACGTAGGGTGCAAGCGTTATCCGGAAT<br>TATTGGGCGTAAAGGGCTCGTAGGCGGTTCGTCGCGTCCGGTGTGAAAGTCCATCGCTTA<br>ACGGTGGATCCGCGCCGGGTACGGGCGGGCTTGAGTGCGGTAGGGGAGACTGGAATTCCC<br>GGTGTAACGGTGGAATGTGTAGATATCGGGAAGAACACCAATGGCGAAGGCAGGTCTCTG<br>GGCCGTCACTGACGCTGAGGAGCGAAAGCGTGGGGAGCGAACAGGATTAGATACCCTGGT<br>AGTCCACGCCGTAAACGGTGGATGCTGGATGTGGGGACCATTCCACGGTCTCCGTGTCGG<br>AGCCAACGCGTTAAGCATCCCGCCTGGGGAGTACGGCCGCAAGGCTAAAACTCAAAGAAA<br>TTGACGGGGGCCCGCACAAGCGGCGGAGCATGCGGATTAATTCGATGCAACGCGAAGAAC<br>CTTACCTGGGCTTGACATGTTCCCGACAGCCCCAGAGATGGGGCCTCCCTTCGGGGGGGG<br>TTCACAGGTGGTGCATGGTCGTCGTCAGCTCGTGTCGTGAGATGTTGGGTTAAGTCCCGC<br>AACGAGCGCAACCCTCGCCCTGTGTTGCCAGCACGTCGTGGTGGGAACTCACGGGGGACC<br>GCCGGGGTCAACTCGGAGGAAGGTGGGGATGACGTCAGATCATCATGCCCCTTACGTCCA<br>GGGCTTCACGCATGCTACAATGGCCGGTACAACGGGATGCGACACCGCGAGGTGGAGCGG<br>ATCCCTTAAAACCGGTCTCAGTTCGGATTGGAGTCTGCAACCCGACTCCATGAAGGCGGA<br>GTCGCTAGTAATCGCGGATCAGCAACGCCGCGGTGAATGCGTTCCCGGGCCTTGTACACA<br>CCGCCCGTCAAGTCATGAAAGTGGGTAGCACCCGAAGCCGGTGGCCCAACCTTTTTGGGG<br>GGAGCCGTCTAAGGTGAGACTCGTGATTGGGACTAAGTCGTAACAAGGTAGCCGTACCGG<br>AAGGTGCGGCTGGATCACCTCCTTT |
| SED ID NO 7 *Barnesiella intestinihominis*<br>CGAAGAGTTTGATCCTGGCTCAGGATGAACGCTAGCGACAGGCCTAACACATGCAAGTCG<br>AGGGGCAGCGGAGAGGTAGCAATACCTTTGCCGGCGACCGGCGCACGGGTGAGTAACACG<br>TATGCAATCCACCTGTAACAGGGGGATAACCCGGAGAAATCCGGACTAATACCCCATAAT<br>ATGGGCGCTCCGCATGGAGAGTCCATTAAAGAGAGCAATTTTGGTTACAGACGAGCATGC<br>GCTCCATTAGCCAGTTGGCGGGGTAACGGCCCACCAAAGCGACGATGGATAGGGGTTCTG<br>AGAGGAAGGTCCCCCACATTGGAACTGAGACACGGTCCAAACTCCTACGGGAGGCAGCAG<br>TGAGGAATATTGGTCAATGGTCGGCAGACTGAACCAGCCAAGTCGCGTGAGGGAAGACGG<br>CCCTACGGGTTGTAAACCTCTTTTGTCGGAGAGTAAAGTACGCTACGTGTAGTGTATTGC<br>AAGTATCCGAAGAAAAAGCATCGGCTAACTCCGTGCCAGCAGCCGCGGTAATACGGAGGA<br>TGCGAGCGTTATCCGGATTTATTGGGTTTAAAGGGTGCGTAGGCGGCACGCCAAGTCAGC<br>GGTGAAATTTCCGGGCTCAACCCGGACTGTGCCGTTGAAACTGGCGAGCTAGAGTGCACA<br>AGAGGCAGGCGGAATGCGTGGTGTAGCGGTGAAATGCATAGATATCACGCAGAACCCCGA<br>TTGCGAAGGCAGCCTGCTAGGGTGCGACAGACGCTGAGGCACGAAAGCGTGGGTATCGAA<br>CAGGATTAGATACCCTGGTAGTCCACGCAGTAAACGATGAATACTAACTGTTTGCGATAC<br>AATGTAAGCGGTACAGCGAAAGCGTTAAGTATTCCACCTGGGGAGTACGCCGGCAACGGT<br>GAAACTCAAAGGAATTGACGGGGGCCCGCACAAGCGGAGGAACATGTGGTTTAATTCGAT<br>GATACGCGAGGAACCTTACCCGGGCTCAAACGCAGGGGGAATGCCGGTGAAAGTCGGCAG<br>CTAGCAATAGTCACCTGCGAGGTGCTGCATGGTTGTCGTCAGCTCGTGCCGTGAGGTGTC<br>GGCTTAAGTGCCATAACGAGCGCAACCCCTATGGACAGTTACTAACGGGTGAAGCCGAGG<br>ACTCTGTCTAGACTGCCGGCGCAAGCCGCGAGGAAGGTGGGGATGACGTCAAATCAGCAC<br>GGCCCTTACGTCCGGGGCGACACACGTGTTACAATGGCAGGTACAGAAGGCAGCCAGTCA<br>GCAATGACGCGCGAATCCCGAAAACCTGTCTCAGTTCGGATTGGAGTCTGCAACCCGACT<br>CCATGAAGCTGGATTCGCTAGTAATCGCGCATCAGCCATGGCGCGGTGAATACGTTCCCG<br>GGCCTTGTACACACCGCCCGTCAAGCCATGGAAGCCGGGAGTACCTGAAGCATGCAACCG<br>CAAGGAGCGTACGAAGGTAATACCGGTAACTGGGGCTAAGTCGTAACAAGGTAGCCGTAC<br>CGGAAGGTGCGGCTGGAACACCTCCTTT |
| SEQ ID NO 15 *Prevotella copri*<br>ATGGAGAGTTTGATCCTGGCTCAGGATGAACGCTAGCTACAGGCTTAACACATGCAAGTC<br>GAGGGGAAACGACATCGAAAGCTTGCTTTTGATGGGCGTCGACCGGCGCACGGGTGAGTA<br>ACGCGTATCCAACCTGCCCGCCACTTGGGGATAACCTTGCGAAAGTAAGACTAATACCCA<br>ATGATATCTCTAGAAGGCATCTGAAAGAGATTAAAGATTTATCGGTGATGGATGGGGATG<br>CGTCTGATTAGCTTGTTGGCGGGGTAACGGCCCACCAAGGCAACGATCAGTAGGGGTTCT<br>GAGAGGAAGGTCCCCCACATTGGAACTGAGACACGGTCCAAACTCCTACGGGAGGCAGCA<br>GTGAGGAATATTGGTCAATGGACGAGAGTCTGAACCAGCCAAGTAGCGTGCAGGAAGACG<br>GCCCTATGGGTTGTAAACTGCTTTTATAAGGGAATAAAGTGAGTCTCGTGAGACTTTTTG<br>CATGTACCTTATGAATAAGGACCGGCTAATTCCGTGCCAGCAGCCGCGGTAATACGGAAG<br>GTCCGGGCGTTATCCGGATTTATTGGGTTTAAAGGGAGCGTAGGCCGGAGATTAAGCGTG<br>TTGTGAAATGTAGATGCTCAACATCTGAACTGCAGCGCGAACTGGTTTCCTTGAGTACGC<br>ACAAAGTGGGCGGAATTCGTGGTGTAGCGGTGAAATGCTTAGATATCACGAAGAACTCCG<br>ATTGCGAAGGCAGCTCACTGGAGCGCAACTGACGCTGAAGCTCGAAAGTGCGGGTATCGA<br>ACAGGATTAGATACCCTGGTAGTCCGCACGGTAAACGATGGATGCCCGCTGTTGGTCTGA<br>ATAGGTCAGCGGCCAAGCGAAAGCATTAAGCATCCCACCTGGGGAGTACGCCGGCAACGG<br>TGAAACTCAAAGGAATTGACGGGGGCCCGCACAAGCGGAGGAACATGTGGTTTAATTCGA<br>TGATACGCGAGGAACCTTACCCGGGCTTGAATTGCAGAGGAAGGATTTGGAGACAATGAC<br>GCCCTTCGGGGCCTCTGTGAAGGTGCTGCATGGTTGTCGTCAGCTCGTGCCGTGAGGTGT<br>CGGCTTAAGTGCCATAACGAGCGCAACCCCTCTCCTTAGTTGCCATCAGGTGAAGCTGGG<br>CACTCTGGGGACACTGCCACCGTAAGGTGTGAGGAAGGTGGGGATGACGTCAAATCAGCA<br>CGGCCCTTACGTCCGGGGCTACACACGTGTTACAATGGCAGGTACAGAGAGACGGTCCCT |

TABLE 11-continued

Sequences

TGCAAAATGGATCAAATCCTTAAAGCCTGTCTCAGTTCGGACTGGGGTCTGCAACCCGAC
CCCACGAAGCTGGATTCGCTAGTAATCGCGCATCAGCCATGGCGCGGTGAATACGTTCCC
GGGCCTTGTACACACCGCCCGTCAAGCCATGAAAGCCGGGGGCGCCTAAAGTCCGTGACC
GTAAGGAGCGGCCTAGGGCGAAACTGGTAATTGGGGCTAAGTCGTAACAAGGTAGCCGTA
CCGGAAGGTGCGGCTGGAACACCTCCTTT

SEQ ID NO 5 *Bifidobacterium pseudocatenulatum*
TGTGGAGGGTTCGATTCTGGCTCAGGATGAACGCTGGCGGCGTGCTTAACACATGCAAGT
CGAACGGGATCCATCAGGCTTTGCTTGGTGGTGAGAGTGGCGAACGGGTGAGTAATGCGT
GACCGACCTGCCCCATACACCGGAATAGCTCCTGGAAACGGGTGGTAATGCCGGATGCTC
CGACTCCTCGCATGGGGTGTCGGGAAAGATTTCATCGGTATGGGATGGGGTCGCGTCCTA
TCAGGTAGTCGGCGGGGTAACGGCCCACCGAGCCTACGACGGGTAGCCGGCCTGAGAGGG
CGACCGGCCACATTGGGACTGAGATACGGCCCAGACTCCTACGGGAGGCAGCAGTGGGGA
ATATTGCACAATGGGCGCAAGCCTGATGCAGCGACGCCGCGTGCGGGATGACGGCCTTCG
GGTTGTAAACCGCTTTTGATCGGGAGCAAGCCTTCGGGTGAGTGTACCTTTCGAATAAGC
ACCGGCTAACTACGTGCCAGCAGCCGCGGTAATACGTAGGGTGCAAGCGTTATCCGGAAT
TATTGGGCGTAAAGGGCTCGTAGGCGGTTCGTCGCGTCCGGTGTGAAAGTCCATCGCTTA
ACGGTGGATCTGCGCCGGGTACGGGCGGGCTGGAGTGCGGTAGGGGAGACTGGAATTCCC
GGTGTAACGGTGGAATGTGTAGATATCGGGAAGAACACCAATGGCGAAGGCAGGTCTCTG
GGCCGTTACTGACGCTGAGGAGCGAAAGCGTGGGGAGCGAACAGGATTAGATACCCTGGT
AGTCCACGCCGTAAACGGTGGATGCTGGATGTGGGGCCCGTTCCACGGGTTCCGTGTCGG
AGCTAACGCGTTAAGCATCCCGCCTGGGGAGTACGGCCGCAAGGCTAAAACTCAAAGAAA
TTGACGGGGGCCCGCACAAGCGGCGGAGCATGCGGATTAATTCGATGCAACGCGAAGAAC
CTTACCTGGGCTTGACATGTTCCCGACCGCGGCAGAGATGTCGTTTCCCTTCGGGGGGGG
TTCACAGGTGGTGCATGGTCGTCGTCAGCTCGTGTCGTGAGATGTTGGGTTAAGTCCCGC
AACGAGCGCAACCCTCGCCCTGTGTTGCCAGCACGTCATGGTGGGAACTCACGGGGGACC
GCCGGGGTCAACTCGGAGGAAGGTGGGGATGACGTCAGATCATCATGCCCCTTACGTCCA
GGGCTTCACGCATGCTACAATGGCCGGTACAACGGGATGCGACACGGCGACGTGGAGCGG
ATCCCTGAAAACCGGTCTCAGTTCGGATTGGAGTCTGCAACCCGACTCCATGAAGGCGGA
GTCGCTAGTAATCGCGGATCAGCAACGCCGCGGTGAATGCGTTCCCGGGCCTTGTACACA
CCGCCCGTCAAGTCATGAAAGTGGGTAGCACCCGAAGCCGGTGGCCTAACCCTTTGTGGA
TGGAGCCGTCTAAGGTGAGACTCGTGATTGGGACTAAGTCGTAACAAGGTAGCCGTACCG
GAAGGTGCGGCTGGATCACCTCCTTT SEQ ID NO 10 *Slackia isoflavoniconvertans*
CGGAGAGTTTGATCCTGGCTCAGGATGAACGCTGGCGGCGCGCCTAACACATGCAAGTCG
AACGAGTAAGACGCCTTCGGGCGTGGATAGAGTGGCGAACGGGTGAGTAACACGTGACCA
ACCTGCCCCCTCCTCCGGGACAACCTCGGGAAACCGAGGCTAATACCGGATACTCCGGGC
CCCCCGCATGGGGGGCCCGGGAAAGCCCTGGCGGGAGGGGATGGGGTCGCGGCCCATCAG
GTAGACGGCGGGGTAACGGCCCACCGTGCCTGCAACGGGTAGCCGGGCTGAGAGGCCGAT
CGGCCACATTGGGACTGAGACACGGCCCAGACTCCTACGGGAGGCAGCAGTGGGGAATTT
TGCGCAATGGGGGCAACCCTGACGCAGCGACGCCGCGTGCGGGACGAAGTCATTCGTGAC
GTAAACCGCTTTCAGCGAGGAAGAACCATGACGGTACTCGCAGAAGAAGCCCCGGCTAAC
TACGTGCCAGCAGCCGCGGTAATACGTAGGGGGCGAGCGTTATCCGGAATCATTGGGCGT
AAAGCGCGCGCAGGCGGGCTTTCAAGCGGCGGCGTCGAAGCCGGGGGCTCAACCCCCGGA
AGCGCCCCGAACTGGAAGCCTCGGATGCGGCAGGGGGAGGCGGAATTCCCGGTGTAGCGG
TGAAATGCGCAGATATCGGGAAGAACACCGACGGCGAAGGCAGCCTCCTGGGCCGGCATC
GACGCTGAGGCGCGAAAGCTGGGGGAGCGAACAGGATTAGATACCCTGGTAGTCCCAGCC
GTAAACGATGGACGCTAGGTGTGGGGGGATAGGTCCCTCCGTGCCGAAGCCAACGCATTA
AGCGTCCCGCCTGGGGAGTACGGCCGCAAGGCTAAAACTCAAAGGAATTGACGGGGGCCC
GCACAAGCAGCGGAGCATGTGGCTTAATTCGAAGCAACGCGAAGAACCTTACCAGGGCTT
GACATATCGGTGAAGCCGGAGAGATCCGGTGGCCGAGAGGAGCCGATACAGGTGGTGCAT
GGCTGTCGTCAGCTCGTGCCGTGAGGTGTTGGGTTAAGTCCCGCAACGAGCGCAACCCCC
GCCGCGTGTTGCCAGCATTCAGTTGGGCACTCACGCGGGACTGCCGGCGTCAAGCCGGAG
GAAGGCGGGGACGACGTCAAGTCATCATGCCCCTCATGCCCTGGGCCGCACACGTGCTAC
AATGGCCGGCACAACGGGTTGCCACCCCGCGAGGGGGAGCGGATCCCCAAAGCCGGCCCC
AGTTCGGATCGCAGGCTGCAACCCGCCTGCGTGAAGCCGGAGTTGCTAGTAATCGCGGAT
CAGCACGCCGCGGTGAATACGTTCCCGGGCCTTGTACACACCGCCCGTCACACCACCCGA
GTCGTCTGCACCCGAAGCCGCCGGCCGAACCCCTCCGGGGGGCGGAGGCGTCGAAGGTGT
GGAGGGTGAGGGGGGTGAAGTCGTAACAAGGTAGCCGTACCGGAAGGTGCGGCTGGATCA
CCTCCTTT SEQ ID NO 3 *Senegalimassilia anaerobia*
ACGGAGAGTTTGATCCTGGCTCAGGATGAACGCTGGCGGCGTGCCTAACACATGCAAGTC
GAACGATGAAACCGCCCTCGGGCGGACATGAAGTGGCGAACGGGTGAGTAACACGTGACC
GACCTGCCCCCCGCCCAGGGACAGCCCCCCGAAAGGGGGATTAATACCTGGTACTCCGGA
AGCGGCGCATGCCGCATCCGGGAAAGCTTATCGCGGCGGGGGATGGGGTCGCGGCCCATC
AGGTAGACGGCGGGGCGACGGCCCACCGTGCCGACGACGGGTAGCCGGGTTGAGAGACCG
ACCGGCCACATTGGGACTGAGATACGGCCCAGACTCCTACGGGAGGCAGCAGTGGGGAAT
TTTGCGCAATGGGGGCAACCCTGACGCAGCAACGCCGCGTGCGGGACGAAGGCGTCCGCG
TCGTAAACCGCTTTCAGCGGGGAACACTTATCGAGGGTACCCGCAGAAGAAGCCCCGGCT
AAATACGTGCCAGCAGCCGCGGTAATACGTATGGGGCGAGCGTTATCCGGATTCATTGGG
CGTAAAGCGCGCGTAGGCGGAGCGCTAAGCGGGACCTCTAACCCGAGGGCTCAACCCCCG
GCCGGGTCCCGAACTGGCGCTCTCGAGTGCGGTAGGGGAGAGCGGAATTCCCGGTGTAGC
GGTGGAATGCGCAGATATCGGGAAGAACACCGACGGCGAAGGCAGCTCTCTGGGCCGAAA
CTGACGCTGAGGCGCGAAAGCTGGGGGAGCGAACAGGATTAGATACCCTGGTAGTCCCAG
CCGTAAACGATGGGCGCTAGGTGTGGGGGGGAAGACCCCCCGTGCCGCAGCCAACGCATT
AAGCGCCCCGCCTGGGGAGTACGGCCGCAAGGCTAAAACTCAAAGGAATTGACGGGGGCC TABLE 11-continued

| Sequences |
| --- |

CGCACAAGCAGCGGAGCATGTGGCTTAATTCGAAGCAACGCGAAGAACCTTACCAGGGCT
TGACATGCGGGTGAAGCGGCGGAGACGCCGTGGCCGAGAGGAGCCCGCACAGGTGGTGCA
TGGCTGTCGTCAGCTCGTGTCGTGAGATGTTGGGTTAAGTCCCGCAACGAGCGCAACCCC
TGCCCCGTGTTGCCAGCATTCAGTTGGGGACTCGCGGGGGACTGCCGGCGTCAAGCCGGA
GGAAGGTGGGGACGACGTCAAGTCATCATGCCCCTTATGCCCTGGGCCGCACACGTGCTA
CAATGGCCGGTACAGAGGGTTGCGACCCCGCGAGGGGGAGCGGATCCCGCAAAGCCGGCC
CCAGTTCGGATCGGAGGCTGCAACCCGCCTCCGTGAAGCCGGAGTTGCTAGTAATCGCGG
ATCAGCACGCCGCGGTGAATACGTTCCCGGGCCTTGTACACACCGCCCGTCACACCACCC
GAGTCGTCTGCACCCGAAGCCGCCGGCCGAACCCTTTCAGGGGCGGAGGCGTCGAAGGTG
TGGAGGGTGAGGGGGGTGAAGTCGTAACAAGGTAGCCGTACCGGAAGGTGCGGCTGGATC
ACCTCCTTT

SEQ ID NO 12 *Prevotella copri*
ATGGAGAGTTTGATCCTGGCTCAGGATGAACGCTAGCTACAGGCTTAACACATGCAAGTC
GAGGGGAAACGATATTGGAAGCTTGCTTCCGATAGGCGTCGACCGGCGCACGGGTGAGTA
ACGCGTATCCAACCTGCCCACCACTTGGGGATAACCTTGCGAAAGTAAGACTAATACCCA
ATGACGTCTCTAGAAGACATCTGAAAGAGATTAAAGATTTATCGGTGATGGATGGGGATG
CGTCTGATTAGCTTGTTGGCGGGGTAACGGCCCACCAAGGCAACGATCAGTAGGGGTTCT
GAGAGGAAGGTCCCCCACATTGGAACTGAGACACGGTCCAAACTCCTACGGGAGGCAGCA
GTGAGGAATATTGGTCAATGGACGAGAGTCTGAACCAGCCAAGTAGCGTGCAGGATGACG
GCCCTATGGGTTGTAAACTGCTTTTATAAGGGAATAAAGTGAGTCTCGTGAGACTTTTTG
CATGTACCTTATGAATAAGGACCGGCTAATTCCGTGCCAGCAGCCGCGGTAATACGGAAG
GTCCGGGCGTTATCCGGATTTATTGGGTTTAAAGGGAGCGTAGGCCGGAGATTAAGCGTG
TTGTGAAATGTAGACGCTCAACGTCTGCACTGCAGCGCGAACTGGTTTCCTTGAGTACGC
ACAAAGTGGGCGGAATTCGTGGTGTAGCGGTGAAATGCTTAGATATCACGAAGAACTCCG
ATTGCGAAGGCAGCTCACTGGAGCGCAACTGACGCTGAAGCTCGAAAGTGCGGGTATCGA
ACAGGATTAGATACCCTGGTAGTCCGCACGGTAAACGATGGATGCCCGCTGTTGGTCTGA
ATAGGTCAGCGGCCAAGCGAAAGCATTAAGCATCCCACCTGGGGAGTACGCCGGCAACGG
TGAAACTCAAAGGAATTGACGGGGGCCCGCACAAGCGGAGGAACATGTGGTTTAATTCGA
TGATACGCGAGGAACCTTACCCGGGCTTGAATTGCAGAGGAAGGATTTGGAGACAATGAC
GCCCTTCGGGGCCTCTGTGAAGGTGCTGCATGGTTGTCGTCAGCTCGTGCCGTGAGGTGT
CGGCTTAAGTGCCATAACGAGCGCAACCCCTCTCCTTAGTTGCCATCAGGTTAAGCTGGG
CACTCTGGGGACACTGCCACCGTAAGGTGTGAGGAAGGTGGGGATGACGTCAAATCAGCA
CGGCCCTTACGTCCGGGGCTACACACGTGTTACAATGGCAGGTACAGAGAGACGGTCCCT
TGCAAAATGGATCAAATCCTTAAAGCCTGTCTCAGTTCGGACTGGGGTCTGCAACCCGAC
CCCACGAAGCTGGATTCGCTAGTAATCGCGCATCAGCCATGGCGCGGTGAATACGTTCCC
GGGCCTTGTACACACCGCCCGTCAAGCCATGAAAGCCGGGGGCGCCTAAAGTCCGTGACC
GTAAGGAGCGGCCTAGGGCGAAACTGGTAATTGGGGCTAAGTCGTAACAAGGTAGCCGTA
CCGGAAGGTGCGGCTGGAACACCTCCTTT SEQ ID NO 14 *Christensenellaceae* R-7 Sp.
AAGAGTTTGATCCTGGCTCAGGACGAACGCTGGCGGCGTGCCTAACACATGCAAGTCGAG
CGGAGACAGTGAGTAGCTTGCTATGAGCTGTTTTAGCGGCGGACGGGTGAGTAACGCGTG
AGCAACCTTTCCCAGACAGGGGAATAACACACCGAAAGGTGTACTAATACCGCATAAGAC
CACGGGATCACATGGTTCTGGGGTAAAAGATTTATCGGTTTGGGGTGGGCTCGCGTCCGA
TTAGGTAGTTGGTGAGGTAACGGCCCACCAAGCCGACGATCGGTAGCCGACCTGAGAGGG
TGATCGGCCACATTGGGACTGAGACACGGCCCAAACTCCTACGGGAGGCAGCAGTGGGGA
ATATTGGGCAATGGGGGGAACCCTGACCCAGCAACGCCGCGTGGAGGAAGAAGGTTTTCG
GATCGTAAACTCCTGTCCTTGGAGACGAGTAGAAGACGGTATCCAAGGAGGAAGCCCCGG
CTAACTACGTGCCAGCAGCCGCGGTAATACGTAGGGGGCAAGCGTTGTCCGGAATAATTG
GGCGTAAAGGGCGCGTAGGCGGCTCGGTAAGTCTGGAGTGAAAGTCCTGCTTTTAAGGTG
GGAATTGCTTTGGATACTGTCGGGCTTGAGTGCAGGAGAGGTTAGTGGAATTCCCAGTGT
AGCGGTGAAATGCGTAGAGATTGGGAGGAACACCAGTGGCGAAGGCGACTAACTGGACTG
TAACTGACGCTGAGGCGCGAAAGTGTGGGGAGCAAACAGGATTAGATACCCTGGTAGTCC
ACACTGTAAACGATGAATGCTAGGTGTAGGGGGTATCGACCCCTTCTGTGCCGCAGTTAA
CACAATAAGCATTCCGCCTGGGGAGTACGGCCGCAAGGTTGAAACTCAAAGGAATTGACG
GGGGCCCGCACAAGCAGCGGAGCATGTGGTTTAATTCGACGCAACGCGAAGAACCTTACC
AGGTCTTGACATCCAGTAAAACTTGTAGAGATACAAGGTGAGCTTGCTCATACTGAGACA
GGTGGTGCATGGTTGTCGTCAGCTCGTGTCGTGAGATGTTGGGTTAAGTCCCGCAACGAG
CGCAACCCTTATCTTCAGTTACTAACGCGTAGAGGTGAGGACTCTGAAGAGACTGCCGGG
GACAACTCGGAGGAAGGTGGGGACGACGTCAAATCATCATGCCCCTTATGACCTGGGCTA
CACACGTGCTACAATGGCCACGACAGAGAGAAGCGAAATCGCAAGGTAGAGCGGAACTCA
AAAAAGTGGTCCCAGTTCGGATTGTGGGCTGCAACCCGCCCACATGAAGTCGGAGTTGCT
AGTAATCGCGGATCAGCATGCCGCGGTGAATACGTTCCCGGGCCTTGTACACACCGCCCG
TCACACCATGGGAGTTGGGAGTGCCCAAAGCCGGTGAGGCAACCGCAAGGAGCCAGCCGT
CTAAGGCAAGACCAATGACTGGGGTGAAGTCGTAACAAGGTAGCCGTATCGGAAGGTGCG
GCTGGATCACCTCCTTT SEQ ID NO 13 *Roseburia faecis*
ATGAGAGTTTGATCCTGGCTCAGGATGAACGCTGGCGGCGTGCTTAACACATGCAAGTCG
AACGAAGCACTCTATTTGATTTTCTTCGGAAATGAAGATTTTGTGACTGAGTGGCGGACG
GGTGAGTAACGCGTGGGTAACCTGCCTCATACAGGGGGATAACAGTTGGAAACGACTGCT
AATACCGCATAAGCGCACAGGATCGCATGATCCGGTGTGAAAAACTCCGGTGGTATGGGA
TGGACCCGCGTCTGATTAGCCAGTTGGCAGGGTAACGGCCTACCAAAGCGACGATCAGTA
GCCGACCTGAGAGGGTGACCGGCCACATTGGGACTGAGACACGGCCCAAACTCCTACGGG
AGGCAGCAGTGGGGAATATTGCACAATGGGGGAAACCCTGATGCAGCGACGCCGCGTGAG
CGAAGAAGTATTTCGGTATGTAAAGCTCTATCAGCAGGGAAGAAGAATGACGGTACCTGA
CTAAGAAGCACCGGCTAAATACGTGCCAGCAGCCGCGGTAATACGTATGGTGCAAGCGTT TABLE 11-continued

| Sequences |
|---|
| ATCCGGATTTACTGGGTGTAAAGGGAGCGCAGGCGGTGCGGCAAGTCTGATGTGAAAGCC<br>CGGGGCTCAACCCCGGTACTGCATTGGAAACTGTCGTACTAGAGTGTCGGAGGGGTAAGT<br>GGAATTCCTAGTGTAGCGGTGAAATGCGTAGATATTAGGAGGAACACCAGTGGCGAAGGC<br>GGCTTACTGGACGATAACTGACGCTGAGGCTCGAAAGCGTGGGGAGCAAACAGGATTAGA<br>TACCCTGGTAGTCCACGCCGTAAACGATGAATACTAGGTGTCGGGGAGCATTGCTCTTCG<br>GTGCCGCAGCAAACGCAATAAGTATTCCACCTGGGGAGTACGTTCGCAAGAATGAAACTC<br>AAAGGAATTGACGGGGACCCGCACAAGCGGTGGAGCATGTGGTTTAATTCGAAGCAACGC<br>GAAGAACCTTACCAAGTCTTGACATCCCGATGACAGAGTATGTAATGTACTTTCTCTTCG<br>GAGCATCGGTGACAGGTGGTGCATGGTTGTCGTCAGCTCGTGTCGTGAGATGTTGGGTTA<br>AGTCCCGCAACGAGCGCAACCCCTGTTCTTAGTAGCCAGCGGTCCGGCCGGGCACTCTAG<br>GGAGACTGCCAGGGATAACCTGGAGGAAGGCGGGGATGACGTCAAATCATCATGCCCCTT<br>ATGACTTGGGCTACACACGTGCTACAATGGCGTAAACAAAGGGAAGCGGAGCCGTGAGGC<br>CGAGCAAATCTCAAAAATAACGTCTCAGTTCGGACTGTAGTCTGCAACCCGACTACACGA<br>AGCTGGAATCGCTAGTAATCGCAGATCAGAATGCTGCGGTGAATACGTTCCCGGGTCTTG<br>TACACACCGCCCGTCACACCATGGGAGTTGGAAATGCCCGAAGTCAGTGACCCAACCGCA<br>AGGAGGGAGCTGCCGAAGGCAGGTTCGATAACTGGGGTGAAGTCGTAACAAGGTAGCCGT<br>ATCGGAAGGTGCGGCTGGATCACCTCCTTT |
| SEQ ID NO 2 *Christensenellaceae* R-7 Sp.<br>AAGAGTTTGATCCTGGCTCAGGACGAACGCTGGCGGCGTGCCTAACACATGCAAGTCGAG<br>CGGAGACAGTGAGTAGCTTGCTACTGATTGTTTTAGCGGCGGACGGGTGAGTAACGCGTG<br>AGCAACCTTTCCCAGACAGGGGAATAACACACCGAAAGGTGTACTAATACCGCATAAGAC<br>CACGGGATCACATGGTTCTGGGGTAAAAGAATTATCGGTTTGGGGGGGCTCGCGTCCGA<br>TTAGGTAGTTGGTGAGGTAACGGCCCACCAAGCCGACGATCGGTAGCCGACCTGAGAGGG<br>TGATCGGCCACATTGGGACTGAGACACGGCCCAAACTCCTACGGGAGGCAGCAGTGGGGA<br>ATATTGGGCAATGGAGGAAACTCTGACCCAGCAACGCCGCGTGGAGGAAGAAGGTTTTCG<br>GATCGTAAACTCCTGTCCTTGGAGACGAGTAGAAGACGGTATCCAAGGAGGAAGCCCCGG<br>CTAACTACGTGCCAGCAGCCGCGGTAATACGTAGGGGGCAAGCGTTGTCCGGAATAATTG<br>GGCGTAAAGGGCGCGTAGGCGGCTCGGTAAGTCTGGAGTGAAAGTCCTGCTTTTAAGGTG<br>GGAATTGCTTTGGATACTGTCGGGCTTGAGTGCAGGAGAGGTTAGTGGAATTCCCAGTGT<br>AGCGGTGAAATGCGTAGAGATTGGGAGGAACACCAGTGGCGAAGGCGACTAACTGGACTG<br>TAACTGACGCTGAGGCGCGAAAGTGTGGGGAGCAAACAGGATTAGATACCCTGGTAGTCC<br>ACACTGTAAACGATGAATGCTAGGTGTAGGGGGTATCGACCCCTTCTGTGCCGCAGTCAA<br>CACAATAAGCATTCCGCCTGGGGAGTACGGCCGCAAGGTTGAAACTCAAAGGAATTGACG<br>GGGGCCCGCACAAGCAGCGGAGCATGTGGTTTAATTCGACGCAACGCGAAGAACCTTACC<br>AGGTCTTGACATCCACTTAAACTTACAGAGATGTAAGGTGTGCTTGCACAAAGTGAGACA<br>GGTGGTGCATGGTTGTCGTCAGCTCGTGTCGTGAGATGTTGGGTTAAGTCCCGCAACGAG<br>CGCAACCCTTATCTTCAGTTACTAACGCGTAGAGGTGAGGACTCTGAAGAGACTGCCGGG<br>GACAACTCGGAGGAAGGTGGGGACGACGTCAAATCATCATGCCCCTTATGACCTGGGCTA<br>CACACGTGCTACAATGGCCACGACAGAGAGAAGCGAAATCGTAAGGTGGAGCGGAACTCA<br>AAAAAGTGGTCCCAGTTCGGATTGTGGGCTGCAACCCGCCCACATGAAGTCGGAGTTGCT<br>AGTAATCGCGGATCAGCATGCCGCGGTGAATACGTTCCCGGGCCTTGTACACACCGCCCG<br>TCACACCATGGGAGTTGGGAGTGCCCAAAGCCGGTGAGGCAACCGCAAGGAGCCAGCCGT<br>CTAAGGCAAGACCAATGACTGGGGTGAAGTCGTAACAAGGTAGCCGTATCGGAAGGTGCG<br>GCTGGATCACCTCCTTT |
| SEQ ID NO 8 *Bacteroides stercoris*<br>ATGAAGAGTTTGATCCTGGCTCAGGATGAACGCTAGCTATAGGCTTAACACATGCAAGTC<br>GAGGGGCAGCATCATCAAAGCTTGCTTTGATGGATGGCGACCGGCGCACGGGTGAGTAAC<br>ACGTATCCAACCTGCCGACAACTCTGGGATAGCCTTTCGAAAGAAAGATTAATACCGGAT<br>GGCATAGTTTTCCCGCATGGGTTGACTATTAAAGAATTTCGGTTGTCGATGGGGATGCGT<br>TCCATTAGGCAGTTGGCGGGGTAACGGCCCACCAAACCGACGATGGATAGGGGTTCTGAG<br>AGGAAGGTCCCCCACATTGGAACTGAGACACGGTCCAAACTCCTACGGGAGGCAGCAGTG<br>AGGAATATTGGTCAATGGACGAGAGTCTGAACCAGCCAAGTAGCGTGAAGGATGACTGCC<br>CTATGGGTTGTAAACTTCTTTTATACGGGAATAAAGTTAGCCACGTGTGGCTTTTTGTAT<br>GTACCGTATGAATAAGGATCGGCTAACTCCGTGCCAGCAGCCGCGGTAATACGGAGGATC<br>CGAGCGTTATCCGGATTTATTGGGTTTAAAGGGAGCGTAGGCGGGTTGTTAAGTCAGTTG<br>TGAAAGTTTGCGGCTCAACCGTAAAATTGCAGTTGATACTGGCGACCTTGAGTGCAACAG<br>AGGTAGGCGGAATTCGTGGTGTAGCGGTGAAATGCTTAGATATCACGAAGAACTCCGATT<br>GCGAAGGCAGCTTACTGGATTGTAACTGACGCTGATGCTCGAAAGTGTGGGTATCAAACA<br>GGATTAGATACCCTGGTAGTCCACACAGTAAACGATGAATACTCGCTGTTGGCGATATAC<br>TGTCAGCGGCCAAGCGAAAGCATTAAGTATTCCACCTGGGGAGTACGCCGGCAACGGTGA<br>AACTCAAAGGAATTGACGGGGGCCCGCACAAGCGGAGGAACATGTGGTTTAATTCGATGA<br>TACGCGAGGAACCTTACCCGGGCTTAAATTGCAACTGACGGAATCGGAAACGGTTCTTTC<br>TTCGGACAGTTGTGAAGGTGCTGCATGGTTGTCGTCAGCTCGTGCCGTGAGGTGTCGGCT<br>TAAGTGCCATAACGAGCGCAACCCTTATCGATAGTTACTAGCAGGTCATGCTGAGGACTC<br>TATCGAGACTGCCGTCGTAAGATGTGAGGAAGGTGGGGATGACGTCAAATCAGCACGGCC<br>CTTACGTCCGGGGCTACACACGTGTTACAATGGGGGGTACAGAAGGCAGCTACACGGCGA<br>CGTGGTGCTAATCCCGAAAGCCTCTCTCAGTTCGGATTGGAGTCTGCAACCCGACTCCAT<br>GAAGCTGGATTCGCTAGTAATCGCGCATCAGCCACGGCGCGGTGAATACGTTCCCGGGCC<br>TTGTACACACCGCCCGTCAAGCCATGAAAGCCGGGGGTACCTGAAGTACGTAACCGCGAG<br>GAGCGTCCTAGGGTAAAACTGGTGATTGGGGCTAAGTCGTAACAAGGTAGCCGTACCGGA<br>AGGTGCGGCTGGAACACCTCCTT |
| SEQ ID NO 6 *Eubacterium ventriosum*<br>AACGAGAGTTTGATCCTGGCTCAGGATGAACGCTGGCGGCGTGCTTAATACATGCAAGTC<br>GAACGAAGCACCTTGGACAGAATCCTTCGGGAGGAAGACCATTGTGACTGAGTGGCGGAC<br>GGGTGAGTAACGCGTGGGTAACCTGCCTTGTACAGGGGGATAACAGTTGGAAACGACTGC |

TABLE 11-continued

| Sequences |
|---|
| TAATACCGCATAAGCGCACAGTACCGCATGGTACGGTGTGAAAAACTCCGGTGGTACAAG<br>ATGGACCCGCGTCTGATTAGCTAGTTGGTGAGGTAACGGCCCACCAAGGCGACGATCAGT<br>AGCCGACTTGAGAGAGTGATCGGCCACATTGGGACTGAGACACGGCCCAAACTCCTACGG<br>GAGGCAGCAGTAGGGAATATTGCACAATGGGGGAAACCCTGATGCAGCGACGCCGCGTGA<br>AGGAAGAAGTATTTCGGTATGTAAACTTCTATCAGCAAGGAAGAAAATGACGGTACTTGA<br>CTAAGAAGCCCCGGCTAAATACGTGCCAGCAGCCGCGGTAATACGTATGGGGCAAGCGTT<br>ATCCGGATTTACTGGGTGTAAAGGGAGCGTAGGCGGCATGGCAAGTCAGAAGTGAAAGCC<br>TGGGGCTCAACCCCGGAATTGCTTTTGAAACTGTCAGGCTAGAGTGTCGGAGGGGTAAGC<br>GGAATTCCTAGTGTAGCGGTGAAATGCGTAGATATTAGGAGGAACACCGGTGGCGAAGGC<br>GGCTTACTGGACGATTACTGACGCTGAGGCTCGAAAGCGTGGGGAGCAAACAGGATTAGA<br>TACCCTGGTAGTCCACGCCGTAAACGATGAATACTAGGTGTCGGGGGACAATAGTTCCTC<br>GGTGCCGAAGCAAACGCATTAAGTATTCCACCTGGGGAGTACGTTCGCAAGAATGAAACT<br>CAAAGGAATTGACGGGGACCCGCACAAGCGGTGGAGCATGTGGTTTAATTCGAAGCAACG<br>CGAAGAACCTTACCTGCTCTTGACATCCCACTGACAGGTCAGTAATGTGACCCTTTCTTC<br>GGAACAGTGGAGACAGGTGGTGCATGGTTGTCGTCAGCTCGTGTCGTGAGATGTTGGGTT<br>AAGTCCCGCAACGAGCGCAACCCTTGTCTTTAGTAGCCAGCAGTACGGCTGGGCACTCTA<br>GAGAGACTGCCAGGGATAACCTGGAGGAAGGCGGGGATGACGTCAAATCATCATGCCCCT<br>TACGAGCAGGGCTACACACGTGCTACAATGGCGTAAACAAAGGGAAGCGACCCCGTGAGG<br>GTAAGCAAATCTCAAAAATAACGTCTCAGTTCGGATTGTAGTCTGCAACTCGACTACATG<br>AAGCTGGAATCGCTAGTAATCGCGAATCAGAATGTCGCGGTGAATACGTTCCCGGGTCTT<br>GTACACACCGCCCGTCACACCATGGGAGTTGGATATGCCCGAAGTCAGTGACCCAACCGT<br>AAGGAGGGAGCTGCCGAAGGTGGAGCCGATAACTGGGGTGAAGTCGTAACAAGGTAGCCG<br>TATCGGAAGGTGCGGCTGGATCACCTCCTTT |
| SEQ ID NO 1 *Bifidobacterium adolescentis*<br>TGTGGAGGGTTCGATTCTGGCTCAGGATGAACGCTGGCGGCGTGCTTAACACATGCAAGT<br>CGAACGGGATCCCAGGAGCTTGCTCCTGGGTGAGAGTGGCGAACGGGTGAGTAATGCGTG<br>ACCGACCTGCCCCATACACCGGAATAGCTCCTGGAAACGGGTGGTAATGCCGGATGCTCC<br>AGTTGACCGCATGGTCCTCTGGGAAAGCTTTTGCGGTATGGGATGGGGTCGCGTCCTATC<br>AGCTTGATGGCGGGGTAACGGCCCACCATGGCTTCGACGGGTAGCCGGCCTGAGAGGGCG<br>ACCGGCCACATTGGGACTGAGATACGGCCCAGACTCCTACGGGAGGCAGCAGTGGGGAAT<br>ATTGCACAATGGGCGCAAGCCTGATGCAGCGACGCCGCGTGCGGGATGACGGCCTTCGGG<br>TTGTAAACCGCTTTTGACTGGGAGCAAGCCCTTCGGGGTGAGTGTACCTTTCGAATAAGC<br>ACCGGCTAACTACGTGCCAGCAGCCGCGGTAATACGTAGGGTGCAAGCGTTATCCGGAAT<br>TATTGGGCGTAAAGGGCTCGTAGGCGGTTCGTCGCGTCCGGTGTGAAAGTCCATCGCTTA<br>ACGGTGGATCCGCGCCGGGTACGGGCGGGCTTGAGTGCGGTAGGGGAGACTGGAATTCCC<br>GGTGTAACGGTGGAATGTGTAGATATCGGGAAGAACACCAATGGCGAAGGCAGGTCTCTG<br>GGCCGTCACTGACGCTGAGGAGCGAAAGCGTGGGGAGCGAACAGGATTAGATACCCTGGT<br>AGTCCACGCCGTAAACGGTGGATGCTGGATGTGGGGACCATTCCACGGTCTCCGTGTCGG<br>AGCCAACGCGTTAAGCATCCCGCCTGGGGAGTACGGCCGCAAGGCTAAAACTCAAAGAAA<br>TTGACGGGGGCCCGCACAAGCGGCGGAGCATGCGGATTAATTCGATGCAACGCGAAGAAC<br>CTTACCTGGGCTTGACATGTTCCCGACAGCCCCAGAGATGGGGCCTCCCTTCGGGGGGGG<br>TTCACAGGTGGTGCATGGTCGTCGTCAGCTCGTGTCGTGAGATGTTGGGTTAAGTCCCGC<br>AACGAGCGCAACCCTCGCCCTGTGTTGCCAGCACGTCGTGGTGGGAACTCACGGGGGACC<br>GCCGGGGTCAACTCGGAGGAAGGTGGGGATGACGTCAGATCATCATGCCCCTTACGTCCA<br>GGGCTTCACGCATGCTACAATGGCCGGTACAACGGGATGCGACACCGCGAGGTGGAGCGG<br>ATCCCTTAAAACCGGTCTCAGTTCGGATTGGAGTCTGCAACCCGACTCCATGAAGGCGGA<br>GTCGCTAGTAATCGCGGATCAGCAACGCCGCGGTGAATGCGTTCCCGGGCCTTGTACACA<br>CCGCCCGTCAAGTCATGAAAGTGGGTAGCACCCGAAGCCGGTGGCCCAACCTTTTGGGGG<br>GAGCCGTCTAAGGTGAGACTCGTGATTGGGACTAAGTCGTAACAAGGTAGCCGTACCGGA<br>AGGTGCGGCTGGATCACCTCCTTT |
| SEQ ID NO 4 *Prevotella copri*<br>ATGGAGAGTTTGATCCTGGCTCAGGATGAACGCTAGCTACAGGCTTAACACATGCAAGTC<br>GAGGGGAAACGACATCGAAAGCTTGCTTTTGATGGGCGTCGACCGGCGCACGGGTGAGTA<br>ACGCGTATCCAACCTGCCCACCACTTGGGGATAACCTTGCGAAAGTAAGACTAATACCCA<br>ATGATATCTCTAGAAGACATCTGAAAGAGATTAAAGATTTATCGGTGATGGATGGGGATG<br>CGTCTGATTAGCTTGTTGGCGGGGTAACGGCCCACCAAGGCGACGATCAGTAGGGGTTCT<br>GAGAGGAAGGTCCCCCACATTGGAACTGAGACACGGTCCAAACTCCTACGGGAGGCAGCA<br>GTGAGGAATATTGGTCAATGGACGAGAGTCTGAACCAGCCAAGTAGCGTGCAGGATGACG<br>GCCCTATGGGTTGTAAACTGCTTTTATAAGGGAATAAAGTGAGTCTCGTGAGACTTTTTG<br>CATGTACCTTATGAATAAGGACCGGCTAATTCCGTGCCAGCAGCCGCGGTAATACGGAAG<br>GTCCGGGCGTTATCCGGATTTATTGGGTTTAAAGGGAGCGTAGGCCGGAGATTAAGCGTG<br>TTGTGAAATGTAGACGCTCAACGTCTGCACTGCAGCGCGAACTGGTTTCCTTGAGTACGC<br>ACAAAGTGGGCGGAATTCGTGGTGTAGCGGTGAAATGCTTAGATATCACGAAGAACTCCG<br>ATTGCGAAGGCAGCTCACTGGAGCGCAACTGACGCTGAAGCTCGAAAGTGCGGGTATCGA<br>ACAGGATTAGATACCCTGGTAGTCCGCACGGTAAACGATGGATGCCCGCTGTTGGTCTGA<br>ATAGGTCAGCGGCCAAGCGAAAGCATTAAGCATCCCACCTGGGGAGTACGCCGGCAACGG<br>TGAAACTCAAAGGAATTGACGGGGGCCCGCACAAGCGGAGGAACATGTGGTTTAATTCGA<br>TGATACGCGAGGAACCTTACCCGGGCTTGAATTGCAGAGGAAGGATTTGGAGACAATGAC<br>GCCCTTCGGGGCCTCTGTGAAGGTGCTGCATGGTTGTCGTCAGCTCGTGCCGTGAGGTGT<br>CGGCTTAAGTGCCATAACGAGCGCAACCCCTCTCCTTAGTTGCCATCAGGTCACGCTGGG<br>CACTCTGGGGACACTGCCACCGTAAGGTGTGAGGAAGGTGGGGATGACGTCAAATCAGCA<br>CGGCCCTTACGTCCGGGGCTACACACGTGTTACAATGGCAGGTACAGAGAGATGGTCCCT<br>TGCAAAATGGATCAAATCCTTAAAGCCTGTCTCAGTTCGGACTGGGGTCTGCAACCCGAC<br>CCCACGAAGCTGGATTCGCTAGTAATCGCGCATCAGCCATGGCGCGGTGAATACGTTCCC |

TABLE 11-continued

| Sequences |
| --- |
| GGGCCTTGTACACACCGCCCGTCAAGCCATGAAAGCCGGGGGCGCCTAAAGTCCGTGACC<br>GTAAGGAGCGGCCTAGGGCGAAACTGGTAATTGGGGCTAAGTCGTAACAAGGTAGCCGTA<br>CCGGAAGGTGCGGCTGGAACACCTCCTTT |
| SEQ ID NO 9 *Roseburia faecis*<br>ATGAGAGTTTGATCCTGGCTCAGGATGAACGCTGGCGGCGTGCTTAACACATGCAAGTCG<br>AACGAAGCACTCTATTTGATTTTCTTCGGAAATGAAGATTTTGTGACTGAGTGGCGGACG<br>GGTGAGTAACGCGTGGGTAACCTGCCTCATACAGGGGGATAACAGTTGGAAACGACTGCT<br>AATACCGCATAAGCGCACAGGATCGCATGATCCGGTGTGAAAAACTCCGGTGGTATGGGA<br>TGGACCCGCGTCTGATTAGCCAGTTGGCAGGGTAACGGCCTACCAAAGCGACGATCAGTA<br>GCCGACCTGAGAGGGTGACCGGCCACATTGGGACTGAGACACGGCCCAAACTCCTACGGG<br>AGGCAGCAGTGGGGAATATTGCACAATGGGGGAAACCCTGATGCAGCGACGCCGCGTGAG<br>CGAAGAAGTATTTCGGTATGTAAAGCTCTATCAGCAGGGAAGAAGAATGACGGTACCTGA<br>CTAAGAAGCACCGGCTAAATACGTGCCAGCAGCCGCGGTAATACGTATGGTGCAAGCGTT<br>ATCCGGATTTACTGGGTGTAAAGGGAGCGCAGGCGGTGCGGCAAGTCTGATGTGAAAGCC<br>CGGGGCTCAACCCCGGTACTGCATTGGAAACTGTCGTACTAGAGTGTCGGAGGGGTAAGT<br>GGAATTCCTAGTGTAGCGGTGAAATGCGTAGATATTAGGAGGAACACCAGTGGCGAAGGC<br>GGCTTACTGGACGATAACTGACGCTGAGGCTCGAAAGCGTGGGGAGCAAACAGGATTAGA<br>TACCCTGGTAGTCCACGCCGTAAACGATGAATACTAGGTGTCGGGGAGCATTGCTCTTCG<br>GTGCCGCAGCAAACGCAATAAGTATTCCACCTGGGGAGTACGTTCGCAAGAATGAAACTC<br>AAAGGAATTGACGGGGACCCGCACAAGCGGTGGAGCATGTGGTTTAATTCGAAGCAACGC<br>GAAGAACCTTACCAAGTCTTGACATCCCGATGACAAGCTATGTAATGTAGCCTCTCTTCG<br>GAGCATCGGTGACAGGTGGTGCATGGTTGTCGTCAGCTCGTGTCGTGAGATGTTGGGTTA<br>AGTCCCGCAACGAGCGCAACCCCTGTTCTTAGTAGCCAGCGGTTCGGCCGGGCACTCTAG<br>GGAGACTGCCAGGGATAACCTGGAGGAAGGCGGGGATGACGTCAAATCATCATGCCCCTT<br>ATGACTTGGGCTACACACGTGCTACAATGGCGTAAACAAAGGGAAGCGGAGCCGTGAGGC<br>CGAGCAAATCTCAAAAATAACGTCTCAGTTCGGACTGTAGTCTGCAACCCGACTACACGA<br>AGCTGGAATCGCTAGTAATCGCAGATCAGAATGCTGCGGTGAATACGTTCCCGGGTCTTG<br>TACACACCGCCCGTCACACCATGGGAGTTGGAAATGCCCGAAGTCAGTGACCCAACCGCA<br>AGGAGGGAGCTGCCGAAGGCAGGTTCGATAACTGGGGTGAAGTCGTAACAAGGTAGCCGT<br>ATCGGAAGGTGCGGCTGGATCACCTCCTTT |
| SEQ ID No. 23 *Bacteroides Stercoris*<br>ATGAAGAGTTTGATCCTGGCTCAGGATGAACGCTAGCTACAGGCTTAACACATGCAAGTCGAGGGGCA<br>GCATCATCAAAGCTTGCTTTGATGGATGGCGACCGGCGCACGGGTGAGTAACACGTATCCAACCTGCC<br>GACAACACTGGGATAGCCTTTCGAAAGAAAGATTAATACYGGATGGCATAGTTTTCCCGCATGGGATA<br>ATTATTAAAGAATTTCGGTTGTCGATGGGGATGCGTTCCATTAGGCAGTTGGCGGGGTAACGGCCCAC<br>CAAACCWACGATGGATAGGGGTTCTGAGAGGAAGGTCCCCCACATTGGAACTGAGACACGGTCCAAAC<br>TCCTACGGGAGGCAGCAGTGAGGAATATTGGTCAATGGACGAGAGTCTGAACCAGCCAAGTAGCGTGA<br>AGGATGACTGCCCTATGGGTTGTAAACTTCTTTTATACGGGAATAAAGTTAGCCACGTGTGGYTTTTT<br>GTATGTACCGTATGAATAAGGATCGGCTAACTCCGTGCCAGCAGCCGCGGTAATACGGAGGATCCGAG<br>CGTTATCCGGATTTATTGGGTTTAAAGGGAGCGTAGGCGGGTTGTTAAGTCAGTTGTGAAAGTTTGCG<br>GCTCAACCGTAAAATTGCAGTTGATACTGGCGACCTTGAGTGCAACAGAGGTAGGCGGAATTCGTGGT<br>GTAGCGGTGAAATGCTTAGATATCACGAAGAACTCCGATTGCGAAGGCAGCTTACTGGATTGTAACTG<br>ACGCTGATGCTCGAAAGTGTGGGTATCAAACAGGATTAGATACCCTGGTAGTCCACACAGTAAACGAT<br>GAATACTCGCTGTTGGCGATATACRGTCAGCGGCCAAGCGAAAGCATTAAGTATTCCACCTGGGGAGT<br>ACGCCGGCAACGGTGAAACTCAAAGGAATTGACGGGGGCCCGCACAAGCGGAGGAACATGTGGTTTAA<br>TTCGATGATACGCGAGGAACCTTACCCGGGCTTAAATTGCAACTGACTGAACCGGAAACGGTTCTTTC<br>TTCGGACAGTTGTGAAGGTGCTGCATGGTTGTCGTCAGCTCGTGCCGTGAGGTGTCGGCTTAAGTGCC<br>ATAACGAGCGCAACCCTTATCGATAGTTACTAGCAGGTCATGCTGAGGACTCTATTGAGACTGCCGTC<br>GTAAGATGTGAGGAAGGTGGGGATGACGTCAAATCAGCACGGCCCTTACGTCCGGGGCTACACACGTG<br>TTACAATGGGGGGTACAGAAGGCAGCTACACGGCGACGTGGTGCTAATCCCTAAAGCCTCTCTCAGTT<br>CGGATTGGAGTCTGCAACCCGACTCCATGAAGCTGGATTCGCTAGTAATCGCGCATCAGCCACGGCGC<br>GGTGAATACGITCCCGGGCCTTGTACACACCGCCCGTCAAGCCATGAAAGCCGGGGGTACCTGAAGTA<br>CGTAACCGCGAGGAGCGTCCTAGGGTAAAACTGGTGATTGGGGCTAAGTCGTAACAAGGTAGCCGTAC<br>CGGAAGGTGCGGCTGGAACACCTCCTT |
| SEQ ID NO. 22 *Barnesiella Intestinihominis*<br>CGAAGAGTTTGATCCTGGCTCAGGATGAACGCTAGCGACAGGCCTAACACATGCAAGTCGAGGGGCAGCGGGGAG<br>GTAGCAATACCTTTGCCGGCGACCGGCGCACGGGTGAGTAACACGTATGCAATCCACCTGTAACAGGGGGATAAC<br>CCGGAGAAATCCGGACTAATACCCCATAATATGGGCTCTCCGCATGGAGGGTTCATTAAAGAGAGCAATTTTGGT<br>TACAGACGAGCATGCGCTCCATTAGCCAGTTGGCGGGGTAACGGCCCACCAAAGCGACGATGGATAGGGGTTCTG<br>AGAGGAAGGTCCCCCACATTGGAACTGAGACACGGTCCAAACTCCTACGGGAGGCAGCAGTGAGGAATATTGGTC<br>AATGGTCGGCAGACTGAACCAGCCAAGTCGCGTGAGGGAAGACGGCCCTACGGGTTGTAAACCTCTTTTGTCGGA<br>GAGTAAAGTACGCTACGTGTAGTGTATTGCAAGTATCCGAAGAAAAAGCATCGGCTAACTCCGTGCCAGCAGCCG<br>CGGTAATACGGAGGATGCGAGCGTTATCCGGATTTATTGGGTTTAAAGGGTGCGTAGGCGGCACGCCAAGTCAGC<br>GGTGAAATTTTCGGGCTCAACCCGGACTGTGCCGTTGAAACTGGCGAGCTAGAGTGCACAAGAGGCAGGCGGAAT<br>GCGTGGTGTAGCGGTGAAATGCATAGATATCACGCAGAACCCCGATTGCGAAGGCAGCCTGCTAGGGTGCGACAG<br>ACGCTGAGGCACGAAAGCGTGGGTATCGAACAGGATTAGATACCCTGGTAGTCCACGCAGTAAACGATGAATACT<br>AACTGTTTGCGATACAATGTAAGCGGTACAGCGAAAGCGTTAAGTATTCCACCTGGGGAGTACGCCGGCAACGGT<br>GAAACTCAAAGGAATTGACGGGGGCCCGCACAAGCGGAGGAACATGTGGTTTAATTCGATGATACGCGAGGAACC<br>TTACCCGGGCTCAAACGCAGGGGGAATATATATGAAAGTATATAGCTAGCAATAGTCACCTGCGAGGTGCTGCAT<br>GGTTGTCGTCAGCTCGTGCCGTGAGGTGTCGGCTTAAGTGCCATAACGAGCGCAACCCCTATCGACAGTTACTAA<br>CGGGTCAAGCCGAGGACTCTGTCGAGACTGCCGGCGCAAGCCGCGAGGAAGGTGGGGATGACGTCAAATCAGCAC<br>GGCCCTTACGTCCGGGGCGACACACGTGTTACAATGGCAGGTACAGAAGGCAGCCAGTCAGCAATGACGCGCGAA<br>TCCCGAAAACCTGTCTCAGTTCGGATTGGAGTCTGCAACCCGACTCCATGAAGCTGGATTCGCTAGTAATCGCGC |

TABLE 11-continued

| Sequences |
| --- |
| ATCAGCCATGGCGCGGTGAATACGTTCCCGGGCCTTGTACACACCGCCCGTCAAGCCATGGAAGCCGGGAGTACC TGAAGCATGCAACCGCAAGGAGCGTACGAAGGTAATACCGGTAACTGGGGCTAAGTCGTAACAAGGTAGCCGTAC CGGAAGGTGCGGCTGGAACACCTCCTTT |
| SEQ ID No. 16 *Bifidobacterium adolescentis* TGTGGAGGGTTCGATTCTGGCTCAGGATGAACGCTGGCGGCGTGCTTAACACATGCAAGTCGAACGGGATCGGCT GGAGCTTGCTCCGGCCGTGAGAGTGGCGAACGGGTGAGTAATGCGTGACCGACCTGCCCCATACACCGGAATAGC TCCTGGAAACGGGTGGTAATGCCGGATGCTCCAGTTGGATGCATGTCCTTCTGGGAAAGATTCATCGGTATGGGA TGGGGTCGCGTCCTATCAGCTTGATGGCGGGGTAACGGCCCACCATGGCTTCGACGGGTAGCCGGCCTGAGAGGG CGACCGGCCACATTGGGACTGAGATACGGCCCAGACTCCTACGGGAGGCAGCAGTGGGGAATATTGCACAATGGG CGCAAGCCTGATGCAGCGACGCCGCGTGCGGGATGACGGCCTTCGGGTTGTAAACCGCTTTTGACTGGGAGCAAG CCCTTCGGGGTGAGTGTACCTTTCGAATAAGCACCGGCTAACTACGTGCCAGCAGCCGCGGTAATACGTAGGGTG CAAGCGTTATCCGGAATTATTGGGCGTAAAGGGCTCGTAGGCGGTTCGTCGCGTCCGGTGTGAAAGTCCATCGCT TAACGGTGGATCCGCGCCGGGTACGGGCGGGCTTGAGTGCGGTAGGGGAGACTGGAATTCCCGGTGTAACGGTGG AATGTGTAGATATCGGGAAGAACACCAATGGCGAAGGCAGGTCTCTGGGCCGTCACTGACGCTGAGGAGCGAAAG CGTGGGGAGCGAACAGGATTAGATACCCTGGTAGTCCACGCCGTAAACGGTGGATGCTGGATGTGGGGACCATTC CACGGTCTCCGTGTCGGAGCCAACGCGTTAAGCATCCCGCCTGGGGAGTACGGCCGCAAGGCTAAAACTCAAAGA AATTGACGGGGGCCCGCACAAGCGGCGGAGCATGCGGATTAATTCGATGCAACGCGAAGAACCTTACCTGGGCTT GACATGTTCCCGACAGCCSYAGAGATRSGGYCTCCCTTCGGGGGGGGTTCACAGGTGGTGCATGGTCGTCGTCAG CTCGTGTCGTGAGATGTTGGGTTAAGTCCCGCAACGAGCGCAACCCTCGCCCTGTGTTGCCAGCACGTCGTGGTG GGAACTCACGGGGGACCGCCGGGGTCAACTCGGAGGAAGGTGGGGATGACGTCAGATCATCATGCCCCTTACGTC CAGGGCTTCACGCATGCTACAATGGCCGGTACAACGGGATGCGACACCGCGAGGTGGAGCGGATCCCTTAAAACC GGTCTCAGTTCGGATTGGAGTCTGCAACCCGACTCCATGAAGGCGGAGTCGCTAGTAATCGCGGATCAGCAACGC CGCGGTGAATGCGTTCCCGGGCCTTGTACACACCGCCCGTCAAGTCATGAAAGTGGGTAGCACCCGAAGCCGGTG GCCCAACCTTTTGGGGGGAGCCGTCTAAGGTGAGACTCGTGATTGGGACTAAGTCGTAACAAGGTAGCCGTACCG GAAGGTGCGGCTGGATCACCTCCTTT |
| SEQ ID No. 20 *Bifidobacterium pseudocatenulatum* TGTGGAGGGTTCGATTCTGGCTCAGGATGAACGCTGGCGGCGTGCTTAACACATGCAAGTCGAACGGGATCCATC AGGCTTTGCTTGGTGGTGAGAGTGGCGAACGGGTGAGTAATGCGTGACCGACCTGCCCCATACACCGGAATAGCT CCTGGAAACGGGTGGTAATGCCGGATGCTCCGACTCCTCGCATGGGGTGTCGGGAAAGATTTCATCGGTATGGGA TGGGGTCGCGTCCTATCAGGTAGTCGGCGGGGTAACGGCCCACCGAGCCTACGACGGGTAGCCGGCCTGAGAGGG CGACCGGCCACATTGGGACTGAGATACGGCCCAGACTCCTACGGGAGGCAGCAGTGGGGAATATTGCACAATGGG CGCAAGCCTGATGCAGCGACGCCGCGTGCGGGATGACGGCCTTCGGGTTGTAAACCGCTTTTGATCGGGAGCAAG CCTTCGGGTGAGTGTACCTTTCGAATAAGCACCGGCTAACTACGTGCCAGCAGCCGCGGTAATACGTAGGGTGCA AGCGTTATCCGGAATTATTGGGCGTAAAGGGCTCGTAGGCGGTTCGTCGCGTCCGGTGTGAAAGTCCATCGCTTA ACGGTGGATCTGCGCCGGGTACGGGGGGCTGGAGTGCGGTAGGGGAGACTGGAATTCCCGGTGTAACGGTGGAA TGTGTAGATATCGGGAAGAACACCAATGGCGAAGGCAGGTCTCTGGGCCGTTACTGACGCTGAGGAGCGAAAGCG TGGGGAGCGAACAGGATTAGATACCCTGGTAGTCCACGCCGTAAACGGTGGATGCTGGATGTGGGGCCCGTTCCA CGGGTTCCGTGTCGGAGCTAACGCGTTAAGCATCCCGCCTGGGGAGTACGGCCGCAAGGCTAAAACTCAAAGAAA TTGACGGGGGCCCGCACAAGCGGCGGAGCATGCGGATTAATTCGATGCAACGCGAAGAACCTTACCTGGGCTTGA CATGTTCCCGACAGCCGTAGAGATATGGCCTCCCTTCGGGGGGGGTTCACAGGTGGTGCATGGTCGTCGTCAGCT CGTGTCGTGAGATGTTGGGTTAAGTCCCGCAACGAGCGCAACCCTCGCCCTGTGTTGCCAGCACGTCATGGTGGG AACTCACGGGGGACCGCCGGGGTCAACTCGGAGGAAGGTGGGGATGACGTCAGATCATCATGCCCCTTACGTCCA GGGCTTCACGCATGCTACAATGGCCGGTACAACGGGATGCGACACGGCGACGTGGAGCGGATCCCTGAAAACCGG TCTCAGTTCGGATTGGAGTCTGCAACCCGACTCCATGAAGGCGGAGTCGCTAGTAATCGCGGATCAGCAACGCCG CGGTGAATGCGTTCCCGGGCCTTGTACACACCGCCCGTCAAGTCATGAAAGTGGGTAGCACCCGAAGCCGGTGGC CTAACCCTTTGTGGATGGAGCCGTCTAAGGTGAGACTCGTGATTGGGACTAAGTCGTAACAAGGTAGCCGTACCG GAAGGTGCGGCTGGATCACCTCCTTT |
| SEQ ID No. 21 *Eubacterium ventriosum* AACGAGAGTTTGATCCTGGCTCAGGATGAACGCTGGCGGCGTGCTTAATACATGCAAGTCGAACGAAGCACCTTG GACAGAATCCTTCGGGAGGAAGACCATTGTGACTGAGTGGCGGACGGGTGAGTAACGCGTGGGTAACCTGCCTTG TACAGGGGGATAACAGTTGGAAACGACTGCTAATACCGCATAAGCGCACAGTACCGCATGGTACGGTGTGAAAAA CTCCGGTGGTACAAGATGGACCCGCGTCTGATTAGCTGGTTGGTGAGGTAACGGCCCACCAAGGCGACGATCAGT AGCCGACTTGAGAGAGTGATCGGCCACATTGGGACTGAGACACGGCCCAAACTCCTACGGGAGGCAGCAGTAGGG AATATTGCACAATGGGGGAAACCCTGATGCAGCGACGCCGCGTGAAGGAAGAAGTATTTCGGTATGTAAACTTCT ATCAGCAAGGAAGAAAATGACGGTACTTGACTAAGAAGCCCCGGCTAAATACGTGCCAGCAGCCGCGGTAATACG TATGGGGCAAGCGTTATCCGGATTTACTGGGTGTAAAGGGAGCGTAGGCGGCATGGCAAGTCAGAAGTGAAAGCC TGGGGCTCAACCCCGGAATTGCTTTTGAAACTGTCAGGCTAGAGTGTCGGAGGGGTAAGCGGAATTCCTAGTGTA GCGGTGAAATGCGTAGATATTAGGAGGAACACCGGTGGCGAAGGCGGCTTACTGGACGATTACTGACGCTGAGGC TCGAAAGCGTGGGGAGCAAACAGGATTAGATACCCTGGTAGTCCACGCCGTAAACGATGAATACTAGGTGTCGGG GGACAATAGTTCCTCGGTGCCGAAGCAAACGCATTAAGTATTCCACCTGGGGAGTACGTTCGCAAGAATGAAACT CAAAGGAATTGACGGGGACCCGCACAAGCGGTGGAGCATGTGGTTTAATTCGAAGCAACGCGAAGAACCTTACCT GCTCTTGACATCCCACTGACAGGTCAGTAATGTGACCCTTTCTTCGGAACAGTGGAGACAGGTGGTGCATGGTTG TCGTCAGCTCGTGTCGTGAGATGTTGGGTTAAGTCCCGCAACGAGCGCAACCCTTGTCTTTAGTAGCCAGCAGTA CGGCTGGGCACTCTAGAGAGACTGCCAGGGATAACCTGGAGGAAGGCGGGGATGACGTCAAATCATCATGCCCCT TACGAGCAGGGCTACACACGTGCTACAATGGCGTAAACAAAGGGAAGCGACCCCGTGAGGGCAAGCAAATCTCAA AAATAACGTCTCAGTTCGGATTGTAGTCTGCAACTCGACTACATGAAGCTGGAATCGCTAGTAATCGCGAATCAG AATGTCGCGGTGAATACGTTCCCGGGTCTTGTACACACCGCCCGTCACACCATGGGAGTTGGATATGCCCGAAGT CAGTGACCCAACCGTAAGGAGGGAGCTGCCGAAGGTGGAGCCGATAACTGGGGTGAAGTCGTAACAAGGTAGCCG TATCGGAAGGTGCGGCTGGATCACCTCCTTT |
| SEQ Id No. 17 *Christensenellaceae* R-7 group species AAGAGTTTGATCCTGGCTCAGGACGAACGCTGGCGGCGTGCCTAACACATGCAAGTCGAGCGGAGACAGTGAGTA GCTTGCTAYGAGCTGTTTTAGCGGCGGACGGGTGAGTAACGCGTGAGCAACCTTTCCCAGACAGGGGAATAACAC ACCGAAAGGTGTACTAATACCGCATAAGACCACGGKWTCACATGGKWCTGRGGTAAAAGATTTATCGGTTTGGGG TGGCTCGCGTCCGATTAGGTAGTTGGTGAGGTAACGGCCCACCAAGCCGACGATCGGTAGCCGACCTGAGAGGG |

TABLE 11-continued

| Sequences |
| --- |
| TGATCGGCCACATTGGGACTGAGACACGGCCCAAACTCCTACGGGAGGCAGCAGTGGGGAATATTGGGCAATGGR<br>GGRAACYCTGACCCAGCAACGCCGCGTGGAGGAAGAAGGTTTTCGGATCGTAAACTCCTGTCCTTGGAGACGAGT<br>AGAAGACGGTATCCAAGGAGGAAGCCCCGGCTAACTACGTGCCAGCAGCCGCGGTAATACGTAGGGGGCAAGCGT<br>TGTCCGGAATAATTGGGCGTAAAGGGCGCGTAGGCGGCTCGGTAAGTCTGGAGTGAAAGTCCTGCTTTTAAGGTG<br>GGAATTGCTTTGGATACTGTCGGGCTTGAGTGCAGGAGAGGTTAGTGGAATTCCCAGTGTAGCGGTGAAATGCGT<br>AGAGATTGGGAGGAACACCAGTGGCGAAGGCGACTAACTGGACTGTAACTGACGCTGAGGCGCGAAAGTGTGGGG<br>AGCAAACAGGATTAGATACCCTGGTAGTCCACACTGTAAACGATGAATGCTAGGTGTAGGGGGTATCGACCCCTT<br>CTGTGCCGCAGTCAACACAATAAGCATTCCGCCTGGGGAGTACGGCCGCAAGGTTGAAACTCAAAGGAATTGACG<br>GGGGCCCGCACAAGCAGCGGAGCATGTGGTTTAATTCGACGCAACGCGAAGAACCTTACCAGGTCTTGACATCCA<br>CTTAAACTTACAGAGATGTAAGGTGTGCTTGCACAAAGTGAGACAGGTGGTGCATGGTTGTCGTCAGCTCGTGTC<br>GTGAGATGTTGGGTTAAGTCCCGCAACGAGCGCAACCCTTATCTTCAGTTACTAACG |
| SEQ ID NO. 19 *Prevotella copri*<br>ATGGAGAGTTTGATCCTGGCTCAGGATGAACGCTAGCTACAGGCTTAACACATGCAAGTCGAGGGGAAACGAYAT<br>YGRAAGCTTGCTTYYGATRGGCGTCGACCGGCGCACGGGTGAGTAACGCGTATCCAACCTGCCCAYCACTTGGGG<br>ATAACCTTGCGAAAGTAAGACTAATACCCAATGAYRTCTCTAGAAGACATCTGAAAGAGATTAAAGATTYATCGG<br>TGATGGATGGGGATGCGTCTGATTAGCTTGTTGGCGGGGTAACGGCCCACCAAGGCRACGATCAGTAGGGGTTCT<br>GAGAGGAAGGTCCCCCACATTGGAACTGAGACACGGTCCAAACTCCTACGGGAGGCAGCAGTGAGGAATATTGGT<br>CAATGGACGAGAGTCTGAACCAGCCAAGTAGCGTGCAGGAWGACGGCCCTATGGGTTGTAAACTGCTTTTATAAG<br>GGAATAAAGTGAGWSTCGTGASWCTTTTTGCATGTACCTTATGAATAAGGACCGGCTAATTCCGTGCCAGCAGCC<br>GCGGTAATACGGAAGGTCCGGGCGTTATCCGGATTTATTGGGTTTAAAGGGAGCGTAGGCCGGAGATTAAGCGTG<br>TTGTGAAATGTAGAYGCTCAACRTCTGMACTGCAGCGCGAACTGGTTTCCTTGAGTACGCACAAAGTGGGCGGAA<br>TTCGTGGTGTAGCGGTGAAATGCTTAGATATCACGAAGAACTCCGATTGCGAAGGCAGCTCACTGGAGCGCAACT<br>GACGCTGAAGCTCGAAAGTGCGGGTATCGAACAGGATTAGATACCCTGGTAGTCCGCACGGTAAACGATGGATGC<br>CCGCTGTTGGTCTGAATAGGTCAGCGGCCAAGCGAAAGCATTAAGCATCCCACCTGGGGAGTACGCCGGCAACGG<br>TGAAACTCAAAGGAATTGACGGGGGCCCGCACAAGCGGAGGAACATGTGGTTTAATTCGATGATACGCGAGGAAC<br>CTTACCCGGGCTTGAATTGCAGAGGAAGGATTTGGAGACAATGACGCCCTTCGGGGCCTCTGTGAAGGTGCTGCA<br>TGGTTGTCGTCAGCTCGTGCCGTGAGGTGTCGGCTTAAGTGCCATAACGAGCGCAACCCCTCTCCTTAGTTGCCA<br>TCAGGTYAWGCTGGGCACTCTGGGGACACTGCCACCGTAAGGTGTGAGGAAGGTGGGGATGACGTCAAATCAGCA<br>CGGCCCTTACGTCCGGGGCTACACACGTGTTACAATGGCAGGTACAGAGAGACGGTCCCTTGCAAAATGGATCAA<br>ATCCTTAAAGCCTGTCTCAGTTCGGACTGGGGTCTGCAACCCGACCCCACGAAGCTGGATTCGCTAGTAATCGCG<br>CATCAGCCATGGCGCGGTGAATACGTTCCCGGGCCTTGTACACACCGCCCGTCAAGCCATGAAAGCCGGGGGCGC<br>CTAAAGTCCGTGACCGTAAGGAGCGGCCTAGGGCGAAACTGGTAATTGGGGCTAAGTCGTAACAAGGTAGCCGTA<br>CCGGAAGGTGCGGCTGGAACACCTCCTTT |
| SEQ ID No. 24 *Roseburia faecis*<br>ATGAGAGTTTGATCCTGGCTCAGGATGAACGCTGGCGGCGTGCTTAACACATGCAAGTCGAACGAAGCACTCTAT<br>TTGATTTCCTTCGGGATTGAAGATTTTGTGACTGAGTGGCGGACGGGTGAGTAACGCGTGGGTAACCTGCCTCAT<br>ACAGGGGGATAACAGTTGGAAACGACTGCTAATACCGCATAAGCGCACRGGATYGCATGATYCGGTGYGAAAAAC<br>TCCGGTGGTAYGRGATGGACCCGCGTCTGATTAGCCAGTTGGCAGGGTAACGGCCTACCAAAGCGACGATCAGTA<br>GCCGACCTGAGAGGGTGACCGGCCACATTGGGACTGAGACACGGCCCAAACTCCTACGGGAGGCAGCAGTGGGGA<br>ATATTGCACAATGGGGGAAACCCTGATGCAGCGACGCCGCGTGAGCGAAGAAGTATTTCGGTATGTAAAGCTCTA<br>TCAGCAGGGAAGAAGAATGACGGTACCTGACTAAGAAGCACCGGCTAAATACGTGCCAGCAGCCGCGGTAATACG<br>TATGGTGCAAGCGTTATCCGGATTTACTGGGTGTAAAGGGAGCGCAGGCGGTGCGGCAAGTCTGATGTGAAAGCC<br>CGGGGCTCAACCCCGGTACTGCATTGGAAACTGTCGTACTAGAGTGTCGGAGGGGTAAGTGGAATTCCTAGTGTA<br>GCGGTGAAATGCGTAGATATTAGGAGGAACACCAGTGGCGAAGGCGGCTTACTGGACGATAACTGACGCTGAGGC<br>TCGAAAGCGTGGGGAGCAAACAGGATTAGATACCCTGGTAGTCCACGCCGTAAACGATGAATACTAGGTGTCGGG<br>GAGCATTGCTCTTCGGTGCCGCAGCAAACGCARTAAGTATTCCACCTGGGGAGTACGTTCGCAAGAATGAAACTC<br>AAAGGAATTGACGGGGACCCGCACAAGCGGTGGAGCATGTGGTTTAATTCGAAGCAACGCGAAGAACCTTACCAA<br>GTCTTGACATCCCGATGRCAGAGTATGTAATGTASYYTCTCYTCGGAGCATCGGTGACAGGTGGTGCATGGTTGT<br>CGTCAGCTCGTGTCGTGAGATGTTGGGTTAAGTCCCGCAACGAGCGCAACCCCTGTTCTTAGTAGCCAGCGGTYC<br>GGCCGGGCACTCTAGGGAGACTGCCAGGGATAACCTGGAGGAAGGCGGGGATGACGTCAAATCATCATGCCCCTT<br>ATGACTTGGGCTACACACGTGCTACAATGGCGTAAACAAAGGGAAGCGGAGCCGTGAGGCCGAGCAAATCTCAAA<br>AATAACGTCTCAGTTCGGACTGTAGTCTGCAACCCGACTACACGAAGCTGGAATCGCTAGTAATCGCAGATCAGA<br>ATGCTGCGGTGAATACGTTCCCGGGTCTTGTACACACCGCCCGTCACACCATGGGAGTTGGAAATGCCCGAAGTC<br>AGTGACCCAACCGCAAGGAGGGAGCTGCCGAAGGCAGGTTCGATAACTGGGGTGAAGTCGTAACAAGGTAGCCGT<br>ATCGGAAGGTGCGGCTGGATCACCTCCTTT |
| SEQ ID NO. 18 *Senegalimassilia anaerobia*<br>ACGGAGAGTTTGATCCTGGCTCAGGATGAACGCTGGCGGCGTGCCTAACACATGCAAGTCGAACGATGAAACCGC<br>CCTCGGGCGGACATGAAGTGGCGAACGGGTGAGTAACACGTGACCGACCTGCCCCCCGCCCAGGGACAGCCCCCC<br>GAAAGGGGGATTAATACCTGGTACTCCGGAAGCGGCGCATGCCGTCTCCGGGAAAGCTTATCGCGGCGGGGGATG<br>GGGTCGCGGCCCATCAGGTAGACGGCGGGGCGACGGCCCACCGTGCCGACGACGGGTAGCCGGGTTGAGAGACCG<br>ACCGGCCACATTGGGACTGAGATACGGCCCAGACTCCTACGGGAGGCAGCAGTGGGGAATTTTGCGCAATGGGGG<br>CAACCCTGACGCAGCAACGCCGCGTGCGGGACGAAGGCGTCCGCGTCGTAAACCGCTTTCAGCGGGGAACACTTW<br>TCGAGGGTACCCGCAGAAGAAGCCCCGGCTAAATACGTGCCAGCAGCCGCGGTAATACGTATGGGGCGAGCGTTA<br>TCCGGATTCATTGGGCGTAAAGCGCGCGTAGGCGGAGCGCTAAGCGGGACCTCTAACCCGAGGGCTCAACCCCCG<br>GCCGGGTCCCGAACTGGCGCTCTCGAGTGCGGTAGGGGAGAGCGGAATTCCCGGTGTAGCGGTGGAATGCGCAGA<br>TATCGGGAAGAACACCGACGGCGAAGGCAGCTCTCTGGGCCGAAACTGACGCTGAGGCGCGAAAGCTGGGGGAGC<br>GAACAGGATTAGATACCCTGGTAGTCCCAGCCGTAAACGATGGGCGCTAGGTGTGGGGGGGAAGACCCCCCGTGC<br>CGCAGCCAACGCATTAAGCGCCCCGCCTGGGGAGTACGGCCGCAAGGCTAAAACTCAAAGGAATTGACGGGGGCC<br>CGCACAAGCAGCGGAGCATGTGGCTTAATTCGAAGCAACGCGAAGAACCTTACCAGGGCTTGACATRYRGGTGAA<br>GCGGCGGAGACGCCGTGGCCGAGAGGAGCCCGCACAGGTGGTGCATGGCTGTCGTCAGCTCGTGTCGTGAGATGT<br>TGGGTTAAGTCCCGCAACGAGCGCAACCCCTGCCCCGTGTTGCCAGCATTCAGTTGGGGACTCGCGGGGGACTGC<br>CGGCGTCAAGCCGGAGGAAGGTGGGGACGACGTCAAGTCATCATGCCCCTTATGCCCTGGGCCGCACACGTGCTA<br>CAATGGCCGGTACAGAGGGTTGCGACCCCGCGAGGGGGAGCGGATCCCGCAAAGCCGGCCCCAGTTCGGATCGGA<br>GGCTGCAACCCGCCTCCGTGAAGCCGGAGTTGCTAGTAATCGCGGATCAGCACGCCGCGGTGAATACGTTCCCGG |

TABLE 11-continued

| Sequences |
|---|
| GCCTTGTACACACCGCCCGTCACACCACCCGAGTCGTCTGCACCCGAAGCCGCCGGCCGAACCCTTTCAGGGGCG<br>GAGGCGTCGAAGGTGTGGAGGGTGAGGGGGGTGAAGTCGTAACAAGGTAGCCGTACCGGAAGGTGCGGCTGGATC<br>ACCTCCTTT |
| SEQ ID NO. 25 *Slackia isoflavoniconvertens*<br>CGGAGAGTTTGATCCTGGCTCAGGATGAACGCTGGCGGCGCGCCTAACACATGCAAGTCGAACGAGTAAGA<br>CGCCTTCGGGCGTGGATAGAGTGGCGAACGGGTGAGTAACACGTGACCAACCTGCCCCCTCCTCCGGGACA<br>ACCTCGGGAAACCGAGGCTAATACCGGATACTCCGGGCCCCCCGCATGGGRKGCCCGGGAAAGCCCTGRCG<br>GGAGGGGATGGGGTCGCGGCCCATCAGGTAGACGGCGGGGTAACGGCCCACCGTGCCYRCWACGGGTAGCC<br>GGGCTGAGAGGCCGATCGGCCACATTGGGACTGAGACACGGCCCAGACTCCTACGGGAGGCAGCAGTGGGG<br>AATTTTGCGCAATGGGGGCAACCCTGACGCAGCGACGCCGCGTGCGGGACGAAGTCATTCGTGACGTAAAC<br>CGCTTTCAGCGAGGAAGAACCATGACGGTACTCGCAGAAGAAGCCCCGGCTAACTACGTGCCAGCAGCCGC<br>GGTAATACGTAGGGGGCGAGCGTTATCCGGAATCATTGGGCGTAAAGCGCGCGCAGGCGGGCTTTCAAGCG<br>GCGGCGTCGAAGCCGGGGGCTCAACCCCCGGAAGCGCCCCGAACTGGAAGCCTCGGATGCGGCAGGGGGAG<br>GCGGAATTCCCGGTGTAGCGGTGAAATGCGCAGATATCGGGAAGAACACCGACGGCGAAGGCAGCCTCCTG<br>GGCCGGCATCGACGCTGAGGCGCGAAAGCTGGGGGAGCGAACAGGATTAGATACCCTGGTAGTCCCAGCCG<br>TAAACGATGGACGCTAGGTGTGGGGGGAWMGRTCCCTCCGTGCCGAAGCCAACGCATTAAGCGTCCCGCCT<br>GGGGAGTACGGCCGCAAGGCTAAAACTCAAAGGAATTGACGGGGGCCCGCACAAGCAGCGGAGCATGTGGC<br>TTAATTCGAAGCAACGCGAAGAACCTTACCAGGGCTTGACATATCGGTGAAGCCGGAGAGATCCGGTGGCC<br>GAGAGGAGCCGATACAGGTGGTGCATGGCTGTCGTCAGCTCGTGCCGTGAGGTGTTGGGTTAAGTCCCGCA<br>ACGAGCGCAACCCCCGCCGCGTGTTGCCAGCATTCAGTTGGGCACTCACGCGGGACTGCCGGCGTCAAGCC<br>GGAGGAAGGCGGGGACGACGTCAAGTCATCATGCCCCTCATGCCCTGGGCCGCACACGTGCTACAATGGCC<br>GGCACAACGGGTTGCCACCCCGCGAGGGGGAGCGGATCCCYAAAGCCGGCCCCAGTTCGGATCGCAGGCTG<br>CAACCCGCCTGCGTGAAGCCGGAGTTGCTAGTAATCGCGGATCAGCACGCCGCGGTGAATACGTTCCCGGG<br>CCTTGTACACACCGCCCGTCACACCACCCGAGTCGTCTGCACCCGAAGCCGCCGGCCGAACCCCTCCGGGG<br>GGCGGAGGCGTCGAAGGTGTGGAGGGTGAGGGGGGTGAAGTCGTAACAAGGTAGCCGTACCGGAAGGTGCG<br>GCTGGATCACCTCCTTT |

Srain sequences are shown above as well as consensus sequences for a strain

Residues are designated according to the IUPAC code

| IUPAC nucleotide code | Base |
|---|---|
| A | Adenine |
| C | Cytosine |
| G | Guanine |
| T (or U) | Thymine (or Uracil) |
| R | A or G |
| Y | C or T |
| S | G or C |
| W | A or T |
| K | G or T |
| M | A or C |
| B | C or G or T |
| D | A or G or T |
| H | A or C or T |
| V | A or C or G |
| N | any base |
| . or - | gap |

REFERENCES

1. Abdulrazeg, O. et al. (2019) "Management of ulcerative colitis: summary of updated NICE guidance," *BMJ*, 367, p. 15897.
2. Caviglia, R., Boskoski, I. and Cicala, M. (2008) "Long-term treatment with infliximab in inflammatory bowel disease: safety and tolerability issues," *Expert opinion on drug safety*. Informa Healthcare, 7(5), pp. 617-632.
3. Costello, S. P. et al. (2017) "Systematic review with meta-analysis: faecal microbiota transplantation for the induction of remission for active ulcerative colitis," *Alimentary pharmacology & therapeutics*. Wiley Online Library, 46(3), pp. 213-224.
4. Costello, S. P. et al. (2019) "Effect of Fecal Microbiota Transplantation on 8-Week Remission in Patients With Ulcerative Colitis: A Randomized Clinical Trial," *JAMA: the journal of the American Medical Association,* 321(2), pp. 156-164.
5. Farrell, R. J. (2019) "Biologics beyond Anti-TNF Agents for Ulcerative Colitis—Efficacy, Safety, and Cost?," *The New England journal of medicine*, pp. 1279-1281.
6. GBD 2017 Inflammatory Bowel Disease Collaborators (2020) "The global, regional, and national burden of inflammatory bowel disease in 195 countries and territories, 1990-2017: a systematic analysis for the Global Burden of Disease Study 2017*," The lancet. Gastroenterology & hepatology,* 5(1), pp. 17-30.
7. Kiesler, P., Fuss, I. J. and Strober, W. (2015) "Experimental models of inflammatory bowel diseases," *Cellular and molecular gastroenterology and hepatology*. Elsevier B V, 1(2), pp. 154-170.
8. Kump, P. et al. (2018) "The taxonomic composition of the donor intestinal microbiota is a major factor influencing the efficacy of faecal microbiota transplantation in therapy refractory ulcerative colitis," *Alimentary pharmacology & therapeutics,* 47(1), pp. 67-77.
9. Metwaly, A. et al. (2020) "Integrated microbiota and metabolite profiles link Crohn's disease to sulfur metabolism," *Nature communications,* 11(1), p. 4322.
10. Moayyedi, P. et al. (2015) "Fecal Microbiota Transplantation Induces Remission in Patients With Active Ulcerative Colitis in a Randomized Controlled Trial," *Gastroenterology,* 149(1), pp. 102-109.e6.
11. Neurath, M. F. (2020) "Host—microbiota interactions in inflammatory bowel disease," Nature reviews. *Gastroenterology & hepatology,* 17(2), pp. 76-77.
12. Rutgeerts, P. et al. (2005) "Infliximab for induction and maintenance therapy for ulcerative colitis," *The New England journal of medicine,* 353(23), pp. 2462-2476.
13. Sokol, H. et al. (2020) "Fecal microbiota transplantation to maintain remission in Crohn's disease: a pilot randomized controlled study," *Microbiome*. Springer Science and Business Media LLC, 8(1), p. 12.
14. Torres, J. et al. (2017) "Crohn's disease," *The Lancet,* 389(10080), pp. 1741-1755. Ungaro, R. et al. (2017)

"Ulcerative colitis," *The Lancet, pp.* 1756-1770. doi: 10.1016/s0140-6736(16)32126-2.
16. Koelink, P. J., et al. "Development of reliable, valid and responsive scoring systems for endoscopy and histology in animal models for inflammatory bowel disease." *Journal of Crohn's and Colitis* 12.7 (2018): 794-803.
17. Johnson, A. D. "An extended IUPAC nomenclature code for polymorphic nucleic acids." *Bioinformatics* 26.10 (2010): 1386-1389.
18. Pandiyan, P., et al. "Microbiome dependent regulation of Tregs and Th17 cells in mucosa." *Frontiers in immunology* 10 (2019): 426
19. Bujko, A., et al, "Transcriptional and functional profiling defines human small intestinal macrophage subsets." *Journal of Experimental Medicine* 215.2 (2018): 441-458.
20. Roncarolo, M. G., et al. "Tr1 cells and the counter-regulation of immunity: natural mechanisms and therapeutic applications." *Interleukin*-10 *in Health and Disease* (2014): 39-68,
21. Yagi, H., et al. "Crucial role of FOXP3 in the development and function of human CD25+ CD4+ regulatory T cells," *International immunology* 16.11 (2004): 1643-1656,
22. van Herk, E. R, and A. Te Velde. "Treg subsets in inflammatory bowel disease and colorectal carcinoma: characteristics, role, and therapeutic targets." *Journal of gastroenterology and hepatology* 31.8 (2016): 1393-1404.

The invention claimed is:

1. A composition comprising isolated bacteria from at least four bacterial species and one or more stabilisers and/or cryoprotectants, wherein the bacteria from the first species comprise a 16S rDNA sequence having at least 98.7% sequence identity with a nucleic acid sequence according to SEQ ID NO: 1, the bacteria from the second species comprise a 16S rDNA sequence having at least 98.7% sequence identity with a nucleic acid sequence according to SEQ ID NO: 2, the bacteria from the third species comprise a 16S rDNA sequence having at least 98.7% sequence identity with a nucleic acid sequence according to SEQ ID NO:3 and the bacteria from the fourth species comprise a 16S rDNA sequence having at least 98.7% sequence identity with a nucleic acid sequence according to SEQ ID NO: 5.

2. The composition according to claim 1 comprising SEQ ID NO: 11, 14 or 17, 18 and 20.

3. The composition according to claim 1 comprising one or more further bacteria selected from bacteria comprising a 16S rDNA sequence having at least 98.7% sequence identity with a nucleic acid sequence according to SEQ ID NO: 4, 12, 15, 19, 6, 21, 7, 22, 8, 23, 9, 13, 24, 10 and/or 25 or further comprising bacteria comprising a 16S rDNA sequence having at least 98.7% sequence identity with a nucleic acid sequence according to SEQ ID NO: 4, 6, 7, 8, 9, or 10.

4. The composition according to claim 1, wherein said composition is in the form of a capsule, tablet, gel or liquid, further optionally, wherein said composition is encapsulated in an enteric coating.

5. The composition according to claim 1, wherein the composition comprises live, attenuated or killed bacteria.

6. The composition according to claim 1, wherein the composition comprises bacterial spores or wherein the composition is substantially free of bacterial spores.

7. The composition according to claim 1, wherein the composition comprises bacterial strains that originate from one or more human donor.

8. The composition according to claim 1, wherein the bacteria are lyophilized, optionally, wherein the composition comprises at least about $1\times10^3$ to $1\times10^{13}$ CFU of bacteria.

9. A pharmaceutical composition comprising a composition of claim 1 and a pharmaceutical carrier.

10. A method for treating ulcerative colitis or Crohn's disease comprising administering a therapeutically effective amount of a composition comprising isolated bacteria from at least four bacterial species wherein the bacteria from the first species comprise a 16S rDNA sequence having at least 98.7% sequence identity with a nucleic acid sequence according to SEQ ID NO: 1, the bacteria from the second species comprise a 16S rDNA sequence having at least 98.7% sequence identity with a nucleic acid sequence according to SEQ ID NO: 2, the bacteria from the third species comprise a 16S rDNA sequence having at least 98.7% sequence identity with a nucleic acid sequence according to SEQ ID NO:3 and the bacteria from the fourth species comprise a 16S rDNA sequence having at least 98.7% sequence identity with a nucleic acid sequence according to SEQ ID NO: 5 to a subject, optionally wherein the composition is administered by oral administration or rectal administration, further optionally, wherein the composition or pharmaceutical composition is administered prior, concurrently or after treatment with another treatment for ulcerative colitis or Crohn's disease.

11. A kit comprising a composition according to claim 1.

12. A food product or a vaccine comprising the composition of claim 1.

13. The composition according to claim 1, further comprising bacteria comprising a 16S rDNA sequence having SEQ ID NO: 6 or 21 and 7 or 22 and 8 or 23 and 10 or 25.

14. The composition according to claim 1, comprising isolated bacteria comprising a 16S rDNA sequence having a nucleic acid sequence according to SEQ ID NO: 1, 2, 3, and 5.

* * * * *